(12) United States Patent
Leonard et al.

(10) Patent No.: US 9,732,392 B2
(45) Date of Patent: Aug. 15, 2017

(54) MODULAR SENSOR ARCHITECTURE FOR CELL BASED BIOSENSORS

(75) Inventors: Joshua N. Leonard, Wilmette, IL (US); Rachel M. Dudek, Evanston, IL (US); Nichole M. Daringer, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/236,974

(22) PCT Filed: Aug. 3, 2012

(86) PCT No.: PCT/US2012/049480
§ 371 (c)(1),
(2), (4) Date: Apr. 2, 2014

(87) PCT Pub. No.: WO2013/022739
PCT Pub. Date: Feb. 14, 2013

(65) Prior Publication Data
US 2014/0234851 A1    Aug. 21, 2014

Related U.S. Application Data

(60) Provisional application No. 61/515,704, filed on Aug. 5, 2011.

(51) Int. Cl.
| | |
|---|---|
| *C12P 21/02* | (2006.01) |
| *C12Q 1/68* | (2006.01) |
| *G01N 33/566* | (2006.01) |
| *G01N 33/58* | (2006.01) |
| *G01N 33/68* | (2006.01) |
| *C12N 9/48* | (2006.01) |
| *C12N 9/50* | (2006.01) |
| *C12N 5/10* | (2006.01) |
| *C12N 15/79* | (2006.01) |

(52) U.S. Cl.
CPC ......... *C12Q 1/6897* (2013.01); *G01N 33/566* (2013.01); *G01N 33/582* (2013.01); *G01N 33/6872* (2013.01)

(58) Field of Classification Search
None
See application file for complete search history.

(56) References Cited

U.S. PATENT DOCUMENTS

| 7,585,635 B2 | 9/2009 | Rossner et al. |
| 2007/0224615 A1 | 9/2007 | Lee et al. |

OTHER PUBLICATIONS

Adams et al., "Structure, function, and pathophysiology of protease activated receptors" 130 Pharmacology & Therapeutics 248-282 (Jun. 2011).*

Barnea et al., "The genetic design of signaling cascades to record receptor activation," Proc Natl Acad Sci U S A. Jan. 8, 2008;105(1):64-9.
Georgiou et al., "Display of heterologous proteins on the surface of microorganisms: from the screening of combinatorial libraries to live recombinant vaccines," Nat Biotechnol, 1997, 15(1):29-34.
Hudson and Kortt et al., "High avidity scFv multimers; diabodies and triabodies," J Immunol Methods, 1999, 231 (1-2):177-189.
International Search Report, mailed Jan. 9, 2013, for International Patent Application No. PCT/US2012/049480, 4 pages.
Kapust et al., "The P1' specificity of tobacco etch virus protease," Biochem Biophys Res Commun, 2002, 294 (5):949-955.
Kapust et al., "Tobacco etch virus protease: mechanism of autolysis and rational design of stable mutants with wild-type catalytic proficiency," Protein Eng, 2001, 14(12):993-1000.
Kieke et al., "Isolation of anti-T cell receptor scFv mutants by yeast surface display," Protein Eng, 1997, 10 (11):1303-1310.
Lee and Maheshri, "A regulatory role for repeated decoy transcription factor binding sites in target gene expression," Mol Syst Biol, 2012 8:576.
Lopez-Otin and Bond, "Proteases: Multifunctional Enzymes in Life and Disease," J. Biol. Chem., 2008, 283:30433-30437.
Lopez-Otin and Overall, "Protease degradomics: a new challenge for proteomics," Nat. Rev. Mol., 2002, Cell Biol., 2:509-519.
Matthias et al., "Disulfide exchange in domain 2 of CD4 is required for entry of HIV-1," Nat Immunol, 2002, 3 (8):727-732.
Nunn et al., "Crystal structure of tobacco etch virus protease shows the protein C terminus bound within the active site," J Mol Biol, 2005, 350(1):145-155.
Overall and Blobel, "In search of partners: linking extracellular proteases to substrates," Nat. Rev. Mol., 2007, Cell Biol., 8: 245-257.
Panter and Jerala, "The ectodomain of the Toll-like receptor 4 prevents constitutive receptor activation," J Biol Chem, 2011, 286(26):23334-23344.
Shaner et al., "Improved monomeric red, orange and yellow fluorescent proteins derived from *Discosoma* sp. red fluorescent protein," Nat Biotechnol, 2004, 22(12):1567-1572.
Tong, "Viral proteases," Chem. Rev., 2002, 102, 4609-4626.
Turk et al., "Protease signalling: the cutting edge," The EMBO Journal, 2012, 31(7): 1630-1643.
Wouters et al., "Cross-strand disulphides in cell entry proteins: poised to act," Bioessays, 2004, 26(1):73-79.

* cited by examiner

*Primary Examiner* — Nancy J Leith
(74) *Attorney, Agent, or Firm* — Andrus Intellectual Property Law, LLP

(57) ABSTRACT

The present invention provides modular extracellular sensors, nucleic acids encoding such sensors, and cells expressing such sensors, and methods of employing such sensors and cells for detecting extracellular ligands. In certain embodiments, the extracellular sensors comprise a ligand binding domain, a transmembrane domain, a protease domain, a protease cleavage site, and a transcription factor. In other embodiments, a pair of extracellular receptors is provided where both receptors contain a ligand binding domain and transmembrane domain, and one receptor contains a protease cleavage site and a transcription factor and the other receptor contains a protease domain.

20 Claims, 25 Drawing Sheets

FIG. 7

A. mCherry_PCS-OX_tTA

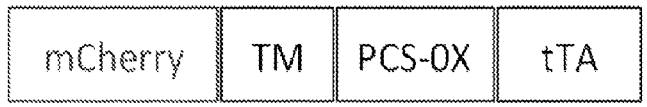

B. Nucleotide sequence (SEQ ID NO:1)
ATGTGCCGAGCCATCTCTCTTAGGCGCTTGCTGCTGCTGCTGCAGCTGTCACAACTCCTAGCTGTCACTCAAGG
GATGGTGAGCAAGGGCGAGGAGGATAACATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCCTACGAGGGCACCCAGACCGCCAAGCTG
AAGGTGACCAAGGGTGGCCCCCTGCCCTTCGCCTGGGACATCCTGTCCCCTCAGTTCATGTACGGCTCCAAGGCCTA
CGTGAAGCACCCCGCCGACATCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCG
GATGTACCCCGAGGACGGCGCCCTGAAGGGCGAGATCAAGCAGAGGCTGAAGCTGAAGGACGGCGGCCACTACGACG
CTGAGGTCAAGACCACCTACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCGCCACTCCACCGGCGGCAT
GGACGAGCTGTACAAGAAGCTTTTTGGGCACTGGTCGTGGTTGCTGGAGTCCTGTTTTGTTATGGCTTGCTAGTGA
CAGTGGCTCTTTGTGTTGAAAACCTGTATTTTCAGGGTATGTCTAGATTAGATAAAAGTAAAGTGATTAACAGCGCA
TTAGAGCTGCTTAATGAGGTCGGAATCGAAGGTTTAACAACCCGTAAACTCGCCCAGAAGCTAGGTGTAGAGCAGCC
TACATTGTATTGGCATGTAAAAAATAAGCGGGCTTTGCTCGACGCCTTAGCCATTGAGATGTTAGATAGGCACCATA
CTCACTTTTGCCCTTTAGAAGGGGAAAGCTGGCAAGATTTTTTACGTAATAACGCTAAAAGTTTTAGATGTGCTTTA
CTAAGTCATCGCGATGGAGCAAAAGTACATTTAGGTACACGGCCTACAGAAAAACAGTATGAAACTCTCGAAAATCA
ATTAGCCTTTTTATGCCAACAAGGTTTTTCACTAGAGAATGCATTATATGCACTCAGCGCTGTGGGGCATTTTACTT
TAGGTTGCGTATTGGAAGATCAAGAGCATCAAGTCGCTAAAGAAGAAAGGGAAACACCTACTACTGATAGTATGCCG
CCATTATTACGACAAGCTATCGAATTATTTGATCACCAAGGTGCAGAGCCAGCCTTCTTATTCGGCCTTGAATTGAT
CATATGCGGATTAGAAAAACAACTTAAATGTGAAAGTGGGTCCGCGTACAGCCGCGCGCGTACGAAAAACAATTACG
GGTCTACCATCGAGGGCCTGCTCGATCTCCCGGACGACGACGCCCCCGAAGAGGCGGGGCTGGCGGCTCCGCGCCTG
TCCTTTCTCCCCGCGGGACACACGCGCAGACTGTCGACGGCCCCCCCGACCGATGTCAGCCTGGGGGACGAGCTCCA
CTTAGACGGCGAGGACGTGGCGATGGCGCATGCCGACGCGCTAGACGATTTCGATCTGGACATGTTGGGGGACGGGG
ATTCCCCGGGTCCGGGATTTACCCCCCACGACTCCGCCCCCTACGGCGCTCTGGATATGGCCGACTTCGAGTTTGAG
CAGATGTTTACCGATGCCCTTGGAATTGACGAGTACGGTGGGTAG

C. Amino acid sequence (SEQ ID NO:2)
MCRAISLRRILLLLLQLSQLLAVTQGMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCV<u>ENLYFQ</u>XMSRLDKSKVINSA
LELLNEVGIEGLTTRKLAQKLGVEQPTLYWHVKNKRALLDALAIEMLDRHHTHFCPLEGESWQDFLRNNAKSFRCAL
LSHRDGAKVHLGTRPTEKQYETLENQLAFLCQQGFSLENALYALSAVGHFTLGCVLEDQEHQVAKEERETPTTDSMP
PLLRQAIELFDHQGAEPAFLFGLELIICGLEKQLKCESGSAYSRARTKNNYGSTIEGLLDLPDDDAPEEAGLAAPRL
SFLPAGHTRRLSTAPPTDVSLGDELHLDGEDVAMAHADALDDFDLDMLGDGDSPGPGFTPHDSAPYGALDMADFEFE
QMFTDALGIDEYGG where X is either G, A, E, L, S, Y, or K.

FIG. 8

A. mCherry_PCS-2X_tTA

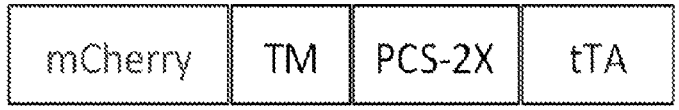

B. Nucleotide sequence (SEQ ID NO:3)
ATGTGCCGAGCCATCTCTCTTAGGCGCTTGCTGCTGCTGCTGCAGCTGTCACAACTCCTAGCTGTCACTCAAGG
GATGGTGAGCAAGGGCGAGGAGGATAACATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCCTACGAGGGCACCCAGACCGCCAAGCTG
AAGGTGACCAAGGGTGGCCCCCTGCCCTTCGCCTGGGACATCCTGTCCCCTCAGTTCATGTACGGCTCCAAGGCCTA
CGTGAAGCACCCCGCCGACATCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCG
GATGTACCCCGAGGACGGCGCCCTGAAGGGCGAGATCAAGCAGAGGCTGAAGCTGAAGGACGGCGGCCACTACGACG
CTGAGGTCAAGACCACCTACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCGCCACTCCACCGGCGGCAT
GGACGAGCTGTACAAGAAGCTTTTTGGGCACTGGTCGTGGTTGCTGGAGTCCTGTTTTGTTATGGCTTGCTAGTGA
CAGTGGCTCTTTGTGTTATCTGGGTAAGATCTGGTGAAAACCTGTATTTTCAGGGTATGTCTAGATTAGATAAAAGT
AAAGTGATTAACAGCGCATTAGAGCTGCTTAATGAGGTCGGAATCGAAGGTTTAACAACCCGTAAACTCGCCCAGAA
GCTAGGTGTAGAGCAGCCTACATTGTATTGGCATGTAAAAAATAAGCGGGCTTTGCTCGACGCCTTAGCCATTGAGA
TGTTAGATAGGCACCATACTCACTTTTGCCCTTTAGAAGGGGAAAGCTGGCAAGATTTTTTACGTAATAACGCTAAA
AGTTTTAGATGTGCTTTACTAAGTCATCGCGATGGAGCAAAAGTACATTTAGGTACACGGCCTACAGAAAAACAGTA
TGAAACTCTCGAAAATCAATTAGCCTTTTTATGCCAACAAGGTTTTTCACTAGAGAATGCATTATATGCACTCAGCC
CTGTGGGGCATTTTACTTTAGGTTGCGTATTGGAAGATCAAGAGCATCAAGTCGCTAAAGAAGAAAGGGAAACACCT
ACTACTGATAGTATGCCGCCATTATTACGACAAGCTATCGAATTATTTGATCACCAAGGTGCAGAGCCAGCCTTCTT
ATTCGGCCTTGAATTGATCATATGCGGATTAGAAAAACAACTTAAATGTGAAAGTGGGTCCGCGTACAGCCGCGCGC
GTACGAAAAACAATTACGGGTCTACCATCGAGGGCCTGCTCGATCTCCCGGACGACGACGCCCCCGAAGAGGCGGGC
CTGGCGGCTCCGCGCCTGTCCTTTCTCCCCGCGGGACACACGCGCAGACTGTCGACGGCCCCCCCGACCGATGTCAG
CCTGGGGGACGAGCTCCACTTAGACGGCGAGGACGTGGCGATGGCGCATGCCGACGCGCTAGACGATTTCGATCTGG
ACATGTTGGGGGACGGGGATTCCCCGGGTCCGGGATTTACCCCCACGACTCCGCCCCCTACGGCGCTCTGGATATG
GCCGACTTCCAGTTTGAGCAGATGTTTACCGATGCCCTTGGAATTGACGAGTACGGTGGGTAG

C. Amino acid sequence (SEQ ID NO:4)
MCRAISLRRLLLLLLQLSQLLAVTQGMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCVINRSGENLYFQXMSRLDKS
KVINSALELLNEVGIEGLTTRKLAQKLGVEQPTLYWHVKNKRALLDALAIEMLDRHHTHFCPLEGESWQDFLRNNAK
SFRCALLSHRDGAKVHLGTRPTEKQYETLENQLAFLCQQGFSLENALYALSAVGHFTLGCVLEDQEHQVAKEERETP
TTDSMPPLLRQAIELFDHQGAEPAFLFGLELIICGLEKQLKCESGSAYSRARTKNNYGSTIEGLLDLPDDDAPEEAG
LAAPRLSFLPAGHTRRLSTAPPTDVSLGDELHLDGEDVAMAHADALDDFDLDMLGDGDSPGPGFTPHDSAPYGALDM
ADFEFEQMFTDALGIDEYGG where X is either G, A, E, L, S, Y, or K.

FIG. 9

A. mCherry ISP-0 TEV

B. Nucleotide sequence (SEQ ID NO:5)
ATGTGCCGAGCCATCTCTCTTAGGCGCTTGCTGCTGCTGCTGCTGCAGCTGTCACAACTCCTAGCTGTCACTCAAGG
GATGGTGAGCAAGGGCGAGGAGGATAACATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCCTACGAGGGCACCCAGACCGCCAAGCTG
AAGGTGACCAAGGGTGGCCCCCTGCCCTTCGCCTGGGACATCCTGTCCCCTCAGTTCATGTACGGCTCCAAGGCCTA
CGTGAAGCACCCCGCCGACATCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCG
GATGTACCCCGAGGACGGCGCCCTGAAGGGCGAGATCAAGCAGAGGCTGAAGCTGAAGGACGGCGGCCACTACGACG
CTGAGGTCAAGACCACCTACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCGCCACTCCACCGGCGGCAT
GGACGAGCTGTACAAGAAGCTTTTTGGGCACTGGTCGTGGTTGCTGGAGTCCTGTTTTGTTATGGCTTGCTAGTGA
CAGTGGCTCTTTGTGTTGAGAGCTTGTTTAAGGGGCCGCGTGATTACAACCCGATATCGAGCACCATTTGTCATTTG
ACGAATGAATCTGATGGGCACACAACATCGTTGTATGGTATTGGATTTGGTCCCTTCATCATTACAAACAAGCACTT
GTTTAGAAGAAATAATGGAACACTGTTGGTCCAATCACTACATGGTGTATTCAAGGTCAAGAACACCACGACTTTGC
AACAACACCTCATTGATGGGAGGGACATGATAATTATTCGCATGCCTAAGGATTTCCCACCATTTCCTCAAAAGCTG
AAATTTAGAGAGCCACAAAGGGAAGAGCGCATATGTCTTGTGACAACCAACTTCCAAACTAAGAGCATGTCTAGCAT
GGTGTCAGACACTAGTTGCACATTCCCTTCATCTGATGGCATATTCTGGAAGCATTGGATTCAAACCAAGGATGGGC
AGTGTGGCAGTCCATTAGTATCAACTAGAGATGGGTTCATTGTTGGTATACACTCAGCATCGAATTTCACCAACACA
AACAATTATTTCACAAGCGTGCCGAAAAACTTCATGGAATTGTTGACAAATCAGGAGGCGCAGCAGTGGGTTAGTGG
TTGGCGATTAAATGCTGACTCAGTATTGTGGGGGGGCCATAAAGTTTTCATGGTGAAACCTGAAGAGCCTTTTCAGC
CAGTTAAGGAAGCGACTCAACTCATGAATTAG

C. Amino acid sequence (SEQ ID NO:6)
MCRAISLRRLLLLLLQLSQLLAVTQGMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCVESLFKGPRDYNPISSTICHL
TNESDGHTTSLYGIGFGPFIITNKHLFRRNNGTLLVQSLHGVFKVKNTTTLQQHLIDGRDMIIRMPKDFPPFPQKL
KFREPQREERICLVTTNFQTKSMSSMVSDTSCTFPSSDGIFWKHWIQTKDGQCGSPLVSTRDGFIVGIHSASNFTNT
NNYFTSVPKNFMELLTNQEAQQWVSGWRLNADSVLWGGHKVFMVKPEEPFQPVKEATQLMN

FIG. 10

A. mCherry_ISP-2_TEV

B. Nucleotide sequence (SEQ ID NO:7)
ATGTGCCGAGCCATCTCTCTTAGGCGCTTGCTGCTGCTGCTGCTGCAGCTGTCACAACTCCTAGCTGTCACTCAAGG
GATGGTGAGCAAGGGCGAGGAGGATAACATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCCTACGAGGGCACCCAGACCGCCAAGCTG
AAGGTGACCAAGGGTGGCCCCCTGCCCTTCGCCTGGGACATCCTGTCCCCTCAGTTCATGTACGGCTCCAAGGCCTA
CGTGAAGCACCCCGCCGACATCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCG
GATGTACCCCGAGGACGGCGCCCTGAAGGGCGAGATCAAGCAGAGGCTGAAGCTGAAGGACGGCGGCCACTACGACG
CTGAGGTCAAGACCACCTACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCGCCACTCCACCGGCGGCAT
GGACGAGCTGTACAAGAAGCTTTTTGGGCACTGGTCGTGGTTGCTGGAGTCCTGTTTTGTTATGGCTTGCTAGTGA
CAGTGGCTCTTTGTGTTATCTGGGTAAGATCTGGTGAGAGCTTGTTTAAGGGGCCGCGTGATTACAACCCGATATCG
AGCACCATTTGTCATTTGACGAATGAATCTGATGGGCACACAACATCGTTGTATGGTATTGGATTTGGTCCCTTCAT
CATTACAAACAAGCACTTGTTTAGAAGAAATAATGGAACACTGTTGGTCCAATCACTACATGGTGTATTCAAGGTCA
AGAACACCACGACTTTGCAACAACACCTCATTGATGGGAGGGACATGATAATTATTCGCATGCCTAAGGATTTCCCA
CCATTTCCTCAAAAGCTGAAATTTAGAGAGCCACAAAGGGAAGAGCGCATATGTCTTGTGACAACCAACTTCCAAAC
TAAGAGCATGTCTAGCATGGTGTCAGACACTAGTTGCACATTCCCTTCATCTGATGGCATATTCTGGAAGCATTGGA
TTCAAACCAAGGATGGGCAGTGTGGCAGTCCATTAGTATCAACTAGAGATGGGTTCATTGTTGGTATACACTCAGCA
TCGAATTTCACCAACACAAACAATTATTTCACAAGCGTGCCGAAAAACTTCATGGAATTGTTGACAAATCAGGAGGC
GCAGCAGTGGGTTAGTGGTTGGCGATTAAATGCTGACTCAGTATTGTGGGGGGGCCATAAAGTTTTCATGGTGAAAC
CTGAAGAGCCTTTTCAGCCAGTTAAGGAAGCGACTCAACTCATGAATTAG

C. Amino acid sequence (SEQ ID NO:8)
MCRAISLRRLLLLLLQLSQLLAVTQGMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCVIWVRSGESLFKGPRDYNPIS
STICHLTNESDGHTTSLYGIGFGPFIITNKHLFRRNNGTLLVQSLHGVFKVKNTTTLQQHLIDGRDMIIIRMPKDFP
PFPQKLKFREPQREERICLVTTNFQTKSMSSMVSDTSCTFPSSDGIFWKHWIQTKDGQCGSPLVSTRDGFIVGIHSA
SNFTNTNNYFTSVPKNFMELLTNQEAQQWVSGWRLNADSVLWGGHKVFMVKPEEPFQPVKEATQLMN

FIG. 11

A. dTomato_PCS-OX_tTA

B. Nucleotide sequence (SEQ ID NO:9)
ATGTGCCGAGCCATCTCTCTTAGGCGCTTGCTGCTGCTGCTGCTGCAGCTGTCACAACTCCTAGCTGTCACTCAAGG
GGTGAGCAAGGGCGAGGAGGTCATCAAAGAGTTCATGCGCTTCAAGGTGCGCATGGAGGGCTCCATGAACGGCCACG
AGTTCGAGATCGAGGGCGAGGGCGAGGGCCGCCCCTACGAGGGCACCCAGACCGCCAAGCTGAAGGTGACCAAGGGC
GGCCCCCTGCCCTTCGCCTGGGACATCCTGTCCCCCCAGTTCATGTACGGCTCCAAGGCGTACGTGAAGCACCCCGC
CGACATCCCCGATTACAAGAAGCTGTCCTTCCCCGAGGGCTTCAAGTGGGAGCGCGTGATGAACTTCGAGGACGGCG
GTCTGGTGACCGTGACCCAGGACTCCTCCCTGCAGGACGGCACGCTGATCTACAAGGTGAAGATGCGCGGCACCAAC
TTCCCCCCCGACGGCCCCGTAATGCAGAAGAAGACCATGGGCTGGGAGGCCTCCACCGAGCGCCTGTACCCCGCGA
CGGCGTGCTGAAGGGCGAGATCCACCAGGCCCTGAAGCTGAAGGACGGCGGCCACTACCTGGTGGAGTTCAAGACCA
TCTACATGGCCAAGAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACGGCATGGACGAGCT
GTACAAGAAGCTTTTTTGGGCACTGGTCGTGGTTGCTGGAGTCCTGTTTTGTTATGGCTTGCTAGTGACAGTGGCTC
TTTGTGTTGAAAACCTGTATTTTCAGGGTATGTCTAGATTAGATAAAAGTAAAGTGATTAACAGCGCATTAGAGCTG
CTTAATGAGGTCGGAATCGAAGGTTTAACAACCCGTAAACTCGCCCAGAAGCTAGGTGTAGAGCAGCCTACATTGTA
TTGGCATGTAAAAAATAAGCGGGCTTTGCTCGACGCCTTAGCCATTGAGATGTTAGATAGGCACCATACTCACTTTT
GCCCTTTAGAAGGGGAAAGCTGGCAAGATTTTTTACGTAATAACGCTAAAAGTTTTAGATGTGCTTTACTAAGTCAT
CGCGATGGAGCAAAAGTACATTTAGGTACACGGCCTACAGAAAAACAGTATGAAACTCTCGAAAATCAATTAGCCTT
TTTATGCCAACAAGGTTTTTCACTACAGAATGCATTATATGCACTCAGCGCTGTGGGCATTTTACTTTAGGTTGCG
TATTGGAAGATCAAGAGCATCAAGTCGCTAAAGAAGAAAGGGAAACACCTACTACTGATAGTATGCCGCCATTATTA
CGACAAGCTATCGAATTATTTGATCACCAAGGTGCAGAGCCAGCCTTCTTATTCGGCCTTGAATTGATCATATGCGG
ATTAGAAAAACAACTTAAATGTGAAAGTGGGTCCGCGTACAGCCGCGCGCGTACGAAAAACAATTACGGGTCTACCA
TCGAGGGCCTGCTCGATCTCCCGGACGACGACGCCCCCGAAGAGGCGGGGCTGGCGGCTCCGCGCCTGTCCTTTCTC
CCCGCGGGACACACGCGCAGACTGTCGACGGCCCCCCCGACCGATGTCAGCCTGGGGACGAGCTCCACTTAGACGG
CGAGGACGTGGCGATGGCGCATGCCGACGCGCTAGACGATTTCGATCTGGACATGTTGGGGGACGGGGATTCCCCGG
GTCCGGGATTTACCCCCCACGACTCCGCCCCCTACGGCGCTCTGGATATGGCCGACTTCGAGTTTGAGCAGATGTTT
ACCGATGCCCTTGGAATTGACGAGTACGGTGGGTAG C. Amino acid sequence   (SEQ ID NO:10)
MCRAISLRRLLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYYVDTKLDITSHN
EDYTIVEQYERSEGRHHLFLYGMDELYKKLFWALVVVAGVLFCYGLLVTVALCVENLYFQXMSRLDKSKVINSALEL
LNEVGIEGLTTRKLAQKLGVEQPTLYWHVKNKRALLDALAIEMLDRHHTHFCPLEGESWQDFLRNNAKSFRCALLSH
RDGAKVHLGTRPTEKQYETLENQLAFLCQQGFSLENALYALSAVGHFTLGCVLEDQEHQVAKEERETPTTDSMPPLL
RQAIELFDHQGAEPAFLFGLELIICGLEKQLKCESGSAYSRARTKNNYGSTIEGLLDLPDDDAPEEAGLAAPRLSFL
PAGHTRRLSTAPPTDVSLGDELHLDGEDVAMAHADALDDFDLDMLGDGDSPGPGFTPHDSAPYGALDMADFEFEQMF
TDALGIDEYGG where X is either G, A, E, L, S, Y, or K.

FIG. 12

A. dTomato_PCS-2X_tTA

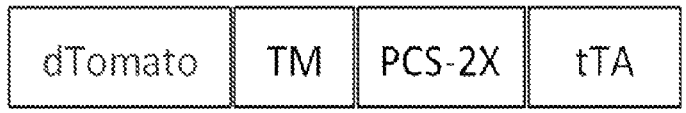

B. Nucleotide sequence   (SEQ ID NO:11)
ATGTGCCGAGCCATCTCTCTTAGGCGCTTGCTGCTGCTGCTGCTGCAGCTGTCACAACTCCTAGCTGTCACTCAAGG
GGTGAGCAAGGGCGAGGAGGTCATCAAAGAGTTCATGCGCTTCAAGGTGCGCATGGAGGGCTCCATGAACGGCCACG
AGTTCGAGATCGAGGGCGAGGGCGAGGGCCGCCCCTACGAGGGCACCCAGACCGCCAAGCTGAAGGTGACCAAGGGC
GGCCCCCTGCCCTTCGCCTGGGACATCCTGTCCCCCAGTTCATGTACGGCTCCAAGGCGTACGTGAAGCACCCCGC
CGACATCCCCGATTACAAGAAGCTGTCCTTCCCCGAGGGCTTCAAGTGGGAGCGCGTGATGAACTTCGAGGACGGCG
GTCTGGTGACCGTGACCCAGGACTCCTCCCTGCAGGACGGCACGCTGATCTACAAGGTGAAGATGCGCGGCACCAAC
TTCCCCCCCGACGGCCCCGTAATGCAGAAGAAGACCATGGGCTGGGAGGCCTCCACCGAGCGCCTGTACCCCGCGA
CGGCGTGCTGAAGGGCGAGATCCACCAGGCCCTGAAGCTGAAGGACGGCGGCCACTACCTGGTGGAGTTCAAGACCA
TCTACATGGCCAAGAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACGGCATGGACGAGCT
GTACAAGAAGCTTTTTGGGCACTGGTCGTGGTTGCTGGAGTCCTGTTTTGTTATGGCTTGCTAGTGACAGTGGCTC
TTTGTGTTATCTGGGTAAGATCTGGTGAAAACCTGTATTTTCAGGGTATGTCTAGATTAGATAAAAGTAAAGTGATT
AACAGCGCATTAGAGCTGCTTAATGAGGTCGGAATCGAAGGTTTAACAACCCGTAAACTCGCCCAGAAGCTAGGTGT
AGAGCAGCCTACATTGTATTGGCATGTAAAAAATAAGCGGGCTTTGCTCGACGCCTTAGCCATTGAGATGTTAGATA
GGCACCATACTCACTTTTGCCCTTTAGAAGGGGAAAGCTGGCAAGATTTTTACGTAATAACGCTAAAAGTTTTAGA
TGTGCTTTACTAAGTCATCGCGATGGAGCAAAAGTACATTTAGGTACACGGCCTACAGAAAAACAGTATGAAACTCT
CGAAAATCAATTAGCCTTTTTATGCCAACAAGGTTTTTCACTAGAGAATGCATTATATGCACTCAGCGCTGTGGGGC
ATTTTACTTTAGGTTGCGTATTGGAAGATCAAGAGCATCAAGTCGCTAAAGAAGAAAGGGAAACACCTACTACTGAT
AGTATGCCGCCATTATTACGACAAGCTATCGAATTATTTGATCACCAAGGTGCAGAGCCAGCCTTCTTATTCGGCCT
TGAATTGATCATATGCGGATTAGAAAAACAACTTAAATGTGAAAGTGGGTCCGCGTACAGCCGCGCGTACGAAAA
ACAATTACGGGTCTACCATCGAGGGCCTGCTCGATCTCCCGGACGACGACGCCCCCGAAGAGGCGGGGCTGGCGGCT
CCGCGCCTGTCCTTTCTCCCCGCGGGACACACGCGCAGACTGTCGACGGCCCCCCCGACCGATGTCAGCCTGGGGGA
CGAGCTCCACTTAGACGGCGAGGACGTGGCGATGGCGCATGCCGACGCGCTAGACGATTTCGATCTGGACATGTTGG
GGGACGGGGATTCCCCGGGTCCGGGATTTACCCCCCACGACTCCGCCCCCTACGGCGCTCTGGATATGGCCGACTTC
GAGTTTGAGCAGATGTTTACCGATGCCCTTGGAATTGACGAGTACGGTGGGTAG

C. Amino acid sequence   (SEQ ID NO:12)
MCRAISLRRLLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYYVDTKLDITSHN
EDYTIVEQYERSEGRHHLFLYGMDELYKKLFWALVVVAGVLFCYGLLVTVALCVIWRSSENLYFQXMSRLDKSKVI
NSALELLNEVGIEGLTTRKLAQKLGVEQPTLYWHVKNKRALIDALAIEMLDRHHTHFCPLEGESWQDFLRNNAKSFR
CALLSHRDGAKVHLGTRPTEKQYETLENQLAFLCQQGFSLENALYALSAVGHFTLGCVLEDQEHQVAKEERETPTTD
SMPPLLRQAIELFDHQGAEPAFLFGLELIICGLEKQLKCESGSAYSRARTKNNYGSTIEGLLDLPDDDAPEEAGLAA
PRLSFLPAGHTRRLSTAPPTDVSLGDELHLDGEDVAMAHADALDDFDLDMLGDGDSPGPGFTPHDSAPYGALDMADF
EFEQMFTDALGIDEYGG

FIG. 13

A. dTomato ISP-0 TEV

B. Nucleotide sequence (SEQ ID NO:13)
ATGTGCCGAGCCATCTCTCTTAGGCGCTTGCTGCTGCTGCTGCTGCAGCTGTCACAACTCCTAGCTGTCACTCAAGG
GGTGAGCAAGGGCGAGGAGGTCATCAAAGAGTTCATGCGCTTCAAGGTGCGCATGGAGGGCTCCATGAACGGCCACG
AGTTCGAGATCGAGGGCGAGGGCGAGGGCCGCCCCTACGAGGGCACCCAGACCGCCAAGCTGAAGGTGACCAAGGGC
GGCCCCCTGCCCTTCGCCTGGGACATCCTGTCCCCCCAGTTCATGTACGGCTCCAAGGCGTACGTGAAGCACCCCGC
CGACATCCCCGATTACAAGAAGCTGTCCTTCCCCGAGGGCTTCAAGTGGGAGCGCGTGATGAACTTCGAGGACGGCG
GTCTGGTGACCGTGACCCAGGACTCCTCCCTGCAGGACGGCACGCTGATCTACAAGGTGAAGATGCGCGGCACCAAC
TTCCCCCCCGACGGCCCCGTAATGCAGAAGAAGACCATGGGCTGGGAGGCCTCCACCGAGCGCCTGTACCCCGCGA
CGGCGTGCTGAAGGGCGAGATCCACCAGGCCCTGAAGCTGAAGGACGGCGGCCACTACCTGGTGGAGTTCAAGACCA
TCTACATGGCCAAGAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACGGCATGGACGAGCT
GTACAAGAAGCTTTTTGGGCACTGGTCGTGGTTGCTGGAGTCCTGTTTTGTTATGGCTTGCTAGTGACAGTGGCTC
TTTGTGTTGAGAGCTTGTTTAAGGGGCCGCGTGATTACAACCCGATATCGAGCACCATTTGTCATTTGACGAATGAA
TCTGATGGGCACACAACATCGTTGTATGGTATTGGATTTGGTCCCTTCATCATTACAAACAAGCACTTGTTTAGAAG
AAATAATGGAACACTGTTGGTCCAATCACTACATGGTGTATTCAAGGTCAAGAACACCACGACTTTGCAACAACACC
TCATTGATGGGAGGGACATGATAATTATTCGCATGCCTAAGGATTTCCCACCATTTCCTCAAAAGCTGAAATTTAGA
GAGCCACAAAGGGAAGAGCGCATATGTCTTGTGACAACCAACTTCCAAACTAAGAGCATGTCTAGCATGGTGTCAGA
CACTAGTTGCACATTCCCTTCATCTGATGGCATATTCTGGAAGCATTGGATTCAAACCAAGGATGGGCAGTGTGGCA
GTCCATTAGTATCAACTAGAGATGGGTTCATTGTTGGTATACACTCAGCATCGAATTTCACCAACACAAACAATTAT
TTCACAAGCGTGCCGAAAAACTTCATGGAATTGTTGACAAATCAGGAGGCGCAGCAGTGGGTTAGTGGTTGGCGATT
AAATGCTGACTCAGTATTGTGGGGGGGCCATAAAGTTTTCATGGTGAAACCTGAAGAGCCTTTTCAGCCAGTTAAGG
AAGCGACTCAACTCATGAATTAG

C. Amino acid sequence (SEQ ID NO:14)
MCRAISLRRLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYYVDTKLDITSHN
EDYTIVEQYERSEGRHHLFLYGMDELYKKLFWALVVVAGVLFCYGLLVTVALCVESLFKGPRDYNPISSTICHLTNE
SDGHTTSLYGIGFGPFIITNKHLFRRNNGTLLVQSLHGVFKVKNTTTLQQHLIDGRDMIIIRMPKDFPPFPQKLKFR
EPQREERICLVTTNFQTKSMSSMVSDTSCTFPSSDGIFWKHWIQTKDGQCGSPLVSTRDGFIVGIHSASNFTNTNNY
FTSVPKNFMELLTNQEAQQWVSGWRLNADSVLWGGHKVFMVKPEEPFQPVKEATQLMN

FIG. 14

A. dTomato_ISP-2_TEV

B. Nucleotide sequence (SEQ ID NO:15)
ATGTGCCGAGCCATCTCTCTTAGGCGCTTGCTGCTGCTGCTGCTGCAGCTGTCACAACTCCTAGCTGTCACTCAAGG
GGTGAGCAAGGGCGAGGAGGTCATCAAAGAGTTCATGCGCTTCAAGGTGCGCATGGAGGGCTCCATGAACGGCCACG
AGTTCGAGATCGAGGGCGAGGGCGAGGGCCGCCCCTACGAGGGCACCCAGACCGCCAAGCTGAAGGTGACCAAGGGC
GGCCCCCTGCCCTTCGCCTGGGACATCCTGTCCCCCCAGTTCATGTACGGCTCCAAGGCGTACGTGAAGCACCCCGC
CGACATCCCCGATTACAAGAAGCTGTCCTTCCCCGAGGGCTTCAAGTGGGAGCGCGTGATGAACTTCGAGGACGGCG
GTCTGGTGACCGTGACCCAGGACTCCTCCCTGCAGGACGGCACGCTGATCTACAAGGTGAAGATGCGCGGCACCAAC
TTCCCCCCCGACGGCCCCGTAATGCAGAAGAAGACCATGGGCTGGGAGGCCTCCACCGAGCGCCTGTACCCCGCGA
CGGCGTGCTGAAGGGCGAGATCCACCAGGCCCTGAAGCTGAAGGACGGCGGCCACTACCTGGTGGAGTTCAAGACCA
TCTACATGGCCAAGAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACGGCATGGACGAGCT
GTACAAGAAGCTTTTTTGGGCACTGGTCGTGGTTGCTGGAGTCCTGTTTTGTTATGGCTTGCTAGTGACAGTGGCTC
TTTGTGTTATCTGGGTAAGATCTGGTGAGAGCTTGTTTAAGGGGCCGCGTGATTACAACCCGATATCGAGCACCATT
TGTCATTTGACGAATGAATCTGATGGGCACACAACATCGTTGTATGGTATTGGATTTGGTCCCTTCATCATTACAAA
CAAGCACTTGTTTAGAAGAAATAATGGAACACTGTTGGTCCAATCACTACATGGTGTATTCAAGGTCAAGAACACCA
CGACTTTGCAACAACACCTCATTGATGGGAGGGACATGATAATTATTCGCATGCCTAAGGATTTCCCACCATTTCCT
CAAAAGCTGAAATTTAGAGAGCCACAAAGGGAAGAGCGCATATGTCTTGTGACAACCAACTTCCAAACTAAGAGCAT
GTCTAGCATGGTGTCAGACACTAGTTGCACATTCCCTTCATCTGATGGCATATTCTGGAAGCATTGGATTCAAACCA
AGGATGGGCAGTGTGGCAGTCCATTAGTATCAACTAGAGATGGGTTCATTGTTGGTATACACTCAGCATCGAATTTC
ACCAACACAAACAATTATTTCACAAGCGTGCCGAAAAACTTCATGGAATTGTTGACAAATCAGGAGGCGCAGCAGTG
GGTTAGTGGTTGGCGATTAAATGCTGACTCAGTATTGTGGGGGGGCCATAAAGTTTTCATGGTGAAACCTGAAGAGC
CTTTTCAGCCAGTTAAGGAAGCGACTCAACTCATGAATTAG C. Amino acid sequence (SEQ ID NO:16)
MCRAISLRRLLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYYVDTKLDITSHN
EDYTIVEQYERSEGRHHLFLYGMDELYKKLFWALVVVAGVLFCYGLLVTVALCV<u>IWVRSGESLFKGPRDYNPISSTI</u>
CHLTNESDGHTTSLYGIGFGPFIITNKHLFRRNNGTLLVQSLHGVFKVKNTTTLQQHLIDGRDMIIIRMPKDFPPFP
QKLKFREPQREERICLVTTNFQTKSMSSMVSDTSCTFPSSDGIFWKHWIQTKDGQCGSPLVSTRDGFIVGIHSASNF
TNTNNYFTSVPKNFMELLTNQEAQQWVSGWRLNADSVLWGGHKVFMVKPEEPFQPVKEATQLMN

FIG. 15

A. CD4_PCS-OX_tTA

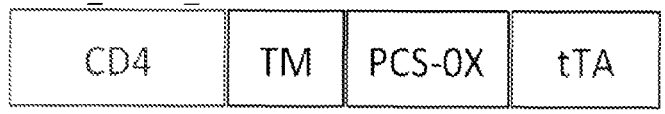

B. Nucleotide sequence (SEQ ID NO:17)
ATGTGCCGAGCCATCTCTCTTAGGCGCTTGCTGCTGCTGCTGCTGCAGCTGTCACAACTCCTAGCTGTCACTCAAGG
GAAGACGCTGGTGCTGGGGAAGGAAGGGGAATCAGCAGAACTGCCCTGCGAGAGTTCCCAGAAGAAGATCACAGTCT
TCACCTGGAAGTTCTCTGACCAGAGGAAGATTCTGGGGCAGCATGGCAAAGGTGTATTAATTAGAGGAGGTTCGCCT
TCGCAGTTTGATCGTTTTGATTCCAAAAAAGGGGCATGGGAGAAAGGATCGTTTCCTCTCATCATCAATAAACTTAA
GATGGAAGACTCTCAGACTTATATCTGTGAGCTGGAGAACAGGAAAGAGGAGGTGGAGTTGTGGGTGTTCAAAGTGA
CCTTCAGTCCGGGTACCAGCCTGTTGCAAGGGCAGAGCCTGACCCTGACCTTGGATAGCAACTCTAAGGTCTCTAAC
CCCTTGACAGAGTGCAAACACAAAAAGGGTAAAGTTGTCAGTGGTTCCAAAGTTCTCTCCATGTCCAACCTAAGGGT
TCAGGACAGCGACTTCTGGAACTGCACCGTGACCCTGGACCAGAAAAAGAACTGGTTCGGCATGACACTCTCAGTGC
TGGGTTTTCAGAGCACAGCTATCACGGCCTATAAGAGTGAGGGAGAGTCAGCGGAGTTCTCCTTCCCACTCAACTTT
GCAGAGGAAAACGGGTGGGGAGAGCTGATGTGGAAGGCAGAGAAGGATTCTTTCTTCCAGCCCTGGATCTCCTTCTC
CATAAAGAACAAAGAGGTGTCCGTACAAAAGTCCACCAAAGACCTCAAGCTCCAGCTGAAGGAAACGCTCCCACTCA
CCCTCAAGATACCCCAGGTCTCGCTTCAGTTTGCTGGTTCTGCAACCTGACTCTGACTCTGGACAAAGGGACACTG
CATCAGGAAGTGAACCTGGTGGTGATGAAAGTGGCTCAGCTCAACAATACTTTGACCTGTGAGGTGATGGGACCTAC
CTCTCCCAAGATGAGACTGACCCTGAAGCAGGAGAACCAGGAGGCCAGGGTCTCTGAGGAGCAGAAAGTAGTTCAAG
TGGTGGCCCCTGAGACAGGGCTGTGGCAGTGTCTACTGAGTGAAGGTGATAAGGTCAAGATGGACTCCAGGATCCAG
GTTTTATCCAGAGGGAAGCTTTTTGGGCACTGGTCGTGGTTGCTGGAGTCCTGTTTTGTTATGGCTTGCTAGTGAC
AGTGGCTCTTTGTGTTGAAAACCTGTATTTTCAGGGTATGTCTAGATTAGATAAAAGTAAAGTGATTAACAGCGCAT
TAGAGCTGCTTAATGAGGTCGGAATCGAAGGTTTAACAACCCGTAAACTCGCCCAGAAGCTAGGTGTAGAGCAGCCT
ACATTGTATTGGCATGTAAAAAATAAGCGGGCTTTGCTCGACGCCTTAGCCATTGAGATGTTAGATAGGCACCATAC
TCACTTTTGCCCTTTAGAAGGGGAAAGCTGGCAAGATTTTTTACGTAATAACGCTAAAAGTTTTAGATGTGCTTTAC
TAAGTCATCGCGATGGAGCAAAAGTACATTTAGGTACACGGCCTACAGAAAAACAGTATGAAACTCTCGAAAATCAA
TTAGCCTTTTTATGCCAACAAGGTTTTTCACTAGAGAATGCATTATATGCACTCAGCGCTGTGGGGCATTTTACTTT
AGGTTGCGTATTGGAAGATCAAGAGCATCAAGTCGCTAAAGAAGAAAGGGAAACACCTACTACTGATAGTATGCCGC
CATTATTACGACAAGCTATCGAATTATTTGATCACCAAGGTGCAGAGCCAGCCTTCTTATTCGGCCTTGAATTGATC
ATATGCGGATTAGAAAAACAACTTAAATGTGAAAGTGGGTCCGCGTACAGCCGCGCGCGTACGAAAAACAATTACGG
GTCTACCATCGAGGGCCTGCTCGATCTCCCGGACGACGACGCCCCCGAAGAGGCGGGGCTGGCGGCTCCGCGCCTGT
CCTTTCTCCCCGCGGGACACACGCGCAGACTGTCGACGGCCCCCCCGACCGATGTCAGCCTGGGGGACGAGCTCCAC
TTAGACGGCGAGGACGTGGCGATGGCGCATGCCGACGCGCTAGACGATTTCGATCTGGACATGTTGGGGGACGGGGA
TTCCCCGGGTCCGGGATTTACCCCCCACGACTCCGCCCCCTACGGCGCTCTGGATATGGCCGACTTCGAGTTTGAGC
AGATGTTTACCGATGCCCTTGGAATTGACGAGTACGGTGGGTAG

C. Amino acid sequence (SEQ ID NO:18)
MCRAISLRRLLLLLLQLSQLLAVTQGKTLVLGKEGESAELPCESSQKKITVFTWKFSDQRKILGQHGKGVLIRGGSP
SQFDRFDSKKGAWEKGSFPLIINKLKMEDSQTYICELENRKEEVELWVFKVTFSPGTSLLQGQSLTLTLDSNSKVSN
PLTECKHKKGKVVSGSKVLSMSNLRVQDSDFWNCTVTLDQKKNWFGMTLSVLGFQSTAITAYKSEGESAEFSFPLNF
AEENGWGELMWKAEKDSFFQPWISFSIKNKEVSVQKSTKDLKLQLKETLPLTLKIPQVSLQFAGSGNLTLTLDKGTL
HQEVNLVVMKVAQLNNTLTCEVMGPTSPKMRLTLKQENQEARVSEEQKVVQVVAPETGLWQCLLSEGDKVKMDSRIQ
VLSRGKLFWALVVVAGVLFCYGLLVTVALCVENLYFQXMSRLDKSKVINSALELLNEVGIEGLTTRKLAQKLGVEQP
TLYWHVKNKRALLDALAIEMLDRHHTHFCPLEGESWQDFLRNNAKSFRCALLSHRDGAKVHLGTRPTEKQYETLENQ
LAFLCQQGFSLENALYALSAVGHFTLGCVLEDQEHQVAKEERETPTTDSMPPLLRQAIELFDHQGAEPAFLFGLELI
ICGLEKQLKCESGSAYSRARTKNNYGSTIEGLLDLPDDDAPEEAGLAAPRLSFLPAGHTRRLSTAPPTDVSLGDELH
LDGEDVAMAHADALDDFDLDMLGDGDSPGPGFTPHDSAPYGALDMADFEFEQMFTDALGIDEYGG where X is either G, A, E, L, S, Y, or K.

FIG. 16

A. CD4_PCS-2X_tTA

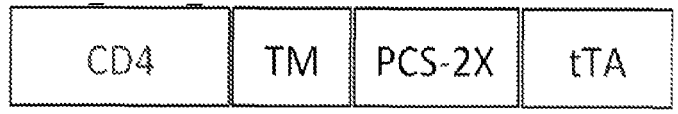

B. Nucleotide sequence (SEQ ID NO:19)

ATGTGCCGAGCCATCTCTCTTAGGCGCTTGCTGCTGCTGCTGCTGCAGCTGTCACAACTCCTAGCTGTCACTCAAGG
GAAGACGCTGGTGCTGGGGAAGGAAGGGGAATCAGCAGAACTGCCCTGCGAGAGTTCCCAGAAGAAGATCACAGTCT
TCACCTGGAAGTTCTCTGACCAGAGGAAGATTCTGGGGCAGCATGGCAAAGGTGTATTAATTAGAGGAGGTTCGCCT
TCGCAGTTTGATCGTTTTGATTCCAAAAAAGGGGCATGGGAGAAAGGATCGTTTCCTCTCATCATCAATAAACTTAA
GATGGAAGACTCTCAGACTTATATCTGTGAGCTGGAGAACAGGAAAGAGGAGGTGGAGTTGTGGGTGTTCAAAGTGA
CCTTCAGTCCGGGTACCAGCCTGTTGCAAGGGCAGAGCCTGACCCTGACCTTGGATAGCAACTCTAAGGTCTCTAAC
CCCTTGACAGAGTGCAAACACAAAAAGGGTAAAGTTGTCAGTGGTTCCAAAGTTCTCTCCATGTCCAACCTAAGGGT
TCAGGACAGCGACTTCTGGAACTGCACCGTGACCCTGGACCAGAAAAAGAACTGGTTCGGCATGACACTCTCAGTGC
TGGGTTTTCAGAGCACAGCTATCACGGCCTATAAGAGTGAGGGAGAGTCAGCGGAGTTCTCCTTCCCACTCAACTTT
GCAGAGGAAAACGGGTGGGGAGAGCTGATGTGGAAGGCAGAGAAGGATTCTTTCTTCCAGCCCTGGATCTCCTTCTC
CATAAAGAACAAAGAGGTGTCCGTACAAAAGTCCACCAAAGACCTCAAGCTCCAGCTGAAGGAAACGCTCCCACTCA
CCCTCAAGATACCCCAGGTCTCGCTTCAGTTTGCTGGTTCTGGCAACCTGACTCTGACTCTGGACAAAGGGACACTG
CATCAGGAAGTGAACCTGGTGGTGATGAAAGTGGCTCAGCTCAACAATACTTTGACCTGTGAGGTGATGGGACCTAC
CTCTCCCAAGATGAGACTGACCCTGAAGCAGGAGAACCAGGAGGCCAGGGTCTCTGAGGAGCAGAAAGTAGTTCAAG
TGGTGGCCCCTGAGACAGGGCTGTGGCAGTGTCTACTGAGTGAAGGTGATAAGGTCAAGATGGACTCCAGGATCCAG
GTTTTATCCAGAGGGAAGCTTTTTGGGCACTGGTCGTGGTTGCTGGAGTCCTGTTTTGTTATGGCTTGCTAGTGAC
AGTGGCTCTTTGTGTTATCTGGGTAAGATCTGGTGAAAACCTGTATTTTCAGGGTATGTCTAGATTAGATAAAAGTA
AAGTGATTAACAGCGCATTAGAGCTGCTTAATGAGGTCGGAATCGAAGGTTTAACAACCCGTAAACTCGCCCAGAAG
CTAGGTGTAGAGCAGCCTACATTGTATTGGCATGTAAAAAATAAGCGGGCTTTTGCTCGACGCCTTAGCCATTGAGAT
GTTAGATAGGCACCATACTCACTTTTGCCCTTTAGAAGGGGAAAGCTGGCAAGATTTTTTACGTAATAACGCTAAAA
GTTTTAGATGTGCTTTACTAAGTCATCGCGATGGAGCAAAAGTACATTTAGGTACACGGCCTACAGAAAAACAGTAT
GAAACTCTCGAAAATCAATTAGCCTTTTTATGCCAACAAGGTTTTTCACTAGAGAATGCATTATATGCACTCAGCGC
TGTGGGGCATTTTACTTTAGGTTGCGTATTGGAAGATCAAGAGCATCAAGTCGCTAAAGAAGAAAGGGAAACACCTA
CTACTGATAGTATGCCGCCATTATTACGACAAGCTATCGAATTATTTGATCACCAAGGTGCAGAGCCAGCCTTCTTA
TTCGGCCTTGAATTGATCATATGCGGATTAGAAAAACAACTTAAATGTGAAAGTGGGTCCCCGTACAGCCGCGCGCG
TACGAAAAACAATTACGGGTCTACCATCGAGGGCCTGCTCGATCTCCCGGACGACGACGCCCCCGAAGAGGCGGGGC
TGGCGGCTCCGCGCCTGTCCTTTCTCCCCGCGGGACACACGCGCAGACTGTCGACGGCCCCCCCGACCGATGTCAGC
CTGGGGGACGAGCTCCACTTAGACGGCGAGGACGTGGCGATGGCGCATGCCGACGCGCTAGACGATTTCGATCTGGA
CATGTTGGGGGACGGGGATTCCCCGGGTCCGGGATTTACCCCCCACGACTCCGCCCCCTACGGCGCTCTGGATATGG
CCGACTTCGAGTTTGAGCAGATGTTTACCGATGCCCTTGGAATTGACGAGTACGGTGGGTAG

C. Amino acid sequence (SEQ ID NO:20)

MCRAISLRRLLLLLLQLSQLLAVTQGKTLVLGKEGESAELPCESSQKKITVFTWKFSDQRKILGQHGKGVLIRGGSP
SQFDRFDSKKGAWEKGSFPLIINKLKMEDSQTYICELENRKEEVELWVFKVTFSPGTSLLQGQSLTLTLDSNSKVSN
PLTECKHKKGKVVSGSKVLSMSNLRVQDSDFWNCTVTLDQKKNWFGMTLSVLGFQSTAITAYKSEGESAEFSFPLNF
AEENGWGELMWKAEKDSFFQPWISFSIKNKEVSVQKSTKDLKLQLKETLPLTLKIPQVSLQFAGSGNLTLTLDKGTL
HQEVNLVVMKVAQLNNTLTCEVMGPTSPKMRLTLKQENQEARVSEEQKVVQVVAPETGLWQCLLSEGDKVKMDSRIQ
VLSRGKLFWALVVVAGVLFCYGLLVTVALCV*MVRSG*ENLYFQXMSRLDKSKVINSALELLNEVGIEGLTTRKLAQK
LGVEQPTLYWHVKNKRALLDALAIEMLDRHHTHFCPLEGESWQDFLRNNAKSFRCALLSHRDGAKVHLGTRPTEKQY
ETLENQLAFLCQQGFSLENALYALSAVGHFTLGCVLEDQEHQVAKEERETPTTDSMPPLLRQAIELFDHQGAEPAFL
FGLELIICGLEKQLKCESGSAYSRARTKNNYGSTIEGLLDLPDDDAPEEAGLAAPRLSFLPAGHTRRLSTAPPTDVS
LGDELHLDGEDVAMAHADALDDFDLDMLGDGDSPGPGFTPHDSAPYGALDMADFEFEQMFTDALGIDEYGG where X is either G, A, E, L, S, Y, or K.

FIG. 17

A. CD4 ISP-0 TEV

B. Nucleotide sequence (SEQ ID NO:21)
ATGTGCCGAGCCATCTCTCTTAGGCGCTTGCTGCTGCTGCTGCTGCAGCTGTCACAACTCCTAGCTGTCACTCAAGG
GAAGACGCTGGTGCTGGGGAAGGAAGGGGAATCAGCAGAACTGCCCTGCGAGAGTTCCCAGAAGAAGATCACAGTCT
TCACCTGGAAGTTCTCTGACCAGAGGAAGATTCTGGGGCAGCATGGCAAAGGTGTATTAATTAGAGGAGGTTCGCCT
TCGCAGTTTGATCGTTTTGATTCCAAAAAAGGGGCATGGGAGAAAGGATCGTTTCCTCTCATCATCAATAAACTTAA
GATGGAAGACTCTCAGACTTATATCTGTGAGCTGGAGAACAGGAAAGAGGAGGTGGAGTTGTGGGTGTTCAAAGTGA
CCTTCAGTCCGGGTACCAGCCTGTTGCAAGGGCAGAGCCTGACCCTGACCTTGGATAGCAACTCTAAGGTCTCTAAC
CCCTTGACAGAGTGCAAACACAAAAAGGGTAAAGTTGTCAGTGGTTCCAAAGTTCTCTCCATGTCCAACCTAAGGGT
TCAGGACAGCGACTTCTGGAACTGCACCGTGACCCTGGACCAGAAAAAGAACTGGTTCGGCATGACACTCTCAGTGC
TGGGTTTTCAGAGCACAGCTATCACGGCCTATAAGAGTGAGGGAGAGTCAGCGGAGTTCTCCTTCCCACTCAACTTT
GCAGAGGAAAACGGGTGGGGAGAGCTGATGTGGAAGGCAGAGAAGGATTCTTTCTTCCAGCCCTGGATCTCCTTCTC
CATAAAGAACAAAGAGGTGTCCGTACAAAAGTCCACCAAAGACCTCAAGCTCCAGCTGAAGGAAACGCTCCCACTCA
CCCTCAAGATACCCCAGGTCTCGCTTCAGTTTGCTGGTTCTGGCAACCTGACTCTGACTCTGGACAAAGGGACACTG
CATCAGGAAGTGAACCTGGTGGTGATGAAAGTGGCTCAGCTCAACAATACTTTGACCTGTGAGGTGATGGGACCTAC
CTCTCCCAAGATGAGACTGACCCTGAAGCAGGAGAACCAGGAGGCCAGGGTCTCTGAGGAGCAGAAAGTAGTTCAAG
TGGTGGCCCCTGAGACAGGGCTGTGGCAGTGTCTACTGAGTGAAGGTGATAAGGTCAAGATGGACTCCAGGATCCAG
GTTTTATCCAGAGGGAAGCTTTTTGGGCACTGGTCGTGGTTGCTGGAGTCCTGTTTTGTTATGGCTTGCTAGTGAC
AGTGGCTCTTTGTGTTGAGAGCTTGTTTAAGGGGCCGCGTGATTACAACCCGATATCGAGCACCATTTGTCATTTGA
CGAATGAATCTGATGGGCACACAACATCGTTGTATGGTATTGGATTTGGTCCCTTCATCATTACAAACAAGCACTTG
TTTAGAAGAAATAATGGAACACTGTTGGTCCAATCACTACATGGTGTATTCAAGGTCAAGAACACCACGACTTTGCA
ACAACACCTCATTGATGGAGGGACATGATAATTATTCGCATGCCTAAGGATTTCCCACCATTTCCTCAAAAGCTGA
AATTTAGAGAGCCACAAAGGGAAGAGCGCATATGTCTTGTGACAACCAACTTCCAAACTAAGAGCATGTCTAGCATG
GTGTCAGACACTAGTTGCACATTCCCTTCATCTGATGGCATATTCTGGAAGCATTGGATTCAAACCAAGGATGGGCA
GTGTGGCAGTCCATTAGTATCAACTAGAGATGGGTTCATTGTTGGTATACACTCAGCATCGAATTTCACCAACACAA
ACAATTATTTCACAAGCGTGCCGAAAAACTTCATGGAATTGTTGACAAATCAGGAGGCGCAGCAGTGGGTTAGTGGT
TGGCGATTAAATGCTGACTCAGTATTGTGGGGGGGCCATAAAGTTTTCATGGTGAAACCTGAAGAGCCTTTTCAGCC
AGTTAAGGAAGCGACTCAACTCATGAATTAG C. Amino acid sequence (SEQ ID NO:22)
MCRAISLRRLLLLLLQLSQLLAVTQGKTLVLGKEGESAELPCESSQKKITVFTWKFSDQRKILGQHGKGVLIRGGSP
SQFDRFDSKKGAWEKGSFPLIINKLKMEDSQTYICELENRKEEVELWVFKVTFSPGTSLLQGQSLTLTLDSNSKVSN
PLTECKHKKGKVVSGSKVLSMSNLRVQDSDFWNCTVTLDQKKNWFGMTLSVLGFQSTAITAYKSEGESAEFSFPLNF
AEENGWGELMWKAEKDSFFQPWISFSIKNKEVSVQKSTKDLKLQLKETLPLTLKIPQVSLQFAGSGNLTLTLDKGTL
HQEVNLVVMKVAQLNNTLTCEVMGPTSPKMRLTLKQENQEARVSEEQKVVQVVAPETGLWQCLLSEGDKVKMDSRIQ
VLSRGKLFWALVVVAGVLFCYGLLVTVALCVESLFKGPRDYNPISSTICHLTNESDGHTTSLYGIGFGPFIITNKHL
FRRNNGTLLVQSLHGVFKVKNTTTLQQHLIDGRDMIIIRMPKDFPPFPQKLKFREPQREERICLVTTNFQTKSMSSM
VSDTSCTFPSSDGIFWKHWIQTKDGQCGSPLVSTRDGFIVGIHSASNFTNTNNYFTSVPKNFMELLTNQEAQQWVSG
WRLNADSVLWGGHKVFMVKPEEPFQPVKEATQLMN

FIG. 18

A. CD4 ISP-2 TEV

B. Nucleotide sequence (SEQ ID NO:23)
ATGTGCCGAGCCATCTCTCTTAGGCGCTTGCTGCTGCTGCTGCTGCAGCTGTCACAACTCCTAGCTGTCACTCAAGG
GAAGACGCTGGTGCTGGGGAAGGAAGGGGAATCAGCAGAACTGCCCTGCGAGAGTTCCCAGAAGAAGATCACAGTCT
TCACCTGGAAGTTCTCTGACCAGAGGAAGATTCTGGGGCAGCATGGCAAAGGTGTATTAATTAGAGGAGGTTCGCCT
TCGCAGTTTGATCGTTTTGATTCCAAAAAAGGGGCATGGGAGAAAGGATCGTTTCCTCTCATCATCAATAAACTTAA
GATGGAAGACTCTCAGACTTATATCTGTGAGCTGGAGAACAGGAAAGAGGAGGTGGAGTTGTGGGTGTTCAAAGTGA
CCTTCAGTCCGGGTACCAGCCTGTTGCAAGGGCAGAGCCTGACCCTGACCTTGGATAGCAACTCTAAGGTCTCTAAC
CCCTTGACAGAGTGCAAACACAAAAAGGGTAAAGTTGTCAGTGGTTCCAAAGTTCTCTCCATGTCCAACCTAAGGGT
TCAGGACAGCGACTTCTGGAACTGCACCGTGACCCTGGACCAGAAAAAGAACTGGTTCGGCATGACACTCTCAGTGC
TGGGTTTTCAGAGCACAGCTATCACGGCCTATAAGAGTGAGGGAGAGTCAGCGGAGTTCTCCTTCCCACTCAACTTT
GCAGAGGAAAACGGGTGGGGAGAGCTGATGTGGAAGGCAGAGAAGGATTCTTTCTTCCAGCCCTGGATCTCCTTCTC
CATAAAGAACAAAGAGGTGTCCGTACAAAAGTCCACCAAAGACCTCAAGCTCCAGCTGAAGGAAACGCTCCCACTCA
CCCTCAAGATACCCCAGGTCTCGCTTCAGTTTGCTGGTTCTGGCAACCTGACTCTGACTCTGGACAAAGGGACACTG
CATCAGGAAGTGAACCTGGTGGTGATGAAAGTGGCTCAGCTCAACAATACTTTGACCTGTGAGGTGATGGGACCTAC
CTCTCCCAAGATGAGACTGACCCTGAAGCAGGAGAACCAGGAGGCCAGGGTCTCTGAGGAGCAGAAAGTAGTTCAAG
TGGTGGCCCCTGAGACAGGGCTGTGGCAGTGTCTACTGAGTGAAGGTGATAAGGTCAAGATGGACTCCAGGATCCAG
GTTTTATCCAGAGGGAAGCTTTTTGGGCACTGGTCGTGGTTGCTGGAGTCCTGTTTTGTTATGGCTTGCTAGTGAC
AGTGGCTCTTTGTGTTATCTGGGTAAGATCGGTGAGAGCTTGTTTAAGGGGCCGCGTGATTACAACCCGATATCGA
GCACCATTTGTCATTTGACGAATGAATCTGATGGGCACACAACATCGTTGTATGGTATTGGATTTGGTCCCTTCATC
ATTACAAACAAGCACTTGTTTAGAAGAAATAATGGAACACTGTTGGTCCAATCACTACATGGTGTATTCAAGGTCAA
GAACACCACGACTTTGCAACAACACCTCATTGATGGGAGGGACATGATAATTATTCGCATGCCTAAGGATTTCCCAC
CATTTCCTCAAAAGCTGAAATTTAGAGAGCCACAAAGGGAAGAGCGCATATGTCTTGTGACAACCAACTTCCAAACT
AAGAGCATGTCTAGCATGGTGTCAGACACTAGTTGCACATTCCCTTCATCTGATGGCATATTCTGGAAGCATTGGAT
TCAAACCAAGGATGGGCAGTGTGGCAGTCCATTAGTATCAACTAGAGATGGGTTCATTGTTGGTATACACTCAGCAT
CGAATTTCACCAACACAAACAATTATTTCACAAGCGTGCCGAAAAACTTCATGGAATTGTTGACAAATCAGGAGGCG
CAGCAGTGGGTTAGTGGTTGGCGATTAAATGCTGACTCAGTATTGTGGGGGGGCCATAAAGTTTTCATGGTGAAACC
TGAAGAGCCTTTTCAGCCAGTTAAGGAAGCGACTCAACTCATGAATTAG

C. Amino acid sequence (SEQ ID NO:24)
MCRAISLRRLLLLLQLSQLLAVTQGKTLVLGKEGESAELPCESSQKKITVFTWKFSDQRKILGQHGKGVLIRGGSP
SQFDRFDSKKGAWEKGSFPLIINKLKMEDSQTYICELENRKEEVELWVFKVTFSPGTSLLQGQSLTLTLDSNSKVSN
PLTECKHKKGKVVSGSKVLSMSNLRVQDSDFWNCTVTLDQKKNWFGMTLSVLGFQSTAITAYKSEGESAEFSFPLNF
AEENGWGELMWKAEKDSFFQPWISFSIKNKEVSVQKSTKDLKLQLKETLPLTLKIPQVSLQFAGSGNLTLTLDKGTL
HQEVNLVVMKVAQLNNTLTCEVMGPTSPKMRLTLKQENQEARVSEEQKVVQVVAPETGLWQCLLSEGDKVKMDSRIQ
VLSRGKLFWALVVVAGVLFCYGLLVTVALCV<u>IWVRSGESLFKGPRDYNPISSTI</u>CHLTNESDGHTTSLYGIGFGPFI
ITNKHLFRRNNGTLLVQSLHGVFKVKNTTTLQQHLIDGRDMIIIRMPKDFPPFPQKLKFREPQREERICLVTTNFQT
KSMSSMVSDTSCTFPSSDGIFWKHWIQTKDGQCGSPLVSTRDGFIVGIHSASNFTNTNNYFTSVPKNFMELLTNQEA
QQWVSGWRLNADSVLWGGHKVFMVKPEEPFQPVKEATQLMN

FIG. 19

A. mCherry_PCS-OX_tTA-BFP

| mCherry | TM | PCS-OX | tTA-BFP |

B. Nucleotide sequence (SEQ ID NO:25)

ATGTGCCGAGCCATCTCTCTTAGGCGCTTGCTGCTGCTGCTGCTGCAGCTGTCACAACTCCTAGCTGTCACTCAAGGGATGGTGAG
CAAGGGCGAGGAGGATAACATGGCCATCATCAAGGAGTTCATGCGCTTCAAGGTGCACATGGAGGGCTCCGTGAACGGCCACGAGT
TCGAGATCGAGGGCGAGGGCGAGGGCCGCCCCTACGAGGGCACCCAGACCGCCAAGCTGAAGGTGACCAAGGGTGGCCCCCTGCCC
TTCGCCTGGGACATCCTGTCCCCTCAGTTCATGTACGGCTCCAAGGCCTACGTGAAGCACCCCGCCGACATCCCCGACTACTTGAA
GCTGTCCTTCCCCGAGGGCTTCAAGTGGGAGCGCGTCATGAACTTCGAGGACGGCGGCGTGGTGACCGTGACCCAGGACTCCTCCC
TGCAGGACGGCGAGTTCATCTACAAGGTGAAGCTGCGCGGCACCAACTTCCCCTCCGACGGCCCCGTAATGCAGAAGAAGACCATG
GGCTGGGAGGCCTCCTCCGAGCGGATGTACCCCGAGGACGGCGCCCTGAAGGGCGAGATCAAGCAGAGGCTGAAGCTGAAGGACGG
CGGCCACTACGACGCTGAGGTCAAGACCACCTACAACGCCAAGAAGCCCGTGCAGCTGCCCGGCGCCTACAACGTCAACATCAAGT
TGGACATCACCTCCCACAACGAGGACTACACCATCGTGGAACAGTACGAACGCGCCGAGGGCCGCCACTCCACCGGCGGCATGGAC
GAGCTGTACAAGAAGCTTTTTTGGGCACTGGTCGTGGTTGCTGGAGTCCTGTTTTGTTATGGCTTGCTAGTGACAGTGGCTCTTTG
TGTTGAAAACCTGTATTTTCAGGGTATGTCTAGATTAGATAAAAGTAAAGTGATTAACAGCGCATTAGAGCTGCTTAATGAGGTCG
GAATCGAAGGTTTAACAACCCGTAAACTCGCCCAGAAGCTAGGTGTAGAGCAGCCTACATTGTATTGGCATGTAAAAAATAAGCGG
GCTTTGCTCGACGCCTTAGCCATTGAGATGTTAGATAGGCACCATACTCACTTTTGCCCTTTAGAAGGGGAAAGCTGGCAAGATTT
TTTACGTAATAACGCTAAAAGTTTTAGATGTGCTTTACTAAGTCATCGCGATGGAGCAAAAGTACATTTAGGTACACGGCCTACAG
AAAAACAGTATGAAACTCTCGAAAATCAATTAGCCTTTTTATGCCAACAAGGTTTTTCACTAGAGAATGCATTATATGCACTCAGC
GCTGTGGGGCATTTTACTTTAGGTTGCGTATTGGAAGATCAAGAGCATCAAGTCGCTAAAGAAGAAAGGGAAACACCTACTACTGA
TAGTATGCCGCCATTATTACGACAAGCTATCGAATTATTTGATCACCAAGGTGCAGAGCCAGCCTTCTTATTCGGCCTTGAATTGA
TCATATGCGGATTAGAAAAACAACTTAAATGTGAAAGTGGGTCCGCGTACAGCCGCGCGTACGAAAAACAATTACGGGTCTACC
ATCGAGGGCCTGCTCGATCTCCCGGACGACGACGCCCCCGAAGAGGCGGGGCTGGCGGCTCCGCGCCTGTCCTTTCTCCCCGCGGG
ACACACGCGCAGACTGTCGACGGCCCCCCCGACCGATGTCAGCCTGGGGGACGAGCTCCACTTAGACGGCGAGGACGTGGCGATGG
CGCATGCCGACGCGCTAGACGATTTCGATCTGGACATGTTGGGGGACGGGGATTCCCCGGGTCCGGGATTTACCCCCCACGACTCC
GCCCCCTACGGCGCTCTGGATATGGCCGACTTCGAGTTTGAGCAGATGTTTACCGATGCCCTTGGAATTGACGAGTACGGTGGAGG
TACCGGCGGAGGCTCCGGTGGCTCTATGGTGAGCAAGGGCGAGGAGCTGTTCACCGGGGTGGTGCCCATCCTGGTCGAGCTGG
ACGGCGACGTAAACGGCCACAAGTTCAGCGTGAGGGCGAGGGCGAGGGCGATGCCACCAACGGCAAGCTGACCCTGAAGTTCATC
TGCACCACCGGCAAGCTGCCCGTGCCCTGGCCCACCCTCGTGACCACCCTGAGCCACGGCGTGCAGTGCTTCGCCCGCTACCCCGA
CCACATGAAGCAGCACGACTTCTTCAAGTCCGCCATGCCCGAAGGCTACGTCCAGGAGCGCACCATCTTCTTCAAGGACGACGGCA
CCTACAAGACCCGCGCCGAGGTGAAGTTCGAGGGCGACACCCTAGTGAACCGCATCGAGCTGAAGGGCGTCGACTTCAAGGAGGAC
GGCAACATCCTGGGGCACAAGCTGGAGTACAACTTCAACAGCCACAACATCTATATCATGGCCGTCAAGCAGAAGAACGGCATCAA
GGTGAACTTCAAGATCCGCCACAACGTGGAGGACGGCAGCGTGCAGCTCGCCGACCACTACCAGCAGAACACCCCCATCGGCGACG
GCCCCGTGCTGCTGCCCGACAGCCACTACCTGAGCACCCAGTCCGTGCTGAGCAAAGACCCCAACGAGAAGCGCGATCACATGGTC
CTGCTGGAGTTCGCACCGCCGCCGGGATCACTCTCGGCATGGACGAGCTGTACAAGTAA

C. Amino acid sequence (SEQ ID NO:26)

MCRAISLRRLLLLLLQLSQLLAVTQCMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCVENLYFQXMSRLDKSKVINSA
LELLNEVGIEGLTTRKLAQKLGVEQPTLYWHVKNKRALLDALAIEMLDRHHTHFCPLEGESWQDFLRNNAKSFRCAL
LSHRDGAKVHLGTRPTEKQYETLENQLAFLCQQGFSLENALYALSAVGHFTLGCVLEDQEHQVAKEERETPTTDSMP
PLLRQAIELFDHQGAEPAFLFGLELIICGLEKQLKCESGSAYSRARTKNNYGSTIEGLLDLPDDDAPEEAGLAAPRL
SFLPAGHTRRLSTAPPTDVSLGDELHLDGEDVAMAHADALDDFDLDMLGDGDSPGPGFTPHDSAPYGALDMADFEFE
QMFTDALGIDEYGGGTGGGSGGGSMVSKGEELFTGVVPILVELDGDVNGHKFSVRGEGEGDATNGKLTLKFICTTGK
LPVPWPTLVTTLSHGVQCFARYPDHMKQHDFFKSAMPEGYVQERTIFFKDDGTYKTRAEVKFEGDTLVNRIELKGVD
FKEDGNILGHKLEYNFNSHNIYIMAVKQKNGIKVNFKIRHNVEDGSVQLADHYQQNTPIGDPVLLPDSHYLSTQSV
LSKDPNEKRDHMVLLEFRTAAGITLGMDELYK where X is either G, A, E, L, S, Y, or K.

FIG. 20

A. mCherry_ISP-0_TEV-AI

B. Nucleotide sequence    (SEQ ID NO:27)
ATGTGCCGAGCCATCTCTCTTAGGCGCTTGCTGCTGCTGCTGCTGCAGCTGTCACAACTCCTAGCTGTCACTCAAGG
GATGGTGAGCAAGGGCGAGGAGGATAACATGGCCATCATCAAGGAGTTCATGCGCTTCAAGGTGCACATGGAGGGCT
CCGTGAACGGCCACGAGTTCGAGATCGAGGGCGAGGGCGAGGGCCGCCCCTACGAGGGCACCCAGACCGCCAAGCTG
AAGGTGACCAAGGGTGGCCCCCTGCCCTTCGCCTGGGACATCCTGTCCCCTCAGTTCATGTACGGCTCCAAGGCCTA
CGTGAAGCACCCCGCCGACATCCCCGACTACTTGAAGCTGTCCTTCCCCGAGGGCTTCAAGTGGGAGCGCGTGATGA
ACTTCGAGGACGGCGGCGTGGTGACCGTGACCCAGGACTCCTCCCTGCAGGACGGCGAGTTCATCTACAAGGTGAAG
CTGCGCGGCACCAACTTCCCCTCCGACGGCCCCGTAATGCAGAAGAAGACCATGGGCTGGGAGGCCTCCTCCGAGCG
GATGTACCCCGAGGACGGCGCCCTGAAGGGCGAGATCAAGCAGAGGCTGAAGCTGAAGGACGGCGGCCACTACGACG
CTGAGGTCAAGACCACCTACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCGCCACTCCACCGGCGGCAT
GGACGAGCTGTACAAGAAGCTTTTTGGGCACTGGTCGTGGTTGCTGGAGTCCTGTTTTGTTATGGCTTGCTAGTGA
CAGTGGCTCTTTGTGTTGAGAGCTTGTTTAAGGGGCCGCGTGATTACAACCCGATATCGAGCACCATTTGTCATTTG
ACGAATGAATCTGATGGGCACACAACATCGTTGTATGGTATTGGATTTGGTCCCTTCATCATTACAAACAAGCACTT
GTTTAGAAGAAATAATGGAACACTGTTGGTCCAATCACTACATGGTGTATTCAAGGTCAAGAACACCACGACTTTGC
AACAACACCTCATTGATGGGAGGGACATGATAATTATTCGCATGCCTAAGGATTTCCCACCATTTCCTCAAAAGCTG
AAATTTAGAGAGCCACAAAGGGAAGAGCGCATATGTCTTGTGACAACCAACTTCCAAACTAAGAGCATGTCTAGCAT
GGTGTCAGACACTAGTTGCACATTCCCTTCATCTGATGGCATATTCTGGAAGCATTGGATTCAAACCAAGGATGGGC
AGTGTGGCAGTCCATTAGTATCAACTAGAGATGGGTTCATTGTTGGTATACACTCAGCATCGAATTTCACCAACACA
AACAATTATTTCACAAGCGTGCCGAAAAACTTCATGGAATTGTTGACAAATCAGGAGGCGCAGCAGTGGGTTAGTGG
TTGGCGATTAAATGCTGACTCAGTATTGTGGGGGGGCCATAAAGTTTTCATGTAG

C. Amino acid sequence   (SEQ ID NO:28)
MCRAISLRRLLLLLQLSQLLAVTQGMVSKGEEDNMAIIKEFMRFKVHMEGSVNGHEFEIEGEGEGRPYEGTQTAKL
KVTKGGPLPFAWDILSPQFMYGSKAYVKHPADIPDYLKLSFPEGFKWERVMNFEDGGVVTVTQDSSLQDGEFIYKVK
LRGTNFPSDGPVMQKKTMGWEASSERMYPEDGALKGEIKQRLKLKDGGHYDAEVKTTYKAKKPVQLPGAYNVNIKLD
ITSHNEDYTIVEQYERAEGRHSTGGMDELYKKLFWALVVVAGVLFCYGLLVTVALCVESLFKGPRDYNPISSTICHL
TNESDGHTTSLYGIGFGPFIITNKHLFRRNNGTLLVQSLHGVFKVKNTTTLQQHLIDGRDMIIIRMPKDFPPFPQKL
KFREPQREERICLVTTNFQTKSMSSMVSDTSCTFPSSDGIFWKHWIQTKDGQCGSPLVSTRDGFIVGIHSASNFTNT
NNYFTSVPKNFMELLTNQEAQQWVSGWRLNADSVLWGGHKVFM

FIG. 21

A. dTomato_PCS-OX_tTA-BFP

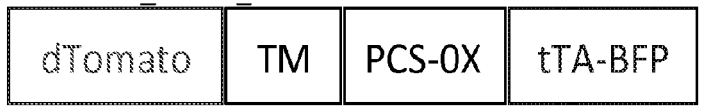

B. Nucleotide sequence  (SEQ ID NO:29)
ATGTGCCGAGCCATCTCTCTTAGGCGCTTGCTGCTGCTGCTGCAGCTGTCACAACTCCTAGCTGTCACTCAAGGGGTGAGCAA
GGGCGAGGAGGTCATCAAAGAGTTCATGCGCTTCAAGGTGCGCATGGAGGGCTCCATGAACGGCCACGAGTTCGAGATCGAGGGCG
AGGGCGAGGGCCGCCCCTACGAGGGCACCCAGACCGCCAAGCTGAAGGTGACCAAGGGCGGCCCCCTGCCCTTCGCCTGGGACATC
CTGTCCCCCCAGTTCATGTACGGCTCCAAGGCGTACGTGAAGCACCCCGCCGACATCCCCGATTACAAGAAGCTGTCCTTCCCCGA
GGGCTTCAAGTGGGAGCGCGTGATGAACTTCGAGGACGGCGGTCTGGTGACCGTGACCCAGGACTCCTCCCTGCAGGACGGCACGC
TGATCTACAAGGTGAAGATGCGCGGCACCAACTTCCCCCCCGACGGCCCCGTAATGCAGAAGAAGACCATGGGCTGGGAGGCCTCC
ACCGAGCGCCTGTACCCCCGCGACGGCGTGCTGAAGGGCGAGATCCACCAGGCCCTGAAGCTGAAGGACGGCGGCCACTACCTGGT
GGAGTTCAAGACCATCTACATGGCCAAGAAGCCCGTGCAACTGCCCGGCTACTACGTGGACACCAAGCTGGACATCACCTCCC
ACAACGAGGACTACACCATCGTGGAACAGTACGAGCGCTCCGAGGGCCGCCACCACCTGTTCCTGTACGGCATGGACGAGCTGTAC
AAGAAGCTTTTTTGGGCACTGGTCGTGGTTGCTGGAGTCCTGTTTTGTTATGGCTTGCTAGTGACAGTGGCTCTTTGTGTTGAAAA
CCTGTATTTTCAGGGTATGTCTAGATTAGATAAAAGTAAAGTGATTAACAGCGCATTAGAGCTGCTTAATGAGGTCGGAATCGAAG
GTTTAACAACCCGTAAACTCGCCCAGAAGCTAGGTGTAGAGCAGCCTACATTGTATTGGCATGTAAAAAATAAGCGGGCTTTGCTC
GACGCCTTAGCCATTGAGATGTTAGATAGGCACCATACTCACTTTTGCCCTTTAGAAGGGGAAAGCTGGCAAGATTTTTTACGTAA
TAACGCTAAAAGTTTTAGATGTGCTTTACTAAGTCATCGCGATGGAGCAAAAGTACATTTAGGTACACGGCCTACAGAAAAACAGT
ATGAAACTCTCGAAAATCAATTAGCCTTTTTATGCCAACAAGGTTTTTCACTAGAGAATGCATTATATGCACTCAGCGCTGTGGGG
CATTTTACTTTAGGTTGCGTATTGGAAGATCAAGAGCATCAAGTCGCTAAAGAAGAAAGGGAAACACCTACTACTGATAGTATGCC
GCCATTATTACGACAAGCTATCGAATTATTTGATCACCAAGGTGCAGAGCCAGCCTTCTTATTCGGCCTTGAATTGATCATATGCG
GATTAGAAAAACAACTTAAATGTGAAAGTGGGTCCGCGTACAGCCGCGCGCGTACGAAAAACAATTACGGGTCTACCATCGAGGGC
CTGCTCGATCTCCCGGACGACGACGCCCCCGAAGAGGCGGGGCTGGCGGCTCCGCGCCTGTCCTTTCTCCCGCGGGACACACGCG
CAGACTGTCGACGGCCCCCCCGACCGATGTCAGCCTGGGGGACGAGCTCCACTTAGACGGCGAGGACGTGGCGATGGCGCATGCCG
ACGCGCTAGACGATTTCGATCTGGACATGTTGGGGGACGGGGATTCCCCGGGTCCGGGATTTACCCCCCACGACTCCGCCCCCTAC
GGCGCTCTGGATATGGCCGACTTCGAGTTTGAGCAGATGTTTACCGATGCCCTTGAATGACGAGTACGGTGGAGGTACCGGCGG
AGGCTCCGGTGGTGGCTCTATGGTGAGCAAGGGCGAGGAGCTGTTCACCGGGGTGGTGCCCATCCTGGTCGAGCTGGACGGCGACG
TAAACGGCCACAAGTTCAGCGTGCGAGGGGCGAGGGCGAGGACGGCGATGCCAACGGCAAGCTGACCCTGAAGTTCATCTGCACCACC
GGCAAGCTGCCCGTGCCCTGGCCCACCCTCGTGACCACCCTGAGCCACGGCGTGCAGTGCTTCGCCCGCTACCCCGACCACATGAA
GCAGCACGACTTCTTCAAGTCCGCCATGCCCGAAGGCTACGTCCAGGAGCGCACCATCTTCTTCAAGGACGACGGCACCTACAAGA
CCCGCGCCGAGGTGAAGTTCGAGGGCGACACCCTAGTGAACCGCATCGAGCTGAAGGGCGTCGACTTCAAGGAGGACGGCAACATC
CTGGGGCACAAGCTGGAGTACAACTTCAACAGCCACAACATCTATATCATGGCCGTCAAGCAGAAGAACGGCATCAAGGTGAACTT
CAAGATCCGCCACAACGTGGAGGACGGCAGCGTGCAGCTCGCCGACCACTACCAGCAGAACACCCCCATCGGCGACGGCCCCGTGC
TGCTGCCCGACAGCCACTACCTGAGCACCCAGTCCGTGCTGAGCAAAGACCCCAACGAGAAGCGCGATCACATGGTCCTGCTGGAG
TTCCGCACCGCCGCCGGGATCACTCTCGGCATGGACGAGCTGTACAAGTAA C. Amino acid sequence  (SEQ ID NO:30)
MCRAISLRRLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYVDTKLDITSHN
EDYTIVEQYERSEGRHHLFLYGMDELYKKLFWALVVVAGVLFCYGLLVTVALC<u>VENLYFQ</u>XMSRLDKSKVINSALEL
LNEVGIEGLTTRKLAQKLGVEQPTLYWHVKNKRALLDALAIEMLDRHHTHFCPLEGESWQDFLRNNAKSFRCALLSH
RDGAKVHLGTRPTEKQYETLENQLAFLCQQGFSLENALYALSAVGHFTLGCVLEDQEHQVAKEERETPTTDSMPPLL
RQAIELFDHQGAEPAFLFGLELIICGLEKQLKCESGSAYSRARTKNNYGSTIEGLLDLPDDDAPEEAGLAAPRLSFL
PAGHTRRLSTAPPTDVSLGDELHLDGEDVAMAHADALDDFDLDMLGDGDSPGPGFTPHDSAPYGALDMADFEFEQMF
TDALGIDEYGGGTGGGSGGGSMVSKGEELFTGVVPILVELDGDVNGHKFSVRGEGEGDATNGKLTLKFICTTGKLPV
PWPTLVTTLSHGVQCFARYPDHMKQHDFFKSAMPEGYVQERTIFFKDDGTYKTRAEVKFEGDTLVNRIELKGVDFKE
DGNILGHKLEYNFNSHNIYIMAVKQKNGIKVNFKIRHNVEDGSVQLADHYQQNTPIGDGPVLLPDSHYLSTQSVLSK
DPNEKRDHMVLLEFRTAAGITLGMDELYK where X is either G, A, E, L, S, Y, or K.

FIG. 22

A. dTomato_ISP-0_TEV-AI

B. Nucleotide sequence   (SEQ ID NO:31)
ATGTGCCGAGCCATCTCTCTTAGGCGCTTGCTGCTGCTGCTGCTGCAGCTGTCACAACTCCTAGCTGTCACTCAAGG
GGTGAGCAAGGGCGAGGAGGTCATCAAAGAGTTCATGCGCTTCAAGGTGCGCATGGAGGGCTCCATGAACGGCCACG
AGTTCGAGATCGAGGGCGAGGGCGAGGGCCGCCCCTACGAGGGCACCCAGACCGCCAAGCTGAAGGTGACCAAGGGC
GGCCCCCTGCCCTTCGCCTGGGACATCCTGTCCCCCCAGTTCATGTACGGCTCCAAGGCGTACGTGAAGCACCCCGC
CGACATCCCCGATTACAAGAAGCTGTCCTTCCCCGAGGGCTTCAAGTGGGAGCGCGTGATGAACTTCGAGGACGGCG
GTCTGGTGACCGTGACCCAGGACTCCTCCCTGCAGGACGGCACGCTGATCTACAAGGTGAAGATGCGCGGCACCAAC
TTCCCCCCCGACGGCCCCGTAATGCAGAAGAAGACCATGGGCTGGGAGGCCTCCACCGAGCGCCTGTACCCCGCGA
CGGCGTGCTGAAGGGCGAGATCCACCAGGCCCTGAAGCTGAAGGACGGCGGCCACTACCTGGTGGAGTTCAAGACCA
TCTACATGGCCAAGAAGCCCGTGCAACTGCCCGGCTACTACTACGTGGACACCAAGCTGGACATCACCTCCCACAAC
GAGGACTACACCATCGTGGAACAGTACGAGCGCTCCGAGGGCCGCCACCACCTGTTCCTGTACGGCATGGACGAGCT
GTACAAGAAGCTTTTTTGGGCACTGGTCGTGGTTGCTGGAGTCCTGTTTTGTTATGGCTTGCTAGTGACAGTGGCTC
TTTGTGTTGAGAGCTTGTTTAAGGGGCCGCGTGATTACAACCCGATATCGAGCACCATTTGTCATTTGACGAATGAA
TCTGATGGGCACACAACATCGTTGTATGGTATTGGATTTGGTCCCTTCATCATTACAAACAAGCACTTGTTTAGAAG
AAATAATGGAACACTGTTGGTCCAATCACTACATGGTGTATTCAAGGTCAAGAACACCACGACTTTGCAACAACACC
TCATTGATGGGAGGGACATGATAATTATTCGCATGCCTAAGGATTTCCCACCATTTCCTCAAAAGCTGAAATTTAGA
GAGCCACAAAGGGAAGAGCGCATATGTCTTGTGACAACCAACTTCCAAACTAAGAGCATGTCTAGCATGGTGTCAGA
CACTAGTTGCACATTCCCTTCATCTGATGGCATATTCTGGAAGCATTGGATTCAAACCAAGGATGGGCAGTGTGGCA
GTCCATTAGTATCAACTAGAGATGGGTTCATTGTTGGTATACACTCAGCATCGAATTTCACCAACACAAACAATTAT
TTCACAAGCGTGCCGAAAAACTTCATGGAATTGTTGACAAATCAGGAGGCGCAGCAGTGGGTTAGTGGTTGGCGATT
AAATGCTGACTCAGTATTGTGGGGGGGCCATAAAGTTTTCATGTAG

C. Amino acid sequence   (SEQ ID NO:32)
MCRAISLRRLLLLLLQLSQLLAVTQGVSKGEEVIKEFMRFKVRMEGSMNGHEFEIEGEGEGRPYEGTQTAKLKVTKG
GPLPFAWDILSPQFMYGSKAYVKHPADIPDYKKLSFPEGFKWERVMNFEDGGLVTVTQDSSLQDGTLIYKVKMRGTN
FPPDGPVMQKKTMGWEASTERLYPRDGVLKGEIHQALKLKDGGHYLVEFKTIYMAKKPVQLPGYYYVDTKLDITSHN
EDYTIVEQYERSEGRHHLFLYGMDELYKKLFWALVVVAGVLFCYGLLVTVALCVESLFKGPRDYNPISSTICHLTNE
SDGHTTSLYGIGFGPFIITNKHLFRRNNGTLLVQSLHGVFKVKNTTTLQQHLIDGRDMIIIRMPKDFPPFPQKLKFR
EPQREERICLVTTNFQTKSMSSMVSDTSCTFPSSDGIFWKHWIQTKDGQCGSPLVSTRDGFIVGIHSASNFTNTNNY
FTSVPKNFMELLTNQEAQQWVSGWRLNADSVLWGGHKVFM

SEQUENCE LISTING

```
<160> NUMBER OF SEQ ID NOS: 33

<210> SEQ ID NO 1
<211> LENGTH: 1893
<212> TYPE: DNA
<213> ORGANISM: Artificial sequence
<220> FEATURE:
<223> OTHER INFORMATION: Synthetic

<400> SEQUENCE: 1
atgtgccgag ccatctctct taggcgcttg ctgctgctgc tgctgcagct gtcacaactc      60
ctagctgtca ctcaagggat ggtgagcaag ggcgaggagg ataacatggc catcatcaag     120
gagttcatgc gcttcaaggt gcacatggag ggctccgtga acggccacga gttcgagatc     180
gagggcgagg gcgagggccg cccctacgag ggcacccaga ccgccaagct gaaggtgacc     240
```

```
aagggtggcc ccctgcccct tcgcctggga catcctgtcc cctcagttca tgtacggctcc    300
aaggcctacg tgaagcaccc cgccgacatc cccgactact tgaagctgtc cttccccgag    360
ggcttcaagt gggagcgcgt gatgaacttc gaggacggcg gcgtggtgac cgtgacccag    420
gactcctccc tgcaggacgg cgagttcatc tacaaggtga agctgcgcgg caccaacttc    480
ccctccgacg gccccgtaat gcagaagaag accatgggct gggaggcctc ctccgagcgg    540
atgtaccccg aggacggcgc cctgaagggc gagatcaagc agaggctgaa gctgaaggac    600
ggcggccact acgacgctga ggtcaagacc acctacaagg ccaagaagcc cgtgcagctg    660
cccgcgcct acaacgtcaa catcaagttg gacatcacct cccacaacga ggactacacc    720
atcgtggaac agtacgaacg cgccgagggc cgccactcca ccggcggcat ggacgagctg    780
tacaagaagc ttttttgggc actggtcgtg gttgctggag tcctgttttg ttatggcttg    840
ctagtgacag tggctctttg tgttgaaaac ctgtattttc agggtatgtc tagattagat    900
aaaagtaaag tgattaacag cgcattagag ctgcttaatg aggtcggaat cgaaggttta    960
acaacccgta aactcgccca aagctaggt gtagagcagc ctacattgta ttggcatgta   1020
aaaaataagc gggctttgct cgacgcctta gccattgaga tgttagatag caccatact   1080
cacttttgcc ctttagaagg ggaaagctgg caagattttt tacgtaataa cgctaaaagt   1140
tttagatgtg ctttactaag tcatcgcgat ggagcaaaag tacatttagg tacacggcct   1200
acagaaaaac agtatgaaac tctcgaaaat caattagcct ttttatgcca acaaggtttt   1260
tcactagaga atgcattata tgcactcagc gctgtgggc atttttactt aggttgcgta   1320
ttggaagatc aagagcatca agtcgctaaa gaagaagg aaacacctac tactgatagt   1380
atgccgccat tattacgaca agctatcgaa ttatttgatc accaaggtgc agagccagcc   1440
ttcttattcg gccttgaatt gatcatatgc ggattagaaa acaacttaa atgtgaaagt   1500
gggtccgcgt acagccgcgc gcgtacgaaa aacaattacg ggtctaccat cgagggcctg   1560
ctcgatctcc cggacgacga cgcccccgaa gaggcggggc tggcggctcc gcgcctgtcc   1620
tttctccccg cgggacacac gcgcagactg tcgacggccc ccccgaccga tgtcagcctg   1680
ggggacgagc tccacttaga cggcgaggac gtggcgatgg cgcatgccga cgcgctagac   1740
gatttcgatc tggacatgtt gggggacggg gattccccgg gtccgggatt tacccccac    1800
gactccgccc cctacggcgc tctggatatg gccgacttcg agtttgagca gatgtttacc   1860
gatgcccttg gaattgacga gtacggtggg tag                                 1893
```

<210> SEQ ID NO 2
<211> LENGTH: 630
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (295)..(295)
<223> OTHER INFORMATION: Xaa is Gly, Ala, Glu, Leu, Ser, Tyr, or Lys

<400> SEQUENCE: 2

Met Cys Arg Ala Ile Ser Leu Arg Arg Leu Leu Leu Leu Leu Leu Gln
1               5                   10                  15

Leu Ser Gln Leu Leu Ala Val Thr Gln Gly Met Val Ser Lys Gly Glu
            20                  25                  30

Glu Asp Asn Met Ala Ile Ile Lys Glu Phe Met Arg Phe Lys Val His
        35                  40                  45

```
Met Glu Gly Ser Val Asn Gly His Glu Phe Glu Ile Glu Gly Glu Gly
         50                  55                  60

Glu Gly Arg Pro Tyr Glu Gly Thr Gln Thr Ala Lys Leu Lys Val Thr
 65                  70                  75                  80

Lys Gly Pro Leu Pro Phe Ala Trp Asp Ile Leu Ser Pro Gln Phe
                     85                  90                  95

Met Tyr Gly Ser Lys Ala Tyr Val Lys His Pro Ala Asp Ile Pro Asp
                100                 105                 110

Tyr Leu Lys Leu Ser Phe Pro Glu Gly Phe Lys Trp Glu Arg Val Met
            115                 120                 125

Asn Phe Glu Asp Gly Gly Val Val Thr Val Thr Gln Asp Ser Ser Leu
130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
            180                 185                 190

Lys Gln Arg Leu Lys Leu Lys Asp Gly Gly His Tyr Asp Ala Glu Val
            195                 200                 205

Lys Thr Thr Tyr Lys Ala Lys Lys Pro Val Gln Leu Pro Gly Ala Tyr
210                 215                 220

Asn Val Asn Ile Lys Leu Asp Ile Thr Ser His Asn Glu Asp Tyr Thr
225                 230                 235                 240

Ile Val Glu Gln Tyr Glu Arg Ala Glu Gly Arg His Ser Thr Gly Gly
                245                 250                 255

Met Asp Glu Leu Tyr Lys Lys Leu Phe Trp Ala Leu Val Val Val Ala
            260                 265                 270

Gly Val Leu Phe Cys Tyr Gly Leu Leu Val Thr Val Ala Leu Cys Val
            275                 280                 285

Glu Asn Leu Tyr Phe Gln Xaa Met Ser Arg Leu Asp Lys Ser Lys Val
            290                 295                 300

Ile Asn Ser Ala Leu Glu Leu Leu Asn Glu Val Gly Ile Glu Gly Leu
305                 310                 315                 320

Thr Thr Arg Lys Leu Ala Gln Lys Leu Gly Val Glu Gln Pro Thr Leu
            325                 330                 335

Tyr Trp His Val Lys Asn Lys Arg Ala Leu Leu Asp Ala Leu Ala Ile
            340                 345                 350

Glu Met Leu Asp Arg His His Thr His Phe Cys Pro Leu Glu Gly Glu
            355                 360                 365

Ser Trp Gln Asp Phe Leu Arg Asn Asn Ala Lys Ser Phe Arg Cys Ala
            370                 375                 380

Leu Leu Ser His Arg Asp Gly Ala Lys Val His Leu Gly Thr Arg Pro
385                 390                 395                 400

Thr Glu Lys Gln Tyr Glu Thr Leu Glu Asn Gln Leu Ala Phe Leu Cys
                405                 410                 415

Gln Gln Gly Phe Ser Leu Glu Asn Ala Leu Tyr Ala Leu Ser Ala Val
                420                 425                 430

Gly His Phe Thr Leu Gly Cys Val Leu Glu Asp Gln Glu His Gln Val
            435                 440                 445

Ala Lys Glu Glu Arg Glu Thr Pro Thr Thr Asp Ser Met Pro Pro Leu
450                 455                 460
```

Leu Arg Gln Ala Ile Glu Leu Phe Asp His Gln Gly Ala Glu Pro Ala
465                 470                 475                 480

Phe Leu Phe Gly Leu Glu Leu Ile Ile Cys Gly Leu Glu Lys Gln Leu
            485                 490                 495

Lys Cys Glu Ser Gly Ser Ala Tyr Ser Arg Ala Arg Thr Lys Asn Asn
            500                 505                 510

Tyr Gly Ser Thr Ile Glu Gly Leu Leu Asp Leu Pro Asp Asp Asp Ala
            515                 520                 525

Pro Glu Glu Ala Gly Leu Ala Ala Pro Arg Leu Ser Phe Leu Pro Ala
            530                 535                 540

Gly His Thr Arg Arg Leu Ser Thr Ala Pro Pro Thr Asp Val Ser Leu
545                 550                 555                 560

Gly Asp Glu Leu His Leu Asp Gly Glu Asp Val Ala Met Ala His Ala
            565                 570                 575

Asp Ala Leu Asp Asp Phe Asp Leu Asp Met Leu Gly Asp Gly Asp Ser
            580                 585                 590

Pro Gly Pro Gly Phe Thr Pro His Asp Ser Ala Pro Tyr Gly Ala Leu
            595                 600                 605

Asp Met Ala Asp Phe Glu Phe Glu Gln Met Phe Thr Asp Ala Leu Gly
            610                 615                 620

Ile Asp Glu Tyr Gly Gly
625                 630

<210> SEQ ID NO 3
<211> LENGTH: 1911
<212> TYPE: DNA
<213> ORGANISM: Artificial sequence
<220> FEATURE:
<223> OTHER INFORMATION: Synthetic

<400> SEQUENCE: 3
atgtgccgag ccatctctct taggcgcttg ctgctgctgc tgctgcagct gtcacaactc     60
ctagctgtca ctcaagggat ggtgagcaag ggcgaggagg ataacatggc catcatcaag    120
gagttcatgc gcttcaaggt gcacatggag ggctccgtga acggccacga gttcgagatc    180
gagggcgagg gcgagggccg ccctacgag ggcacccaga ccgccaagct gaaggtgacc    240
aagggtggcc ccctgccctt cgcctgggac atcctgtccc ctcagttcat gtacggctcc    300
aaggcctacg tgaagcaccc cgccgacatc cccgactact tgaagctgtc cttccccgag    360
ggcttcaagt gggagcgcgt gatgaacttc gaggacggcg gcgtggtgac cgtgacccag    420
gactcctccc tgcaggacgg cgagttcatc tacaaggtga agctgcgcgg caccaacttc    480
ccctccgacg gccccgtaat gcagaagaag accatgggct gggaggcctc ctccgagcgg    540 atgtacccg aggacggcgc cctgaagggc gagatcaagc agaggctgaa gctgaaggac    600
ggcggccact acgacgctga ggtcaagacc acctacaagg ccaagaagcc cgtgcagctg    660
cccggcgcct acaacgtcaa catcaagttg gacatcacct cccacaacga ggactacacc    720
atcgtggaac agtacgaacg cgccgagggc cgccactcca ccggcggcat ggacgagctg    780
tacaagaagc ttttttgggc actggtcgtg gttgctggag tcctgttttg ttatggcttg    840
ctagtgacag tggctctttg tgttatctgg gtaagatctg gtgaaaacct gtattttcag    900
ggtatgtcta gattagataa aagtaaagtg attaacagcg cattagagct gcttaatgag    960
gtcggaatcg aaggtttaac aacccgtaaa ctcgcccaga agctaggtgt agagcagcct   1020
acattgtatt ggcatgtaaa aaataagcgg gctttgctcg acgccttagc cattgagatg   1080

-continued

```
ttagataggc accatactca cttttgccct ttagaagggg aaagctggca agatttttta    1140
cgtaataacg ctaaaagttt tagatgtgct ttactaagtc atcgcgatgg agcaaaagta    1200
catttaggta cacggcctac agaaaaacag tatgaaactc tcgaaaatca attagccttt    1260
ttatgccaac aaggtttttc actagagaat gcattatatg cactcagcgc tgtggggcat    1320
tttactttag gttgcgtatt ggaagatcaa gagcatcaag tcgctaaaga agaaagggaa    1380
acacctacta ctgatagtat gccgccatta ttacgacaag ctatcgaatt atttgatcac    1440
caaggtgcag agccagcctt cttattcggc cttgaattga tcatatgcgg attagaaaaa    1500
caacttaaat gtgaaagtgg gtccgcgtac agccgcgcgc gtacgaaaaa caattacggg    1560
tctaccatcg agggcctgct cgatctcccg gacgacgacg cccccgaaga ggcggggctg    1620
gcggctccgc gcctgtcctt tctccccgcg ggacacacgc gcagactgtc gacggccccc    1680
ccgaccgatg tcagcctggg ggacgagctc cacttagacg gcgaggacgt ggcgatggcg    1740
catgccgacg cgctagacga tttcgatctg gacatgttgg gggacgggga ttccccgggt    1800
ccgggattta ccccccacga ctccgccccc tacggcgctc tggatatggc cgacttcgag    1860
tttgagcaga tgtttaccga tgcccttgga attgacgagt acggtgggta g             1911
```

<210> SEQ ID NO 4
<211> LENGTH: 636
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (301)..(301)
<223> OTHER INFORMATION: Xaa is Gly, Ala, Glu, Leu, Ser, Tyr, or Lys

<400> SEQUENCE: 4

```
Met Cys Arg Ala Ile Ser Leu Arg Arg Leu Leu Leu Leu Leu Gln
 1               5                   10                  15

Leu Ser Gln Leu Leu Ala Val Thr Gln Gly Met Val Ser Lys Gly Glu
            20                  25                  30

Glu Asp Asn Met Ala Ile Ile Lys Glu Phe Met Arg Phe Lys Val His
        35                  40                  45

Met Glu Gly Ser Val Asn Gly His Glu Phe Glu Ile Glu Gly Glu Gly
    50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Met Tyr Gly Ser Lys Ala Tyr Val Lys His Pro Ala Asp Ile Pro Asp
            100                 105                 110

Tyr Leu Lys Leu Ser Phe Pro Glu Gly Phe Lys Trp Glu Arg Val Met
        115                 120                 125

Asn Phe Glu Asp Gly Gly Val Val Thr Val Thr Gln Asp Ser Ser Leu
    130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
            180                 185                 190

Lys Gln Arg Leu Lys Leu Lys Asp Gly Gly His Tyr Asp Ala Glu Val
```

-continued

```
            195                 200                 205
Lys Thr Thr Tyr Lys Ala Lys Lys Pro Val Gln Leu Pro Gly Ala Tyr
210                 215                 220
Asn Val Asn Ile Lys Leu Asp Ile Thr Ser His Asn Glu Asp Tyr Thr
225                 230                 235                 240
Ile Val Glu Gln Tyr Glu Arg Ala Glu Gly Arg His Ser Thr Gly Gly
                245                 250                 255
Met Asp Glu Leu Tyr Lys Lys Leu Phe Trp Ala Leu Val Val Val Ala
                260                 265                 270
Gly Val Leu Phe Cys Tyr Gly Leu Leu Val Thr Val Ala Leu Cys Val
                275                 280                 285
Ile Trp Val Arg Ser Gly Glu Asn Leu Tyr Phe Gln Xaa Met Ser Arg
                290                 295                 300
Leu Asp Lys Ser Lys Val Ile Asn Ser Ala Leu Glu Leu Leu Asn Glu
305                 310                 315                 320
Val Gly Ile Glu Gly Leu Thr Thr Arg Lys Leu Ala Gln Lys Leu Gly
                325                 330                 335
Val Glu Gln Pro Thr Leu Tyr Trp His Val Lys Asn Lys Arg Ala Leu
                340                 345                 350
Leu Asp Ala Leu Ala Ile Glu Met Leu Asp Arg His His Thr His Phe
                355                 360                 365
Cys Pro Leu Glu Gly Glu Ser Trp Gln Asp Phe Leu Arg Asn Asn Ala
                370                 375                 380
Lys Ser Phe Arg Cys Ala Leu Leu Ser His Arg Asp Gly Ala Lys Val
385                 390                 395                 400
His Leu Gly Thr Arg Pro Thr Glu Lys Gln Tyr Glu Thr Leu Glu Asn
                405                 410                 415
Gln Leu Ala Phe Leu Cys Gln Gln Gly Phe Ser Leu Glu Asn Ala Leu
                420                 425                 430
Tyr Ala Leu Ser Ala Val Gly His Phe Thr Leu Gly Cys Val Leu Glu
                435                 440                 445
Asp Gln Glu His Gln Val Ala Lys Glu Glu Arg Glu Thr Pro Thr Thr
                450                 455                 460
Asp Ser Met Pro Pro Leu Leu Arg Gln Ala Ile Glu Leu Phe Asp His
465                 470                 475                 480
Gln Gly Ala Glu Pro Ala Phe Leu Phe Gly Leu Glu Leu Ile Ile Cys
                485                 490                 495
Gly Leu Glu Lys Gln Leu Lys Cys Glu Ser Gly Ser Ala Tyr Ser Arg
                500                 505                 510
Ala Arg Thr Lys Asn Asn Tyr Gly Ser Thr Ile Glu Gly Leu Leu Asp
                515                 520                 525
Leu Pro Asp Asp Asp Ala Pro Glu Glu Ala Gly Leu Ala Ala Pro Arg
                530                 535                 540
Leu Ser Phe Leu Pro Ala Gly His Thr Arg Arg Leu Ser Thr Ala Pro
545                 550                 555                 560
Pro Thr Asp Val Ser Leu Gly Asp Glu Leu His Leu Asp Gly Glu Asp
                565                 570                 575
Val Ala Met Ala His Ala Asp Ala Leu Asp Asp Phe Asp Leu Asp Met
                580                 585                 590
Leu Gly Asp Gly Asp Ser Pro Gly Pro Gly Phe Thr Pro His Asp Ser
                595                 600                 605
Ala Pro Tyr Gly Ala Leu Asp Met Ala Asp Phe Glu Phe Glu Gln Met
                610                 615                 620
```

Phe Thr Asp Ala Leu Gly Ile Asp Glu Tyr Gly Gly
625                 630                 635

<210> SEQ ID NO 5
<211> LENGTH: 1572
<212> TYPE: DNA
<213> ORGANISM: Artificial sequence
<220> FEATURE:
<223> OTHER INFORMATION: Synthetic

<400> SEQUENCE: 5

```
atgtgccgag ccatctctct taggcgcttg ctgctgctgc tgctgcagct gtcacaactc      60
ctagctgtca ctcaagggat ggtgagcaag ggcgaggagg ataacatggc catcatcaag     120
gagttcatgc gcttcaaggt gcacatggag ggctccgtga acggccacga gttcgagatc     180
gagggcgagg gcgagggccg cccctacgag ggcacccaga ccgccaagct gaaggtgacc     240
aagggtggcc ccctgccctt cgcctgggac atcctgtccc ctcagttcat gtacggctcc     300
aaggcctacg tgaagcaccc cgccgacatc cccgactact tgaagctgtc cttccccgag     360
ggcttcaagt gggagcgcgt gatgaacttc gaggacggcg gcgtggtgac cgtgacccag     420
gactcctccc tgcaggacgg cgagttcatc tacaaggtga agctgcgcgg caccaacttc     480
ccctccgacg gccccgtaat gcagaagaag accatgggct gggaggcctc ctccgagcgg     540
atgtaccccg aggacggcgc cctgaagggc gagatcaagc agaggctgaa gctgaaggac     600
ggcggccact acgacgctga ggtcaagacc acctacaagg ccaagaagcc cgtgcagctg     660
cccggcgcct acaacgtcaa catcaagttg gacatcacct cccacaacga ggactacacc     720
atcgtggaac agtacgaacg cgccgagggc cgccactcca ccggcggcat ggacgagctg     780
tacaagaagc ttttttgggc actggtcgtg gttgctggag tcctgttttg ttatggcttg     840
ctagtgacag tggctctttg tgttgagagc ttgtttaagg ggccgcgtga ttacaacccg     900
atatcgagca ccatttgtca tttgacgaat gaatctgatg gcacacaac atcgttgtat      960
ggtattggat ttggtcccctt catcattaca acaagcact tgtttagaag aaataatgga    1020
acactgttgg tccaatcact acatggtgta ttcaaggtca gaacaccac gactttgcaa     1080
caacacctca ttgatgggag ggacatgata attattcgca tgcctaagga tttcccacca    1140
tttcctcaaa agctgaaatt tagagagcca caaagggaag agcgcatatg tcttgtgaca    1200
accaacttcc aaactaagag catgtctagc atggtgtcag acactagttg cacattccct    1260
tcatctgatg gcatattctg gaagcattgg attcaaacca aggatgggca gtgtggcagt    1320
ccattagtat caactagaga tgggttcatt gttggtatac actcagcatc gaatttcacc    1380
aacacaaaca attatttcac aagcgtgccg aaaaacttca tggaattgtt gacaaatcag    1440
gaggcgcagc agtgggttag tggttggcga ttaaatgctg actcagtatt gtgggggggc    1500
cataaagttt tcatggtgaa acctgaagag ccttttcagc cagttaagga agcgactcaa    1560
ctcatgaatt ag                                                       1572
```

<210> SEQ ID NO 6
<211> LENGTH: 523
<212> TYPE: PRT
<213> ORGANISM: Artificial sequence
<220> FEATURE:
<223> OTHER INFORMATION: Synthetic

<400> SEQUENCE: 6

Met Cys Arg Ala Ile Ser Leu Arg Arg Leu Leu Leu Leu Leu Leu Gln

-continued

```
1               5                   10                  15
Leu Ser Gln Leu Leu Ala Val Thr Gln Gly Met Val Ser Lys Gly Glu
                20                  25                  30

Glu Asp Asn Met Ala Ile Ile Lys Glu Phe Met Arg Phe Lys Val His
                35                  40                  45

Met Glu Gly Ser Val Asn Gly His Glu Phe Glu Ile Glu Gly Glu Gly
                50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Met Tyr Gly Ser Lys Ala Tyr Val Lys His Pro Ala Asp Ile Pro Asp
                100                 105                 110

Tyr Leu Lys Leu Ser Phe Pro Glu Gly Phe Lys Trp Glu Arg Val Met
                115                 120                 125

Asn Phe Glu Asp Gly Gly Val Val Thr Val Thr Gln Asp Ser Ser Leu
                130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
                180                 185                 190

Lys Gln Arg Leu Lys Leu Lys Asp Gly Gly His Tyr Asp Ala Glu Val
                195                 200                 205

Lys Thr Thr Tyr Lys Ala Lys Lys Pro Val Gln Leu Pro Gly Ala Tyr
                210                 215                 220

Asn Val Asn Ile Lys Leu Asp Ile Thr Ser His Asn Glu Asp Tyr Thr
225                 230                 235                 240

Ile Val Glu Gln Tyr Glu Arg Ala Glu Gly Arg His Ser Thr Gly Gly
                245                 250                 255

Met Asp Glu Leu Tyr Lys Lys Leu Phe Trp Ala Leu Val Val Val Ala
                260                 265                 270

Gly Val Leu Phe Cys Tyr Gly Leu Leu Val Thr Val Ala Leu Cys Val
                275                 280                 285

Glu Ser Leu Phe Lys Gly Pro Arg Asp Tyr Asn Pro Ile Ser Ser Thr
                290                 295                 300

Ile Cys His Leu Thr Asn Glu Ser Asp Gly His Thr Thr Ser Leu Tyr
305                 310                 315                 320

Gly Ile Gly Phe Gly Pro Phe Ile Ile Thr Asn Lys His Leu Phe Arg
                325                 330                 335

Arg Asn Asn Gly Thr Leu Leu Val Gln Ser Leu His Gly Val Phe Lys
                340                 345                 350

Val Lys Asn Thr Thr Thr Leu Gln Gln His Leu Ile Asp Gly Arg Asp
                355                 360                 365

Met Ile Ile Ile Arg Met Pro Lys Asp Phe Pro Pro Phe Pro Gln Lys
                370                 375                 380

Leu Lys Phe Arg Glu Pro Gln Arg Glu Glu Arg Ile Cys Leu Val Thr
385                 390                 395                 400

Thr Asn Phe Gln Thr Lys Ser Met Ser Ser Met Val Ser Asp Thr Ser
                405                 410                 415

Cys Thr Phe Pro Ser Ser Asp Gly Ile Phe Trp Lys His Trp Ile Gln
                420                 425                 430
```

```
        Thr Lys Asp Gly Gln Cys Gly Ser Pro Leu Val Ser Thr Arg Asp Gly
            435                 440                 445

Phe Ile Val Gly Ile His Ser Ala Ser Asn Phe Thr Asn Thr Asn Asn
        450                 455                 460

Tyr Phe Thr Ser Val Pro Lys Asn Phe Met Glu Leu Leu Thr Asn Gln
        465                 470                 475                 480

Glu Ala Gln Gln Trp Val Ser Gly Trp Arg Leu Asn Ala Asp Ser Val
                        485                 490                 495

Leu Trp Gly Gly His Lys Val Phe Met Val Lys Pro Glu Glu Pro Phe
                        500                 505                 510

Gln Pro Val Lys Glu Ala Thr Gln Leu Met Asn
                        515                 520

<210> SEQ ID NO 7
<211> LENGTH: 1590
<212> TYPE: DNA
<213> ORGANISM: Artificial sequence
<220> FEATURE:
<223> OTHER INFORMATION: Synthetic

<400> SEQUENCE: 7
atgtgccgag ccatctctct taggcgcttg ctgctgctgc tgctgcagct gtcacaactc     60
ctagctgtca ctcaagggat ggtgagcaag ggcgaggagg ataacatggc catcatcaag    120
gagttcatgc gcttcaaggt gcacatggag ggctccgtga acggccacga gttcgagatc    180
gagggcgagg gcgagggccg cccctacgag ggcacccaga ccgccaagct gaaggtgacc    240
aagggtggcc ccctgccctt cgcctgggac atcctgtccc ctcagttcat gtacggctcc    300
aaggcctacg tgaagcaccc cgccgacatc cccgactact tgaagctgtc cttccccgag    360
ggcttcaagt gggagcgcgt gatgaacttc gaggacggcg gcgtggtgac cgtgacccag    420
gactcctccc tgcaggacgg cgagttcatc tacaaggtga agctgcgcgg caccaacttc    480
ccctccgacg gccccgtaat gcagaagaag accatgggct gggaggcctc ctccgagcgg    540
atgtaccccg aggacggcgc cctgaagggc gagatcaagc agaggctgaa gctgaaggac    600
ggcggccact acgacgctga ggtcaagacc acctacaagg ccaagaagcc cgtgcagctg    660
cccggcgcct acaacgtcaa catcaagttg gacatcacct cccacaacga ggactacacc    720
atcgtggaaa gtacgaacg cgccgagggc cgccactcca ccgcggcat ggacgagctg    780 tacaagaagc ttttttgggc actggtcgtg gttgctggag tcctgttttg ttatggcttg    840
ctagtgacag tggctctttg tgttatctgg gtaagatctg gtgagagctt gtttaagggg    900
ccgcgtgatt acaacccgat atcgagcacc atttgtcatt tgacgaatga atctgatggg    960
cacacaacat cgttgtatgg tattggattt ggtcccttca tcattacaaa caagcacttg    1020
tttagaagaa ataatggaac actgttggtc caatcactac atggtgtatt caaggtcaag    1080
aacaccacga ctttgcaaca cacctcatt gatgggaggg acatgataat tattcgcatg    1140
cctaaggatt tcccaccatt tcctcaaaag ctgaaattta gagagccaca agggaagag    1200 cgcatatgtc ttgtgacaac caacttccaa actaagagca tgtctagcat ggtgtcagac    1260
actagttgca cattcccttc atctgatggc atattctgga agcattggat tcaaaccaag    1320
gatgggcagt gtggcagtcc attagtatca actagagatg ggttcattgt tggtatacac    1380
tcagcatcga atttccaccaa cacaaacaat tatttcacaa gcgtgccgaa aaacttcatg    1440
gaattgttga caaatcagga ggcgcagcag tgggttagtg gttggcgatt aaatgctgac    1500
```

```
tcagtattgt gggggggcca taaagttttc atggtgaaac ctgaagagcc ttttcagcca    1560
gttaaggaag cgactcaact catgaattag                                    1590
```

<210> SEQ ID NO 8
<211> LENGTH: 529
<212> TYPE: PRT
<213> ORGANISM: Artificial sequence
<220> FEATURE:
<223> OTHER INFORMATION: Synthetic

<400> SEQUENCE: 8

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Met Val Ser Lys Gly Glu
            20                  25                  30

Glu Asp Asn Met Ala Ile Ile Lys Glu Phe Met Arg Phe Lys Val His
        35                  40                  45

Met Glu Gly Ser Val Asn Gly His Glu Phe Glu Ile Glu Gly Glu Gly
    50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Met Tyr Gly Ser Lys Ala Tyr Val Lys His Pro Ala Asp Ile Pro Asp
            100                 105                 110

Tyr Leu Lys Leu Ser Phe Pro Glu Gly Phe Lys Trp Glu Arg Val Met
        115                 120                 125

Asn Phe Glu Asp Gly Gly Val Val Thr Val Thr Gln Asp Ser Ser Leu
    130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
            180                 185                 190

Lys Gln Arg Leu Lys Leu Lys Asp Gly Gly His Tyr Asp Ala Glu Val
        195                 200                 205

Lys Thr Thr Tyr Lys Ala Lys Lys Pro Val Gln Leu Pro Gly Ala Tyr
    210                 215                 220

Asn Val Asn Ile Lys Leu Asp Ile Thr Ser His Asn Glu Asp Tyr Thr
225                 230                 235                 240

Ile Val Glu Gln Tyr Glu Arg Ala Glu Gly Arg His Ser Thr Gly Gly
                245                 250                 255

Met Asp Glu Leu Tyr Lys Lys Leu Phe Trp Ala Leu Val Val Val Ala
            260                 265                 270

Gly Val Leu Phe Cys Tyr Gly Leu Leu Val Thr Val Ala Leu Cys Val
        275                 280                 285

Ile Trp Val Arg Ser Gly Glu Ser Leu Phe Lys Gly Pro Arg Asp Tyr
    290                 295                 300

Asn Pro Ile Ser Ser Thr Ile Cys His Leu Thr Asn Glu Ser Asp Gly
305                 310                 315                 320

His Thr Thr Ser Leu Tyr Gly Ile Gly Phe Gly Pro Phe Ile Ile Thr
                325                 330                 335

Asn Lys His Leu Phe Arg Arg Asn Asn Gly Thr Leu Leu Val Gln Ser
            340                 345                 350
```

```
Leu His Gly Val Phe Lys Val Lys Asn Thr Thr Leu Gln Gln His
        355                 360                 365
Leu Ile Asp Gly Arg Asp Met Ile Ile Arg Met Pro Lys Asp Phe
370                 375                 380
Pro Pro Phe Pro Gln Lys Leu Lys Phe Arg Glu Pro Gln Arg Glu Glu
385                 390                 395                 400
Arg Ile Cys Leu Val Thr Thr Asn Phe Gln Thr Lys Ser Met Ser Ser
                    405                 410                 415
Met Val Ser Asp Thr Ser Cys Thr Phe Pro Ser Ser Asp Gly Ile Phe
                420                 425                 430
Trp Lys His Trp Ile Gln Thr Lys Asp Gly Gln Cys Gly Ser Pro Leu
                    435                 440                 445
Val Ser Thr Arg Asp Gly Phe Ile Val Gly Ile His Ser Ala Ser Asn
                450                 455                 460
Phe Thr Asn Thr Asn Asn Tyr Phe Thr Ser Val Pro Lys Asn Phe Met
465                 470                 475                 480
Glu Leu Leu Thr Asn Gln Glu Ala Gln Gln Trp Val Ser Gly Trp Arg
                    485                 490                 495
Leu Asn Ala Asp Ser Val Leu Trp Gly Gly His Lys Val Phe Met Val
                500                 505                 510
Lys Pro Glu Glu Pro Phe Gln Pro Val Lys Glu Ala Thr Gln Leu Met
        515                 520                 525
Asn
```

<210> SEQ ID NO 9
<211> LENGTH: 1884
<212> TYPE: DNA
<213> ORGANISM: Artificial sequence
<220> FEATURE:
<223> OTHER INFORMATION: Synthetic

<400> SEQUENCE: 9

```
atgtgccgag ccatctctct taggcgcttg ctgctgctgc tgctgcagct gtcacaactc        60
ctagctgtca ctcaagggggt gagcaagggc gaggaggtca tcaaagagtt catgcgcttc      120
aaggtgcgca tggagggctc catgaacggc cacgagttcg agatcgaggg cgagggcgag      180
ggccgcccct acgagggcac ccagaccgcc aagctgaagg tgaccaaggg cggcccctg       240
cccttcgcct gggacatcct gtcccccag ttcatgtacg gctccaaggc gtacgtgaag       300
caccccgccg acatcccga ttacaagaag ctgtccttcc ccgagggctt caagtgggag       360
cgcgtgatga acttcgagga cggcggtctg gtgaccgtga cccaggactc ctccctgcag      420
gacggcacgc tgatctacaa ggtgaagatg cgcggcacca acttcccccc cgacggcccc      480
gtaatgcaga agaagaccat gggctgggag gcctccaccg agcgcctgta ccccgcgac      540
ggcgtgctga agggcgagat ccaccaggcc ctgaagctga aggacggcgg ccactacctg      600
gtggagttca gaccatcta catggccaag aagcccgtgc aactgcccgg ctactactac       660
gtggacacca gctggacat cacctcccac aacgaggact acaccatcgt ggaacagtac       720
gagcgctccg agggccgcca ccacctgttc tgtacggca tggacgagct gtacaagaag       780
cttttttggg cactggtcgt ggttgctgga gtcctgtttt gttatggctt gctagtgaca       840
gtggctcttt gtgttgaaaa cctgtatttt cagggtatgt ctagattaga taaaagtaaa      900
gtgattaaca gcgcattaga gctgcttaat gaggtcggaa tcgaaggttt aacaacccgt      960
aaactcgccc agaagctagg tgtagagcag cctacattgt attggcatgt aaaaaataag   1020
```

```
cgggctttgc tcgacgcctt agccattgag atgttagata ggcaccatac tcacttttgc    1080
cctttagaag gggaaagctg gcaagatttt ttacgtaata acgctaaaag ttttagatgt    1140
gctttactaa gtcatcgcga tggagcaaaa gtacatttag gtacacggcc tacagaaaaa    1200
cagtatgaaa ctctcgaaaa tcaattagcc ttttatgcc aacaaggttt ttcactagag     1260
aatgcattat atgcactcag cgctgtgggg cattttactt taggttgcgt attggaagat    1320
caagagcatc aagtcgctaa agaagaaagg gaaacaccta ctactgatag tatgccgcca    1380
ttattacgac aagctatcga attatttgat caccaaggtg cagagccagc cttcttattc    1440
ggccttgaat tgatcatatg cggattagaa aaacaactta atgtgaaag tgggtccgcg     1500 tacagccgcg cgcgtacgaa aaacaattac gggtctacca tcgagggcct gctcgatctc    1560
ccggacgacg acgcccccga agaggcgggg ctggcggctc cgcgcctgtc ctttctcccc    1620
gcgggacaca cgcgcagact gtcgacggcc cccccgaccg atgtcagcct gggggacgag    1680
ctccacttag acggcgagga cgtggcgatg gcgcatgccg acgcgctaga cgatttcgat    1740
ctggacatgt tggggacgg ggattccccg gtccgggat ttaccccca cgactccgcc       1800 ccctacggcg ctctggatat ggccgacttc gagtttgagc agatgtttac cgatgccctt    1860
ggaattgacg agtacggtgg gtag                                           1884
```

<210> SEQ ID NO 10
<211> LENGTH: 627
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (292)..(292)
<223> OTHER INFORMATION: Xaa is Gly, Ala, Glu, Leu, Ser, Tyr, or Lys

<400> SEQUENCE: 10

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Val Ser Lys Gly Glu Glu
            20                  25                  30

Val Ile Lys Glu Phe Met Arg Phe Lys Val Arg Met Glu Gly Ser Met
        35                  40                  45

Asn Gly His Glu Phe Glu Ile Glu Gly Glu Gly Glu Gly Arg Pro Tyr
    50                  55                  60

Glu Gly Thr Gln Thr Ala Lys Leu Lys Val Thr Lys Gly Gly Pro Leu
65                  70                  75                  80

Pro Phe Ala Trp Asp Ile Leu Ser Pro Gln Phe Met Tyr Gly Ser Lys
                85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140

Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
                165                 170                 175

Tyr Pro Arg Asp Gly Val Leu Lys Gly Glu Ile His Gln Ala Leu Lys
```

```
                180             185                 190
Leu Lys Asp Gly Gly His Tyr Leu Val Glu Phe Lys Thr Ile Tyr Met
            195                 200                 205
Ala Lys Lys Pro Val Gln Leu Pro Gly Tyr Tyr Val Asp Thr Lys
            210                 215             220
Leu Asp Ile Thr Ser His Asn Glu Asp Tyr Thr Ile Val Glu Gln Tyr
225                         230              235                 240
Glu Arg Ser Glu Gly Arg His His Leu Phe Leu Tyr Gly Met Asp Glu
                245                 250                 255
Leu Tyr Lys Lys Leu Phe Trp Ala Leu Val Val Ala Gly Val Leu
            260                 265             270
Phe Cys Tyr Gly Leu Leu Val Thr Val Ala Leu Cys Val Glu Asn Leu
        275                 280              285
Tyr Phe Gln Xaa Met Ser Arg Leu Asp Lys Ser Lys Val Ile Asn Ser
        290                 295             300
Ala Leu Glu Leu Leu Asn Glu Val Gly Ile Glu Gly Leu Thr Thr Arg
305                 310                 315                 320
Lys Leu Ala Gln Lys Leu Gly Val Glu Gln Pro Thr Leu Tyr Trp His
                325                 330                 335
Val Lys Asn Lys Arg Ala Leu Leu Asp Ala Leu Ala Ile Glu Met Leu
                340                 345                 350
Asp Arg His His Thr His Phe Cys Pro Leu Gly Leu Gly Ser Trp Gln
            355                 360                 365
Asp Phe Leu Arg Asn Asn Ala Lys Ser Phe Arg Cys Ala Leu Leu Ser
        370                 375              380
His Arg Asp Gly Ala Lys Val His Leu Gly Thr Arg Pro Thr Glu Lys
385                 390                 395                 400
Gln Tyr Glu Thr Leu Glu Asn Gln Leu Ala Phe Leu Cys Gln Gln Gly
                405                 410                 415
Phe Ser Leu Glu Asn Ala Leu Tyr Ala Leu Ser Ala Val Gly His Phe
            420                 425             430
Thr Leu Gly Cys Val Leu Glu Asp Gln Glu His Gln Val Ala Lys Glu
            435                 440             445
Glu Arg Glu Thr Pro Thr Thr Asp Ser Met Pro Pro Leu Leu Arg Gln
            450                 455             460
Ala Ile Glu Leu Phe Asp His Gln Gly Ala Glu Pro Ala Phe Leu Phe
465                 470                 475                 480
Gly Leu Glu Leu Ile Ile Cys Gly Leu Glu Lys Gln Leu Lys Cys Glu
                485                 490                 495
Ser Gly Ser Ala Tyr Ser Arg Ala Arg Thr Lys Asn Asn Tyr Gly Ser
            500                 505                 510
Thr Ile Glu Gly Leu Leu Asp Leu Pro Asp Asp Ala Pro Glu Glu
            515                 520             525
Ala Gly Leu Ala Ala Pro Arg Leu Ser Phe Leu Pro Ala Gly His Thr
            530                 535             540
Arg Arg Leu Ser Thr Ala Pro Pro Thr Asp Val Ser Leu Gly Asp Glu
545                 550                 555                 560
Leu His Leu Asp Gly Glu Asp Val Ala Met Ala His Ala Asp Ala Leu
                565                 570                 575
Asp Asp Phe Asp Leu Asp Met Leu Gly Asp Gly Asp Ser Pro Gly Pro
            580                 585                 590
Gly Phe Thr Pro His Asp Ser Ala Pro Tyr Gly Ala Leu Asp Met Ala
            595                 600                 605
```

Asp Phe Glu Phe Glu Gln Met Phe Thr Asp Ala Leu Gly Ile Asp Glu
    610                 615                 620

Tyr Gly Gly
625

<210> SEQ ID NO 11
<211> LENGTH: 1902
<212> TYPE: DNA
<213> ORGANISM: Artificial sequence
<220> FEATURE:
<223> OTHER INFORMATION: Synthetic

<400> SEQUENCE: 11

```
atgtgccgag ccatctctct taggcgcttg ctgctgctgc tgctgcagct gtcacaactc      60
ctagctgtca ctcaagggggt gagcaagggc gaggaggtca tcaaagagtt catgcgcttc     120
aaggtgcgca tggagggctc catgaacggc cacgagttcg agatcgaggg cgagggcgag     180
ggccgcccct acgagggcac ccagaccgcc aagctgaagg tgaccaaggg cggccccctg     240
cccttcgcct gggacatcct gtccccccag ttcatgtacg gctccaaggc gtacgtgaag     300
caccccgccg acatccccga ttacaagaag ctgtccttcc ccgagggctt caagtgggag     360
cgcgtgatga acttcgagga cggcggtctg gtgaccgtga cccaggactc ctccctgcag     420
gacggcacgc tgatctacaa ggtgaagatg cgcggcacca acttccccc cgacggcccc      480
gtaatgcaga agaagaccat gggctgggag gcctccaccg agcgcctgta ccccgcgac      540
ggcgtgctga agggcgagat ccaccaggcc ctgaagctga aggacggcgg ccactacctg     600
gtggagttca gaccatcta catggccaag aagcccgtgc aactgcccgg ctactactac      660
gtggacacca gctggacat cacctcccac aacgaggact acaccatcgt ggaacagtac      720
gagcgctccg agggccgcca ccacctgttc ctgtacggca tggacgagct gtacaagaag     780
cttttttggg cactggtcgt ggttgctgga gtcctgtttt gttatggctt gctagtgaca      840
gtggctcttt gtgttatctg ggtaagatct ggtgaaaacc tgtattttca gggtatgtct     900
agattagata aaagtaaagt gattaacagc gcattagagc tgcttaatga ggtcggaatc     960
gaaggtttaa caacccgtaa actcgcccag aagctaggtg tagagcagcc tacattgtat    1020
tggcatgtaa aaaataagcg ggcttttgctc gacgccttag ccattgagat gttagatagg    1080
caccatactc acttttgccc tttagaaggg gaaagctggc aagatttttt acgtaataac    1140
gctaaaagtt ttagatgtgc tttactaagt catcgcgatg gagcaaaagt acatttaggt    1200
acacggccta cagaaaaaca gtatgaaact ctcgaaaatc aattagcctt tttatgccaa    1260
caaggttttt cactagagaa tgcattatat gcactcagcg ctgtggggca tttttacttta    1320
ggttgcgtat tggaagatca agagcatcaa gtcgctaaag aagaagggaa acacctact     1380
actgatagta tgccgccatt attacgacaa gctatcgaat tatttgatca ccaaggtgca    1440
gagccagcct tcttattcgg ccttgaattg atcatatgcg gattagaaaa acaacttaaa    1500
tgtgaaagtg gtccgcgta cagccgcgcg cgtacgaaaa acaattacgg gtctaccatc    1560
gagggcctgc tcgatctccc ggacgacgac gccccccgaag aggcggggct ggcggctccg    1620
cgcctgtcct ttctccccgc gggacacacg cgcagactgt cgacggcccc ccgaccgat    1680
gtcagcctgg ggacgagct ccacttagac ggcgaggacg tggcgatggc gcatgccgac    1740
gcgctagacg atttcgatct ggacatgttg ggggacgggg attccccggg tccgggattt    1800
acccccacg actccgcccc ctacggcgct ctggatatgg ccgacttcga gtttgagcag    1860
```

```
atgtttaccg atgcccttgg aattgacgag tacggtgggt ag                    1902
```

<210> SEQ ID NO 12
<211> LENGTH: 633
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (298)..(298)
<223> OTHER INFORMATION: Xaa is Gly, Ala, Glu, Leu, Ser, Tyr, or Lys

<400> SEQUENCE: 12

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Val Ser Lys Gly Glu Glu
            20                  25                  30

Val Ile Lys Glu Phe Met Arg Phe Lys Val Arg Met Glu Gly Ser Met
        35                  40                  45

Asn Gly His Glu Phe Glu Ile Glu Gly Glu Gly Glu Gly Arg Pro Tyr
    50                  55                  60

Glu Gly Thr Gln Thr Ala Lys Leu Lys Val Thr Lys Gly Gly Pro Leu
65                  70                  75                  80

Pro Phe Ala Trp Asp Ile Leu Ser Pro Gln Phe Met Tyr Gly Ser Lys
                85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140

Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
                165                 170                 175

Tyr Pro Arg Asp Gly Val Leu Lys Gly Glu Ile His Gln Ala Leu Lys
            180                 185                 190

Leu Lys Asp Gly Gly His Tyr Leu Val Glu Phe Lys Thr Ile Tyr Met
        195                 200                 205

Ala Lys Lys Pro Val Gln Leu Pro Gly Tyr Tyr Tyr Val Asp Thr Lys
    210                 215                 220

Leu Asp Ile Thr Ser His Asn Glu Asp Tyr Thr Ile Val Glu Gln Tyr
225                 230                 235                 240

Glu Arg Ser Glu Gly Arg His His Leu Phe Leu Tyr Gly Met Asp Glu
                245                 250                 255

Leu Tyr Lys Lys Leu Phe Trp Ala Leu Val Val Val Ala Gly Val Leu
            260                 265                 270

Phe Cys Tyr Gly Leu Leu Val Thr Val Ala Leu Cys Val Ile Trp Val
        275                 280                 285

Arg Ser Gly Glu Asn Leu Tyr Phe Gln Xaa Met Ser Arg Leu Asp Lys
    290                 295                 300

Ser Lys Val Ile Asn Ser Ala Leu Glu Leu Leu Asn Glu Val Gly Ile
305                 310                 315                 320

Glu Gly Leu Thr Thr Arg Lys Leu Ala Gln Lys Leu Gly Val Glu Gln
                325                 330                 335
```

Pro Thr Leu Tyr Trp His Val Lys Asn Lys Arg Ala Leu Leu Asp Ala
            340                 345                 350

Leu Ala Ile Glu Met Leu Asp Arg His Thr His Phe Cys Pro Leu
        355                 360                 365

Glu Gly Glu Ser Trp Gln Asp Phe Leu Arg Asn Asn Ala Lys Ser Phe
    370                 375                 380

Arg Cys Ala Leu Leu Ser His Arg Asp Gly Ala Lys Val His Leu Gly
385                 390                 395                 400

Thr Arg Pro Thr Glu Lys Gln Tyr Glu Thr Leu Glu Asn Gln Leu Ala
                405                 410                 415

Phe Leu Cys Gln Gln Gly Phe Ser Leu Glu Asn Ala Leu Tyr Ala Leu
            420                 425                 430

Ser Ala Val Gly His Phe Thr Leu Gly Cys Val Leu Glu Asp Gln Glu
        435                 440                 445

His Gln Val Ala Lys Glu Glu Arg Glu Thr Pro Thr Thr Asp Ser Met
    450                 455                 460

Pro Pro Leu Leu Arg Gln Ala Ile Glu Leu Phe Asp His Gln Gly Ala
465                 470                 475                 480

Glu Pro Ala Phe Leu Phe Gly Leu Glu Leu Ile Ile Cys Gly Leu Glu
                485                 490                 495

Lys Gln Leu Lys Cys Glu Ser Gly Ser Ala Tyr Ser Arg Ala Arg Thr
            500                 505                 510

Lys Asn Asn Tyr Gly Ser Thr Ile Glu Gly Leu Leu Asp Leu Pro Asp
        515                 520                 525

Asp Asp Ala Pro Glu Glu Ala Gly Leu Ala Ala Pro Arg Leu Ser Phe
    530                 535                 540

Leu Pro Ala Gly His Thr Arg Arg Leu Ser Thr Ala Pro Pro Thr Asp
545                 550                 555                 560

Val Ser Leu Gly Asp Glu Leu His Leu Asp Gly Glu Asp Val Ala Met
                565                 570                 575

Ala His Ala Asp Ala Leu Asp Asp Phe Asp Leu Asp Met Leu Gly Asp
            580                 585                 590

Gly Asp Ser Pro Gly Pro Gly Phe Thr Pro His Asp Ser Ala Pro Tyr
        595                 600                 605

Gly Ala Leu Asp Met Ala Asp Phe Glu Phe Glu Gln Met Phe Thr Asp
    610                 615                 620

Ala Leu Gly Ile Asp Glu Tyr Gly Gly
625                 630

<210> SEQ ID NO 13
<211> LENGTH: 1563
<212> TYPE: DNA
<213> ORGANISM: Artificial sequence
<220> FEATURE:
<223> OTHER INFORMATION: Synthetic

<400> SEQUENCE: 13
atgtgccgag ccatctctct taggcgcttg ctgctgctgc tgctgcagct gtcacaactc      60
ctagctgtca ctcaagggt gagcaagggc gaggaggtca tcaaagagtt catgcgcttc     120
aaggtgcgca tggagggctc catgaacggc acgagttcg agatcgaggg cgagggcgag     180
ggccgcccct acgagggcac ccagaccgcc aagctgaagg tgaccaaggg cggccccctg     240
cccttcgcct gggacatcct gtcccccag ttcatgtacg ctccaaggc gtacgtgaag     300 caccccgccg acatccccga ttacaagaag ctgtccttcc ccgagggctt caagtgggag     360

-continued

```
cgcgtgatga acttcgagga cggcggtctg gtgaccgtga cccaggactc ctccctgcag    420
gacggcacgc tgatctacaa ggtgaagatg cgcggcacca acttcccccc cgacggcccc    480
gtaatgcaga agaagaccat gggctgggag gcctccaccg agcgcctgta ccccgcgac     540 ggcgtgctga agggcgagat ccaccaggcc ctgaagctga aggacggcgg ccactacctg    600
gtggagttca agaccatcta catggccaag aagcccgtgc aactgcccgg ctactactac    660
gtggacacca agctggacat cacctcccac aacgaggact acaccatcgt ggaacagtac    720
gagcgctccg agggccgcca ccacctgttc ctgtacggca tggacgagct gtacaagaag    780
cttttttggg cactggtcgt ggttgctgga gtcctgtttt gttatggctt gctagtgaca    840
gtggctcttt gtgttgagag cttgtttaag gggccgcgtg attacaaccc gatatcgagc    900
accatttgtc atttgacgaa tgaatctgat gggcacacaa catcgttgta tggtattgga    960
tttggtccct tcatcattac aaacaagcac ttgtttagaa gaaataatgg aacactgttg   1020
gtccaatcac tacatggtgt attcaaggtc aagaacacca cgactttgca caacacctc    1080 attgatggga gggacatgat aattattcgc atgcctaagg atttcccacc atttcctcaa   1140
aagctgaaat ttagagagcc acaaagggaa gagcgcatat gtcttgtgac aaccaacttc   1200
caaactaaga gcatgtctag catggtgtca gacactagtt gcacattccc ttcatctgat   1260
ggcatattct ggaagcattg gattcaaacc aaggatgggc agtgtggcag tccattagta   1320
tcaactagag atgggttcat tgttggtata cactcagcat cgaatttcac caacacaaac   1380
aattatttca caagcgtgcc gaaaaacttc atggaattgt tgacaaatca ggaggcgcag   1440
cagtgggtta gtggttggcg attaaatgct gactcagtat tgtgggggggg ccataaagtt   1500 ttcatggtga aacctgaaga gccttttcag ccagttaagg aagcgactca actcatgaat   1560
tag                                                                  1563
```

<210> SEQ ID NO 14
<211> LENGTH: 520
<212> TYPE: PRT
<213> ORGANISM: Artificial sequence
<220> FEATURE:
<223> OTHER INFORMATION: Synthetic

<400> SEQUENCE: 14

```
Met Cys Arg Ala Ile Ser Leu Arg Arg Leu Leu Leu Leu Leu Gln
1               5                   10                  15

Leu Ser Gln Leu Leu Ala Val Thr Gln Gly Val Ser Lys Gly Glu Glu
            20                  25                  30

Val Ile Lys Glu Phe Met Arg Phe Lys Val Arg Met Glu Gly Ser Met
        35                  40                  45

Asn Gly His Glu Phe Glu Ile Glu Gly Glu Gly Glu Gly Arg Pro Tyr
    50                  55                  60

Glu Gly Thr Gln Thr Ala Lys Leu Lys Val Thr Lys Gly Gly Pro Leu
65                  70                  75                  80

Pro Phe Ala Trp Asp Ile Leu Ser Pro Gln Phe Met Tyr Gly Ser Lys
                85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140
```

Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
            165                 170                 175

Tyr Pro Arg Asp Gly Val Leu Lys Gly Glu Ile His Gln Ala Leu Lys
        180                 185                 190

Leu Lys Asp Gly Gly His Tyr Leu Val Glu Phe Lys Thr Ile Tyr Met
    195                 200                 205

Ala Lys Lys Pro Val Gln Leu Pro Gly Tyr Tyr Val Asp Thr Lys
210                 215                 220

Leu Asp Ile Thr Ser His Asn Glu Asp Tyr Thr Ile Val Glu Gln Tyr
225                 230                 235                 240

Glu Arg Ser Glu Gly Arg His His Leu Phe Leu Tyr Gly Met Asp Glu
                245                 250                 255

Leu Tyr Lys Lys Leu Phe Trp Ala Leu Val Val Ala Gly Val Leu
        260                 265                 270

Phe Cys Tyr Gly Leu Leu Val Thr Val Ala Leu Cys Val Glu Ser Leu
    275                 280                 285

Phe Lys Gly Pro Arg Asp Tyr Asn Pro Ile Ser Ser Thr Ile Cys His
290                 295                 300

Leu Thr Asn Glu Ser Asp Gly His Thr Thr Ser Leu Tyr Gly Ile Gly
305                 310                 315                 320

Phe Gly Pro Phe Ile Ile Thr Asn Lys His Leu Phe Arg Arg Asn Asn
                325                 330                 335

Gly Thr Leu Leu Val Gln Ser Leu His Gly Val Phe Lys Val Lys Asn
        340                 345                 350

Thr Thr Thr Leu Gln Gln His Leu Ile Asp Gly Arg Asp Met Ile Ile
    355                 360                 365

Ile Arg Met Pro Lys Asp Phe Pro Pro Phe Pro Gln Lys Leu Lys Phe
370                 375                 380

Arg Glu Pro Gln Arg Glu Glu Arg Ile Cys Leu Val Thr Thr Asn Phe
385                 390                 395                 400

Gln Thr Lys Ser Met Ser Ser Met Val Ser Asp Thr Ser Cys Thr Phe
                405                 410                 415

Pro Ser Ser Asp Gly Ile Phe Trp Lys His Trp Ile Gln Thr Lys Asp
        420                 425                 430

Gly Gln Cys Gly Ser Pro Leu Val Ser Thr Arg Asp Gly Phe Ile Val
    435                 440                 445

Gly Ile His Ser Ala Ser Asn Phe Thr Asn Thr Asn Asn Tyr Phe Thr
450                 455                 460

Ser Val Pro Lys Asn Phe Met Glu Leu Leu Thr Asn Gln Glu Ala Gln
465                 470                 475                 480

Gln Trp Val Ser Gly Trp Arg Leu Asn Ala Asp Ser Val Leu Trp Gly
                485                 490                 495

Gly His Lys Val Phe Met Val Lys Pro Glu Glu Pro Phe Gln Pro Val
        500                 505                 510

Lys Glu Ala Thr Gln Leu Met Asn
    515                 520

<210> SEQ ID NO 15
<211> LENGTH: 1581
<212> TYPE: DNA
<213> ORGANISM: Artificial sequence
<220> FEATURE:
<223> OTHER INFORMATION: Synthetic

<400> SEQUENCE: 15

```
atgtgccgag ccatctctct taggcgcttg ctgctgctgc tgctgcagct gtcacaactc      60
ctagctgtca ctcaagggt gagcaagggc gaggaggtca tcaaagagtt catgcgcttc     120
aaggtgcgca tggagggctc catgaacggc acgagttcg agatcgaggg cgagggcgag      180
ggccgcccct acgagggcac ccagaccgcc aagctgaagg tgaccaaggg cggccccctg     240
cccttcgcct gggacatcct gtccccccag ttcatgtacg gctccaaggc gtacgtgaag     300
caccccgccg acatccccga ttacaagaag ctgtccttcc ccgagggctt caagtgggag     360
cgcgtgatga cttcgagga cggcggtctg gtgaccgtga cccaggactc ctccctgcag     420
gacggcacgc tgatctacaa ggtgaagatg cgcggcacca cttcccccc cgacggcccc     480
gtaatgcaga agaagaccat gggctgggag gcctccaccg agcgcctgta cccccgcgac     540
ggcgtgctga agggcgagat ccaccaggcc ctgaagctga aggacggcgg ccactacctg     600
gtggagttca gaccatcta catggccaag aagcccgtgc aactgcccgg ctactactac     660
gtggacacca agctggacat cacctcccac aacgaggact acaccatcgt ggaacagtac     720
gagcgctccg agggccgcca ccacctgttc ctgtacggca tggacgagct gtacaagaag     780
ctttttttggg cactggtcgt ggttgctgga gtcctgtttt gttatggctt gctagtgaca     840
gtggctcttt gtgttatctg gtaagatct ggtgagagct tgtttaaggg gccgcgtgat      900
tacaacccga tatcgagcac catttgtcat ttgacgaatg aatctgatgg gcacacaaca     960
tcgttgtatg gtattggatt tggtccttc atcattacaa caagcactt gtttagaaga      1020
aataatggaa cactgttggt ccaatcacta catggtgtat tcaaggtcaa gaacaccacg    1080
actttgcaac acacctcat tgatgggagg acatgataa ttattcgcat gcctaaggat      1140
ttcccaccat ttcctcaaaa gctgaaattt agagagccac aaagggaaga gcgcatatgt    1200
cttgtgacaa ccaacttcca aactaagagc atgtctagca tggtgtcaga cactagttgc    1260
acattccctt catctgatgg catattctgg aagcattgga ttcaaaccaa ggatgggcag    1320
tgtggcagtc cattagtatc aactagagat gggttcattg ttggtataca ctcagcatcg    1380
aattcacca acacaaacaa ttatttcaca agcgtgccga aaaacttcat ggaattgttg     1440
acaaatcagg aggcgcagca gtgggttagt ggttggcgat taaatgctga ctcagtattg    1500
tggggggggcc ataaagttttt catggtgaaa cctgaagagc cttttcagcc agttaaggaa  1560
gcgactcaac tcatgaatta g                                              1581
```

<210> SEQ ID NO 16
<211> LENGTH: 526
<212> TYPE: PRT
<213> ORGANISM: Artificial sequence
<220> FEATURE:
<223> OTHER INFORMATION: Synthetic

<400> SEQUENCE: 16

```
Met Cys Arg Ala Ile Ser Leu Arg Arg Leu Leu Leu Leu Leu Gln
  1               5                  10                  15

Leu Ser Gln Leu Leu Ala Val Thr Gln Gly Val Ser Lys Gly Glu Glu
             20                  25                  30

Val Ile Lys Glu Phe Met Arg Phe Lys Val Arg Met Glu Gly Ser Met
         35                  40                  45

Asn Gly His Glu Phe Glu Ile Glu Gly Glu Gly Glu Gly Arg Pro Tyr
     50                  55                  60
```

-continued

```
Glu Gly Thr Gln Thr Ala Lys Leu Lys Val Thr Lys Gly Gly Pro Leu
 65                  70                  75                  80

Pro Phe Ala Trp Asp Ile Leu Ser Pro Gln Phe Met Tyr Gly Ser Lys
                 85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140

Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
                165                 170                 175

Tyr Pro Arg Asp Gly Val Leu Lys Gly Glu Ile His Gln Ala Leu Lys
            180                 185                 190

Leu Lys Asp Gly Gly His Tyr Leu Val Glu Phe Lys Thr Ile Tyr Met
        195                 200                 205

Ala Lys Lys Pro Val Gln Leu Pro Gly Tyr Tyr Tyr Val Asp Thr Lys
    210                 215                 220

Leu Asp Ile Thr Ser His Asn Glu Asp Tyr Thr Ile Val Glu Gln Tyr
225                 230                 235                 240

Glu Arg Ser Glu Gly Arg His His Leu Phe Leu Tyr Gly Met Asp Glu
                245                 250                 255

Leu Tyr Lys Lys Leu Phe Trp Ala Leu Val Val Ala Gly Val Leu
            260                 265                 270

Phe Cys Tyr Gly Leu Leu Val Thr Val Ala Leu Cys Val Ile Trp Val
        275                 280                 285

Arg Ser Gly Glu Ser Leu Phe Lys Gly Pro Arg Asp Tyr Asn Pro Ile
    290                 295                 300

Ser Ser Thr Ile Cys His Leu Thr Asn Glu Ser Asp Gly His Thr Thr
305                 310                 315                 320

Ser Leu Tyr Gly Ile Gly Phe Gly Pro Phe Ile Ile Thr Asn Lys His
                325                 330                 335

Leu Phe Arg Arg Asn Asn Gly Thr Leu Leu Val Gln Ser Leu His Gly
            340                 345                 350

Val Phe Lys Val Lys Asn Thr Thr Thr Leu Gln Gln His Leu Ile Asp
        355                 360                 365

Gly Arg Asp Met Ile Ile Ile Arg Met Pro Lys Asp Phe Pro Pro Phe
    370                 375                 380

Pro Gln Lys Leu Lys Phe Arg Glu Pro Gln Arg Glu Glu Arg Ile Cys
385                 390                 395                 400

Leu Val Thr Thr Asn Phe Gln Thr Lys Ser Met Ser Ser Met Val Ser
                405                 410                 415

Asp Thr Ser Cys Thr Phe Pro Ser Ser Asp Gly Ile Phe Trp Lys His
            420                 425                 430

Trp Ile Gln Thr Lys Asp Gly Gln Cys Gly Ser Pro Leu Val Ser Thr
        435                 440                 445

Arg Asp Gly Phe Ile Val Gly Ile His Ser Ala Ser Asn Phe Thr Asn
    450                 455                 460

Thr Asn Asn Tyr Phe Thr Ser Val Pro Lys Asn Phe Met Glu Leu Leu
465                 470                 475                 480

Thr Asn Gln Glu Ala Gln Gln Trp Val Ser Gly Trp Arg Leu Asn Ala
```

485                 490                 495
Asp Ser Val Leu Trp Gly Gly His Lys Val Phe Met Val Lys Pro Glu
                500                 505                 510
Glu Pro Phe Gln Pro Val Lys Glu Ala Thr Gln Leu Met Asn
            515                 520                 525

<210> SEQ ID NO 17
<211> LENGTH: 2277
<212> TYPE: DNA
<213> ORGANISM: Artificial sequence
<220> FEATURE:
<223> OTHER INFORMATION: Synthetic

<400> SEQUENCE: 17

| | | | | | |
|---|---|---|---|---|---|
| atgtgccgag | ccatctctct | taggcgcttg | ctgctgctgc | tgctgcagct | gtcacaactc | 60 |
| ctagctgtca | ctcaagggaa | gacgctggtg | ctggggaagg | aaggggaatc | agcagaactg | 120 |
| ccctgcgaga | gttcccagaa | gaagatcaca | gtcttcacct | ggaagttctc | tgaccagagg | 180 |
| aagattctgg | ggcagcatgg | caaaggtgta | ttaattagag | gaggttcgcc | ttcgcagttt | 240 |
| gatcgttttg | attccaaaaa | agggcatgg | gagaaaggat | cgtttcctct | catcatcaat | 300 |
| aaacttaaga | tggaagactc | tcagacttat | atctgtgagc | tggagaacag | gaaagaggag | 360 |
| gtggagttgt | gggtgttcaa | agtgaccttc | agtccgggta | ccagcctgtt | gcaagggcag | 420 |
| agcctgaccc | tgaccttgga | tagcaactct | aaggtctcta | ccccttgac | agagtgcaaa | 480 |
| cacaaaaagg | gtaaagttgt | cagtggttcc | aaagttctct | ccatgtccaa | cctaagggtt | 540 |
| caggacagcg | acttctggaa | ctgcaccgtg | accctggacc | agaaaaagaa | ctggttcggc | 600 |
| atgacactct | cagtgctggg | ttttcagagc | acagctatca | cggcctataa | gagtgaggga | 660 |
| gagtcagcgg | agttctcctt | cccactcaac | tttgcagagg | aaaacgggtg | gggagagctg | 720 |
| atgtggaagg | cagagaagga | ttcttttcttc | cagccctgga | tctccttctc | cataaagaac | 780 |
| aaagaggtgt | ccgtacaaaa | gtccaccaaa | gacctcaagc | tccagctgaa | ggaaacgctc | 840 |
| ccactcaccc | tcaagatacc | ccaggtctcg | cttcagtttg | ctggttctgg | caacctgact | 900 |
| ctgactctgg | acaaagggac | actgcatcag | gaagtgaacc | tggtggtgat | gaaagtggct | 960 |
| cagctcaaca | atactttgac | ctgtgaggtg | atgggaccta | cctctcccaa | gatgagactg | 1020 |
| accctgaagc | aggagaacca | ggaggccagg | gtctctgagg | agcagaaagt | agttcaagtg | 1080 |
| gtggcccctg | agacagggct | gtggcagtgt | ctactgagtg | aaggtgataa | ggtcaagatg | 1140 |
| gactccagga | tccaggtttt | atccagaggg | aagcttttt | gggcactggt | cgtggttgct | 1200 |
| ggagtcctgt | tttgttatgg | cttgctagtg | acagtggctc | tttgtgttga | aaacctgtat | 1260 |
| tttcagggta | tgtctagatt | agataaaagt | aaagtgatta | acagcgcatt | agagctgctt | 1320 |
| aatgaggtcg | gaatcgaagg | tttaacaacc | cgtaaactcg | cccagaagct | aggtgtagag | 1380 |
| cagcctacat | tgtattggca | tgtaaaaaat | aagcgggctt | tgctcgacgc | cttagccatt | 1440 |
| gagatgttag | ataggcacca | tactcacttt | tgccctttag | aaggggaaag | ctggcaagat | 1500 |
| ttttttacgta | ataacgctaa | agttttaga | tgtgcttac | taagtcatcg | cgatggagca | 1560 |
| aaagtacatt | taggtacacg | gcctacagaa | aaacagtatg | aaactctcga | aaatcaatta | 1620 |
| gccttttttat | gccaacaagg | ttttttcacta | gagaatgcat | tatatgcact | cagcgctgtg | 1680 |
| gggcatttta | ctttaggttg | cgtattggaa | gatcaagagc | atcaagtcgc | taaagaagaa | 1740 |
| agggaaacac | ctactactga | tagtatgccg | ccattattac | gacaagctat | cgaattattt | 1800 |
| gatcaccaag | gtgcagagcc | agccttctta | ttcggccttg | aattgatcat | atgcggatta | 1860 |

```
gaaaaacaac ttaaatgtga aagtgggtcc gcgtacagcc gcgcgcgtac gaaaaacaat   1920
tacgggtcta ccatcgaggg cctgctcgat ctcccggacg acgacgcccc cgaagaggcg   1980
gggctggcgg ctccgcgcct gtcctttctc cccgcgggac acacgcgcag actgtcgacg   2040 gccccccga ccgatgtcag cctgggggac gagctccact tagacggcga ggacgtggcg   2100
atggcgcatg ccgacgcgct agacgatttc gatctggaca tgttggggga cggggattcc   2160
ccgggtccgg gatttacccc ccacgactcc gccccctacg cgctctctga tatgccgac    2220 ttcgagtttg agcagatgtt taccgatgcc cttggaattg acgagtacgg tgggtag      2277
```

<210> SEQ ID NO 18
<211> LENGTH: 758
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (423)..(423)
<223> OTHER INFORMATION: Xaa is Gly, Ala, Glu, Leu, Ser, Tyr, or Lys

<400> SEQUENCE: 18

Met Cys Arg Ala Ile Ser Leu Arg Arg Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
    50                  55                  60

Gln His Gly Lys Gly Val Leu Ile Arg Gly Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
            100                 105                 110

Glu Leu Glu Asn Arg Lys Glu Glu Val Glu Leu Trp Val Phe Lys Val
        115                 120                 125

Thr Phe Ser Pro Gly Thr Ser Leu Leu Gln Gly Gln Ser Leu Thr Leu
    130                 135                 140

Thr Leu Asp Ser Asn Ser Lys Val Ser Asn Pro Leu Thr Glu Cys Lys
145                 150                 155                 160

His Lys Lys Gly Lys Val Val Ser Gly Ser Lys Val Leu Ser Met Ser
                165                 170                 175

Asn Leu Arg Val Gln Asp Ser Asp Phe Trp Asn Cys Thr Val Thr Leu
            180                 185                 190

Asp Gln Lys Lys Asn Trp Phe Gly Met Thr Leu Ser Val Leu Gly Phe
        195                 200                 205

Gln Ser Thr Ala Ile Thr Ala Tyr Lys Ser Glu Gly Glu Ser Ala Glu
    210                 215                 220

Phe Ser Phe Pro Leu Asn Phe Ala Glu Glu Asn Gly Trp Gly Glu Leu
225                 230                 235                 240

Met Trp Lys Ala Glu Lys Asp Ser Phe Phe Gln Pro Trp Ile Ser Phe
                245                 250                 255

Ser Ile Lys Asn Lys Glu Val Ser Val Gln Lys Ser Thr Lys Asp Leu
            260                 265                 270

```
Lys Leu Gln Leu Lys Glu Thr Leu Pro Leu Thr Leu Lys Ile Pro Gln
            275                 280                 285

Val Ser Leu Gln Phe Ala Gly Ser Gly Asn Leu Thr Leu Thr Leu Asp
        290                 295                 300

Lys Gly Thr Leu His Gln Glu Val Asn Leu Val Val Met Lys Val Ala
305                 310                 315                 320

Gln Leu Asn Asn Thr Leu Thr Cys Glu Val Met Gly Pro Thr Ser Pro
                325                 330                 335

Lys Met Arg Leu Thr Leu Lys Gln Glu Asn Gln Glu Ala Arg Val Ser
            340                 345                 350

Glu Glu Gln Lys Val Val Gln Val Ala Pro Glu Thr Gly Leu Trp
        355                 360                 365

Gln Cys Leu Leu Ser Glu Gly Asp Lys Val Lys Met Asp Ser Arg Ile
    370                 375                 380

Gln Val Leu Ser Arg Gly Lys Leu Phe Trp Ala Leu Val Val Ala
385                 390                 395                 400

Gly Val Leu Phe Cys Tyr Gly Leu Leu Val Thr Val Ala Leu Cys Val
                405                 410                 415

Glu Asn Leu Tyr Phe Gln Xaa Met Ser Arg Leu Asp Lys Ser Lys Val
            420                 425                 430

Ile Asn Ser Ala Leu Glu Leu Leu Asn Glu Val Gly Ile Glu Gly Leu
        435                 440                 445

Thr Thr Arg Lys Leu Ala Gln Lys Leu Gly Val Glu Gln Pro Thr Leu
    450                 455                 460

Tyr Trp His Val Lys Asn Lys Arg Ala Leu Leu Asp Ala Leu Ala Ile
465                 470                 475                 480

Glu Met Leu Asp Arg His His Thr His Phe Cys Pro Leu Glu Gly Glu
                485                 490                 495

Ser Trp Gln Asp Phe Leu Arg Asn Asn Ala Lys Ser Phe Arg Cys Ala
            500                 505                 510

Leu Leu Ser His Arg Asp Gly Ala Lys Val His Leu Gly Thr Arg Pro
        515                 520                 525

Thr Glu Lys Gln Tyr Glu Thr Leu Glu Asn Gln Leu Ala Phe Leu Cys
    530                 535                 540

Gln Gln Gly Phe Ser Leu Glu Asn Ala Leu Tyr Ala Leu Ser Ala Val
545                 550                 555                 560

Gly His Phe Thr Leu Gly Cys Val Leu Glu Asp Gln Glu His Gln Val
                565                 570                 575

Ala Lys Glu Glu Arg Glu Thr Pro Thr Thr Asp Ser Met Pro Pro Leu
            580                 585                 590

Leu Arg Gln Ala Ile Glu Leu Phe Asp His Gln Gly Ala Glu Pro Ala
        595                 600                 605

Phe Leu Phe Gly Leu Glu Leu Ile Ile Cys Gly Leu Glu Lys Gln Leu
    610                 615                 620

Lys Cys Glu Ser Gly Ser Ala Tyr Ser Arg Ala Arg Thr Lys Asn Asn
625                 630                 635                 640

Tyr Gly Ser Thr Ile Glu Gly Leu Leu Asp Leu Pro Asp Asp Ala
                645                 650                 655

Pro Glu Glu Ala Gly Leu Ala Ala Pro Arg Leu Ser Phe Leu Pro Ala
            660                 665                 670

Gly His Thr Arg Arg Leu Ser Thr Ala Pro Pro Thr Asp Val Ser Leu
        675                 680                 685
```

```
Gly Asp Glu Leu His Leu Asp Gly Glu Asp Val Ala Met Ala His Ala
        690                 695                 700
Asp Ala Leu Asp Asp Phe Asp Leu Asp Met Leu Gly Asp Gly Asp Ser
705                 710                 715                 720
Pro Gly Pro Gly Phe Thr Pro His Asp Ser Ala Pro Tyr Gly Ala Leu
                725                 730                 735
Asp Met Ala Asp Phe Glu Phe Glu Gln Met Phe Thr Asp Ala Leu Gly
                740                 745                 750
Ile Asp Glu Tyr Gly Gly
        755

<210> SEQ ID NO 19
<211> LENGTH: 2295
<212> TYPE: DNA
<213> ORGANISM: Artificial sequence
<220> FEATURE:
<223> OTHER INFORMATION: Synthetic

<400> SEQUENCE: 19
atgtgccgag ccatctctct taggcgcttg ctgctgctgc tgctgcagct gtcacaactc      60
ctagctgtca ctcaagggaa gacgctggtc ctggggaagg aagggggaatc agcagaactg     120 ccctgcgaga gttcccagaa gaagatcaca gtcttcacct ggaagttctc tgaccagagg     180
aagattctgg gcagcatgg caaaggtgta ttaattagag gaggttcgcc ttcgcagttt      240
gatcgttttg attccaaaaa agggcatgg gagaaaggat cgtttcctct catcatcaat      300
aaacttaaga tggaagactc tcagacttat atctgtgagc tggagaacag gaaagaggag    360
gtggagttgt gggtgttcaa agtgaccttc agtccgggta ccagcctgtt gcaagggcag    420
agcctgaccc tgaccttgga tagcaactct aaggtctcta ccccttgac agagtgcaaa     480 cacaaaaagg gtaaagttgt cagtggttcc aaagttctct ccatgtccaa cctaagggtt    540
caggacagcg acttctggaa ctgcaccgtg accctggacc agaaaaagaa ctggttcggc    600
atgacactct cagtgctggg ttttcagagc acagctatca cggcctataa gagtgaggga    660
gagtcagcgg agttctcctt cccactcaac tttgcagagg aaaacgggtg gggagagctg    720
atgtggaagg cagagaagga ttcttttctc cagcccctgga tctccttctc cataaagaac   780
aaagaggtgt ccgtacaaaa gtccaccaaa gacctcaagc tccagctgaa ggaaacgctc   840
ccactcaccc tcaagatacc ccaggtctcg cttcagtttg ctggttctgg caacctgact    900
ctgactctgg acaaagggac actgcatcag gaagtgaacc tggtggtgat gaaagtggct   960
cagctcaaca atactttgac ctgtgaggtg atgggaccta cctctcccaa gatgagactg   1020
accctgaagc aggagaacca ggaggccagg gtctctgagg agcagaaagt agttcaagtg   1080 gtggccctg agacagggct gtggcagtgt ctactgagtg aaggtgataa ggtcaagatg    1140
gactccagga tccaggtttt atccagaggg aagcttttt gggcactggt cgtggttgct    1200
ggagtcctgt tttgttatgg cttgctagtg acagtggctc tttgtgttat ctgggtaaga    1260
tctggtgaaa acctgtattt tcagggtatg tctagattag ataaaagtaa agtgattaac    1320
agcgcattag agctgcttaa tgaggtcgga atcgaaggtt taacaacccg taaactcgcc   1380
cagaagctag tgtagagca gcctacattg tattggcatg taaaaataa gcgggctttg     1440 ctcgacgcct tagccattga gatgttagat aggcaccata ctcacttttg ccctttagaa   1500
ggggaaagct ggcaagattt ttacgtaat aacgctaaaa gttttagatg tgctttacta    1560
agtcatcgcg atggagcaaa agtacattta ggtacacggc ctacagaaaa acagtatgaa   1620
```

-continued

```
actctcgaaa atcaattagc cttttttatgc caacaaggtt tttcactaga gaatgcatta    1680
tatgcactca gcgctgtggg gcattttact ttaggttgcg tattggaaga tcaagagcat    1740
caagtcgcta agaagaaag ggaaacacct actactgata gtatgccgcc attattacga    1800
caagctatcg aattatttga tcaccaaggt gcagagccag ccttcttatt cggccttgaa    1860
ttgatcatat gcggattaga aaacaacctt aaatgtgaaa gtgggtccgc gtacagccgc    1920
gcgcgtacga aaacaatta cgggtctacc atcgagggcc tgctcgatct cccgacgac     1980
gacgccccg aagaggcggg gctggcggct ccgcgcctgt cctttctccc cgcgggacac    2040
acgcgcagac tgtcgacggc cccccgacc gatgtcagcc tggggacga gctccactta    2100
gacggcgagg acgtggcgat ggcgcatgcc gacgcgctag acgatttcga tctggacatg    2160
ttggggacg gggattcccc gggtccggga tttaccccccc acgactccgc ccctacggc   2220
gctctggata tggccgactt cgagtttgag cagatgttta ccgatgccct tggaattgac  2280
gagtacggtg ggtag                                                    2295
```

<210> SEQ ID NO 20
<211> LENGTH: 764
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (429)..(429)
<223> OTHER INFORMATION: Xaa is Gly, Ala, Glu, Leu, Ser, Tyr, or Lys

<400> SEQUENCE: 20

Met Cys Arg Ala Ile Ser Leu Arg Arg Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
    50                  55                  60

Gln His Gly Lys Gly Val Leu Ile Arg Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
            100                 105                 110

Glu Leu Glu Asn Arg Lys Glu Glu Val Glu Leu Trp Val Phe Lys Val
        115                 120                 125

Thr Phe Ser Pro Gly Thr Ser Leu Leu Gln Gly Gln Ser Leu Thr Leu
    130                 135                 140

Thr Leu Asp Ser Asn Ser Lys Val Ser Asn Pro Leu Thr Glu Cys Lys
145                 150                 155                 160

His Lys Lys Gly Lys Val Val Ser Gly Ser Lys Val Leu Ser Met Ser
                165                 170                 175

Asn Leu Arg Val Gln Asp Ser Asp Phe Trp Asn Cys Thr Val Thr Leu
            180                 185                 190

Asp Gln Lys Lys Asn Trp Phe Gly Met Thr Leu Ser Val Leu Gly Phe
        195                 200                 205

Gln Ser Thr Ala Ile Thr Ala Tyr Lys Ser Glu Gly Glu Ser Ala Glu
    210                 215                 220

```
Phe Ser Phe Pro Leu Asn Phe Ala Glu Glu Asn Gly Trp Gly Glu Leu
225                 230                 235                 240

Met Trp Lys Ala Glu Lys Asp Ser Phe Phe Gln Pro Trp Ile Ser Phe
                245                 250                 255

Ser Ile Lys Asn Lys Glu Val Ser Val Gln Lys Ser Thr Lys Asp Leu
            260                 265                 270

Lys Leu Gln Leu Lys Glu Thr Leu Pro Leu Thr Leu Lys Ile Pro Gln
        275                 280                 285

Val Ser Leu Gln Phe Ala Gly Ser Gly Asn Leu Thr Leu Thr Leu Asp
290                 295                 300

Lys Gly Thr Leu His Gln Glu Val Asn Leu Val Val Met Lys Val Ala
305                 310                 315                 320

Gln Leu Asn Asn Thr Leu Thr Cys Glu Val Met Gly Pro Thr Ser Pro
                325                 330                 335

Lys Met Arg Leu Thr Leu Lys Gln Glu Asn Gln Glu Ala Arg Val Ser
            340                 345                 350

Glu Glu Gln Lys Val Val Gln Val Val Ala Pro Glu Thr Gly Leu Trp
        355                 360                 365

Gln Cys Leu Leu Ser Glu Gly Asp Lys Val Lys Met Asp Ser Arg Ile
370                 375                 380

Gln Val Leu Ser Arg Gly Lys Leu Phe Trp Ala Leu Val Val Ala
385                 390                 395                 400

Gly Val Leu Phe Cys Tyr Gly Leu Leu Val Thr Val Ala Leu Cys Val
                405                 410                 415

Ile Trp Val Arg Ser Gly Glu Asn Leu Tyr Phe Gln Xaa Met Ser Arg
            420                 425                 430

Leu Asp Lys Ser Lys Val Ile Asn Ser Ala Leu Glu Leu Leu Asn Glu
            435                 440                 445

Val Gly Ile Glu Gly Leu Thr Thr Arg Lys Leu Ala Gln Lys Leu Gly
450                 455                 460

Val Glu Gln Pro Thr Leu Tyr Trp His Val Lys Asn Lys Arg Ala Leu
465                 470                 475                 480

Leu Asp Ala Leu Ala Ile Glu Met Leu Asp Arg His His Thr His Phe
                485                 490                 495

Cys Pro Leu Glu Gly Glu Ser Trp Gln Asp Phe Leu Arg Asn Asn Ala
            500                 505                 510

Lys Ser Phe Arg Cys Ala Leu Leu Ser His Arg Asp Gly Ala Lys Val
        515                 520                 525

His Leu Gly Thr Arg Pro Thr Glu Lys Gln Tyr Glu Thr Leu Glu Asn
530                 535                 540

Gln Leu Ala Phe Leu Cys Gln Gln Gly Phe Ser Leu Glu Asn Ala Leu
545                 550                 555                 560

Tyr Ala Leu Ser Ala Val Gly His Phe Thr Leu Gly Cys Val Leu Glu
                565                 570                 575

Asp Gln Glu His Gln Val Ala Lys Glu Glu Arg Glu Thr Pro Thr Thr
            580                 585                 590

Asp Ser Met Pro Pro Leu Leu Arg Gln Ala Ile Glu Leu Phe Asp His
        595                 600                 605

Gln Gly Ala Glu Pro Ala Phe Leu Phe Gly Leu Glu Leu Ile Ile Cys
610                 615                 620

Gly Leu Glu Lys Gln Leu Lys Cys Glu Ser Gly Ser Ala Tyr Ser Arg
625                 630                 635                 640
```

| | | | | | | | | | | | | |
|---|---|---|---|---|---|---|---|---|---|---|---|---|
|Ala|Arg|Thr|Lys|Asn|Asn|Tyr|Gly|Ser|Thr|Ile|Glu|Gly|Leu|Leu|Asp|
| | | | |645| | | |650| | | |655| | |

Ala Arg Thr Lys Asn Asn Tyr Gly Ser Thr Ile Glu Gly Leu Leu Asp
                     645                 650                 655

Leu Pro Asp Asp Ala Pro Glu Glu Ala Gly Leu Ala Ala Pro Arg
            660                 665                 670

Leu Ser Phe Leu Pro Ala Gly His Thr Arg Arg Leu Ser Thr Ala Pro
            675                 680                 685

Pro Thr Asp Val Ser Leu Gly Asp Glu Leu His Leu Asp Gly Glu Asp
            690                 695                 700

Val Ala Met Ala His Ala Asp Ala Leu Asp Asp Phe Asp Leu Asp Met
705                 710                 715                 720

Leu Gly Asp Gly Asp Ser Pro Gly Pro Gly Phe Thr Pro His Asp Ser
                725                 730                 735

Ala Pro Tyr Gly Ala Leu Asp Met Ala Asp Phe Glu Phe Glu Gln Met
            740                 745                 750

Phe Thr Asp Ala Leu Gly Ile Asp Glu Tyr Gly Gly
            755                 760

<210> SEQ ID NO 21
<211> LENGTH: 1956
<212> TYPE: DNA
<213> ORGANISM: Artificial sequence
<220> FEATURE:
<223> OTHER INFORMATION: Synthetic

<400> SEQUENCE: 21

```
atgtgccgag ccatctctct taggcgcttg ctgctgctgc tgctgcagct gtcacaactc      60
ctagctgtca ctcaagggaa gacgctggtg ctggggaagg aagggggaatc agcagaactg    120
ccctgcgaga gttcccagaa gaagatcaca gtcttcacct ggaagttctc tgaccagagg    180
aagattctgg gcagcatgg caaaggtgta ttaattagag gaggttcgcc ttcgcagttt      240
gatcgttttg attccaaaaa aggggcatgg gagaaaggat cgtttcctct catcatcaat    300
aaacttaaga tggaagactc tcagacttat atctgtgagc tggagaacag aaagaggag    360
gtggagttgt gggtgttcaa agtgaccttc agtccgggta ccagcctgtt gcaagggcag    420
agcctgaccc tgaccttgga tagcaactct aaggtctcta ccccttgac agagtgcaaa    480
cacaaaaagg gtaaagttgt cagtggttcc aaagttctct ccatgtccaa cctaagggtt    540
caggacagcg acttctggaa ctgcaccgtg accctggacc agaaaaagaa ctggttcggc    600
atgacactct cagtgctggg ttttcagagc acagctatca cggcctataa gagtgaggga    660
gagtcagcgg agttctcctt cccactcaac tttgcagagg aaaacgggtg gggagagctg    720
atgtggaagg cagagaagga ttcttcttc cagccctgga tctccttctc cataaagaac    780
aaagaggtgt ccgtacaaaa gtccaccaaa gacctcaagc tccagctgaa ggaaacgctc    840
ccactcaccc tcaagatacc ccaggtctcg cttcagtttg ctggttctgg caacctgact    900
ctgactctgg acaagggac actgcatcag gaagtgaacc tggtggtgat gaaagtggct    960
cagctcaaca atactttgac ctgtgaggtg atgggaccta cctctcccaa gatgagactg   1020
acccctgaagc aggagaacca ggaggccagg gtctctgagg agcagaaagt agttcaagtg   1080
gtggcccctg agacagggct gtggcagtgt ctactgagtg aagtgataaa ggtcaagatg   1140
gactccagga tccaggtttt atccagaggg aagcttttt gggcactggt cgtggttgct   1200
ggagtcctgt tttgttatgg cttgctagtg acagtggctc tttgtgttga gagcttgttt   1260
aaggggccgc gtgattacaa cccgatatcg agcaccattt gtcatttgac gaatgaatct   1320
gatgggcaca caacatcgtt gtatggtatt ggatttggtc ccttcatcat tacaaacaag   1380
```

```
cacttgttta gaagaaataa tggaacactg ttggtccaat cactacatgg tgtattcaag    1440
gtcaagaaca ccacgacttt gcaacaacac ctcattgatg ggagggacat gataattatt    1500
cgcatgccta aggatttccc accatttcct caaaagctga aatttagaga gccacaaagg    1560
gaagagcgca tatgtcttgt gacaaccaac ttccaaacta agagcatgtc tagcatggtg    1620
tcagacacta gttgcacatt cccttcatct gatggcatat tctggaagca ttggattcaa    1680
accaaggatg ggcagtgtgg cagtccatta gtatcaacta gagatgggtt cattgttggt    1740
atacactcag catcgaattt caccaacaca acaattatt tcacaagcgt gccgaaaaac    1800
ttcatggaat gttgacaaa tcaggaggcg cagcagtggg ttagtggttg gcgattaaat    1860
gctgactcag tattgtgggg gggccataaa gttttcatgg tgaaacctga agagcctttt    1920
cagccagtta aggaagcgac tcaactcatg aattag                             1956
```

<210> SEQ ID NO 22
<211> LENGTH: 651
<212> TYPE: PRT
<213> ORGANISM: Artificial sequence
<220> FEATURE:
<223> OTHER INFORMATION: Synthetic

<400> SEQUENCE: 22

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
    50                  55                  60

Gln His Gly Lys Gly Val Leu Ile Arg Gly Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
            100                 105                 110

Glu Leu Glu Asn Arg Lys Glu Glu Val Glu Leu Trp Val Phe Lys Val
        115                 120                 125

Thr Phe Ser Pro Gly Thr Ser Leu Leu Gln Gly Gln Ser Leu Thr Leu
    130                 135                 140

Thr Leu Asp Ser Asn Ser Lys Val Ser Asn Pro Leu Thr Glu Cys Lys
145                 150                 155                 160

His Lys Lys Gly Lys Val Val Ser Gly Ser Lys Val Leu Ser Met Ser
                165                 170                 175

Asn Leu Arg Val Gln Asp Ser Asp Phe Trp Asn Cys Thr Val Thr Leu
            180                 185                 190

Asp Gln Lys Lys Asn Trp Phe Gly Met Thr Leu Ser Val Leu Gly Phe
        195                 200                 205

Gln Ser Thr Ala Ile Thr Ala Tyr Lys Ser Glu Gly Glu Ser Ala Glu
    210                 215                 220

Phe Ser Phe Pro Leu Asn Phe Ala Glu Glu Asn Gly Trp Gly Glu Leu
225                 230                 235                 240

Met Trp Lys Ala Glu Lys Asp Ser Phe Phe Gln Pro Trp Ile Ser Phe
                245                 250                 255
```

-continued

Ser Ile Lys Asn Lys Glu Val Ser Val Gln Lys Ser Thr Lys Asp Leu
            260                 265                 270

Lys Leu Gln Leu Lys Glu Thr Leu Pro Leu Thr Leu Lys Ile Pro Gln
        275                 280                 285

Val Ser Leu Gln Phe Ala Gly Ser Gly Asn Leu Thr Leu Thr Leu Asp
    290                 295                 300

Lys Gly Thr Leu His Gln Glu Val Asn Leu Val Val Met Lys Val Ala
305                 310                 315                 320

Gln Leu Asn Asn Thr Leu Thr Cys Glu Val Met Gly Pro Thr Ser Pro
                325                 330                 335

Lys Met Arg Leu Thr Leu Lys Gln Glu Asn Gln Glu Ala Arg Val Ser
            340                 345                 350

Glu Glu Gln Lys Val Val Gln Val Val Ala Pro Glu Thr Gly Leu Trp
        355                 360                 365

Gln Cys Leu Leu Ser Glu Gly Asp Lys Val Lys Met Asp Ser Arg Ile
    370                 375                 380

Gln Val Leu Ser Arg Gly Lys Leu Phe Trp Ala Leu Val Val Val Ala
385                 390                 395                 400

Gly Val Leu Phe Cys Tyr Gly Leu Leu Val Thr Val Ala Leu Cys Val
                405                 410                 415

Glu Ser Leu Phe Lys Gly Pro Arg Asp Tyr Asn Pro Ile Ser Ser Thr
            420                 425                 430

Ile Cys His Leu Thr Asn Glu Ser Asp Gly His Thr Thr Ser Leu Tyr
        435                 440                 445

Gly Ile Gly Phe Gly Pro Phe Ile Ile Thr Asn Lys His Leu Phe Arg
    450                 455                 460

Arg Asn Asn Gly Thr Leu Leu Val Gln Ser Leu His Gly Val Phe Lys
465                 470                 475                 480

Val Lys Asn Thr Thr Thr Leu Gln Gln His Leu Ile Asp Gly Arg Asp
                485                 490                 495

Met Ile Ile Ile Arg Met Pro Lys Asp Phe Pro Pro Phe Pro Gln Lys
            500                 505                 510

Leu Lys Phe Arg Glu Pro Gln Arg Glu Glu Arg Ile Cys Leu Val Thr
        515                 520                 525

Thr Asn Phe Gln Thr Lys Ser Met Ser Ser Met Val Ser Asp Thr Ser
    530                 535                 540

Cys Thr Phe Pro Ser Ser Asp Gly Ile Phe Trp Lys His Trp Ile Gln
545                 550                 555                 560

Thr Lys Asp Gly Gln Cys Gly Ser Pro Leu Val Ser Thr Arg Asp Gly
                565                 570                 575

Phe Ile Val Gly Ile His Ser Ala Ser Asn Phe Thr Asn Thr Asn Asn
            580                 585                 590

Tyr Phe Thr Ser Val Pro Lys Asn Phe Met Glu Leu Leu Thr Asn Gln
        595                 600                 605

Glu Ala Gln Gln Trp Val Ser Gly Trp Arg Leu Asn Ala Asp Ser Val
    610                 615                 620

Leu Trp Gly Gly His Lys Val Phe Met Val Lys Pro Glu Glu Pro Phe
625                 630                 635                 640

Gln Pro Val Lys Glu Ala Thr Gln Leu Met Asn
                645                 650

<210> SEQ ID NO 23
<211> LENGTH: 1974
<212> TYPE: DNA

<213> ORGANISM: Artificial sequence
<220> FEATURE:
<223> OTHER INFORMATION: Synthetic

<400> SEQUENCE: 23

```
atgtgccgag ccatctctct taggcgcttg ctgctgctgc tgctgcagct gtcacaactc      60
ctagctgtca ctcaagggaa gacgctggtg ctggggaagg aaggggaatc agcagaactg     120
ccctgcgaga gttcccagaa gaagatcaca gtcttcacct ggaagttctc tgaccagagg     180
aagattctgg ggcagcatgg caaaggtgta ttaattagag gaggttcgcc ttcgcagttt     240
gatcgttttg attccaaaaa aggggcatgg gagaaaggat cgtttcctct catcatcaat     300
aaacttaaga tggaagactc tcagacttat atctgtgagc tggagaacag gaaagaggag     360
gtggagttgt gggtgttcaa agtgaccttc agtccgggta ccagcctgtt gcaagggcag     420
agcctgaccc tgaccttgga tagcaactct aaggtctcta accccttgac agagtgcaaa     480
cacaaaaagg gtaaagttgt cagtggttcc aaagttctct ccatgtccaa cctaagggtt     540
caggacagcg acttctggaa ctgcaccgtg accctggacc agaaaaagaa ctggttcggc     600
atgacactct cagtgctggg ttttcagagc acagctatca cggcctataa gagtgaggga     660
gagtcagcgg agttctcctt cccactcaac tttgcagagg aaaacgggtg gggagagctg     720
atgtggaagg cagagaagga ttcttttctt cagccctgga tctccttctc cataaagaac     780
aaagaggtgt ccgtacaaaa gtccaccaaa gacctcaagc tccagctgaa ggaaacgctc     840
ccactcaccc tcaagatacc ccaggtctcg cttcagtttg ctggttctgg caacctgact     900
ctgactctgg acaaagggac actgcatcag gaagtgaacc tggtggtgat gaaagtggct     960
cagctcaaca atactttgac ctgtgaggtg atgggaccta cctctcccaa gatgagactg    1020
accctgaagc aggagaacca ggaggccagg gtctctgagg agcagaaagt agttcaagtg    1080
gtggcccctg agacagggct gtggcagtgt ctactgagtg aaggtgataa ggtcaagatg    1140
gactccagga tccaggtttt atccagaggg aagcttttttt gggcactggt cgtggttgct    1200
ggagtcctgt tttgttatgg cttgctagtg acagtggctc tttgtgttat ctgggtaaga    1260
tctggtgaga gcttgtttaa ggggccgcgt gattacaacc cgatatcgag caccatttgt    1320
catttgacga atgaatctga tgggcacaca acatcgttgt atggtattgg atttggtccc    1380
ttcatcatta caaacaagca cttgtttaga gaaataatg gaacactgtt ggtccaatca    1440
ctacatggtg tattcaaggt caagaacacc acgactttgc aacaacacct cattgatggg    1500
agggacatga taattattcg catgcctaag gatttcccac catttcctca aaagctgaaa    1560
tttagagagc acaaagggaa agagcgcata tgtcttgtga caaccaactt ccaaactaag    1620
agcatgtcta gcatggtgtc agacactagt tgcacattcc cttcatctga tggcatattc    1680
tggaagcatt ggattcaaac caaggatggg cagtgtggca gtccattagt atcaactaga    1740
gatgggttca ttgttggtat acactcagca tcgaatttca ccaacacaaa caattatttc    1800
acaagcgtgc cgaaaaactt catggaattg ttgacaaatc aggaggcgca gcagtgggtt    1860
agtggttggc gattaaatgc tgactcagta ttgtgggggg ccataaagt tttcatggtg    1920
aaacctgaag agcctttttca gccagttaag gaagcgactc aactcatgaa ttag          1974
```

<210> SEQ ID NO 24
<211> LENGTH: 657
<212> TYPE: PRT
<213> ORGANISM: Artificial sequence
<220> FEATURE:
<223> OTHER INFORMATION: Synthetic

<400> SEQUENCE: 24

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Lys Thr Leu Val Leu Gly
            20                  25                  30

Lys Glu Gly Glu Ser Ala Glu Leu Pro Cys Glu Ser Ser Gln Lys Lys
        35                  40                  45

Ile Thr Val Phe Thr Trp Lys Phe Ser Asp Gln Arg Lys Ile Leu Gly
    50                  55                  60

Gln His Gly Lys Gly Val Leu Ile Arg Gly Gly Ser Pro Ser Gln Phe
65                  70                  75                  80

Asp Arg Phe Asp Ser Lys Lys Gly Ala Trp Glu Lys Gly Ser Phe Pro
                85                  90                  95

Leu Ile Ile Asn Lys Leu Lys Met Glu Asp Ser Gln Thr Tyr Ile Cys
            100                 105                 110

Glu Leu Glu Asn Arg Lys Glu Glu Val Glu Leu Trp Val Phe Lys Val
        115                 120                 125

Thr Phe Ser Pro Gly Thr Ser Leu Leu Gln Gly Gln Ser Leu Thr Leu
    130                 135                 140

Thr Leu Asp Ser Asn Ser Lys Val Ser Asn Pro Leu Thr Glu Cys Lys
145                 150                 155                 160

His Lys Lys Gly Lys Val Val Ser Gly Ser Lys Val Leu Ser Met Ser
                165                 170                 175

Asn Leu Arg Val Gln Asp Ser Asp Phe Trp Asn Cys Thr Val Thr Leu
            180                 185                 190

Asp Gln Lys Lys Asn Trp Phe Gly Met Thr Leu Ser Val Leu Gly Phe
        195                 200                 205

Gln Ser Thr Ala Ile Thr Ala Tyr Lys Ser Glu Gly Glu Ser Ala Glu
    210                 215                 220

Phe Ser Phe Pro Leu Asn Phe Ala Glu Glu Asn Gly Trp Gly Glu Leu
225                 230                 235                 240

Met Trp Lys Ala Glu Lys Asp Ser Phe Phe Gln Pro Trp Ile Ser Phe
                245                 250                 255

Ser Ile Lys Asn Lys Glu Val Ser Val Gln Lys Ser Thr Lys Asp Leu
            260                 265                 270

Lys Leu Gln Leu Lys Glu Thr Leu Pro Leu Thr Leu Lys Ile Pro Gln
        275                 280                 285

Val Ser Leu Gln Phe Ala Gly Ser Gly Asn Leu Thr Leu Thr Leu Asp
    290                 295                 300

Lys Gly Thr Leu His Gln Glu Val Asn Leu Val Val Met Lys Val Ala
305                 310                 315                 320

Gln Leu Asn Asn Thr Leu Thr Cys Glu Val Met Gly Pro Thr Ser Pro
                325                 330                 335

Lys Met Arg Leu Thr Leu Lys Gln Glu Asn Gln Glu Ala Arg Val Ser
            340                 345                 350

Glu Glu Gln Lys Val Val Gln Val Val Ala Pro Glu Thr Gly Leu Trp
        355                 360                 365

Gln Cys Leu Leu Ser Glu Gly Asp Lys Val Lys Met Asp Ser Arg Ile
    370                 375                 380

Gln Val Leu Ser Arg Gly Lys Leu Phe Trp Ala Leu Val Val Val Ala
385                 390                 395                 400

Gly Val Leu Phe Cys Tyr Gly Leu Leu Val Thr Val Ala Leu Cys Val
```

```
                    405                 410                 415
Ile Trp Val Arg Ser Gly Glu Ser Leu Phe Lys Gly Pro Arg Asp Tyr
                420                 425                 430

Asn Pro Ile Ser Ser Thr Ile Cys His Leu Thr Asn Glu Ser Asp Gly
            435                 440                 445

His Thr Thr Ser Leu Tyr Gly Ile Gly Phe Gly Pro Phe Ile Ile Thr
    450                 455                 460

Asn Lys His Leu Phe Arg Arg Asn Asn Gly Thr Leu Leu Val Gln Ser
465                 470                 475                 480

Leu His Gly Val Phe Lys Val Lys Asn Thr Thr Thr Leu Gln Gln His
                485                 490                 495

Leu Ile Asp Gly Arg Asp Met Ile Ile Ile Arg Met Pro Lys Asp Phe
            500                 505                 510

Pro Pro Phe Pro Gln Lys Leu Lys Phe Arg Glu Pro Gln Arg Glu Glu
        515                 520                 525

Arg Ile Cys Leu Val Thr Thr Asn Phe Gln Thr Lys Ser Met Ser Ser
    530                 535                 540

Met Val Ser Asp Thr Ser Cys Thr Phe Pro Ser Ser Asp Gly Ile Phe
545                 550                 555                 560

Trp Lys His Trp Ile Gln Thr Lys Asp Gly Gln Cys Gly Ser Pro Leu
                565                 570                 575

Val Ser Thr Arg Asp Gly Phe Ile Val Gly Ile His Ser Ala Ser Asn
            580                 585                 590

Phe Thr Asn Thr Asn Asn Tyr Phe Thr Ser Val Pro Lys Asn Phe Met
        595                 600                 605

Glu Leu Leu Thr Asn Gln Glu Ala Gln Gln Trp Val Ser Gly Trp Arg
    610                 615                 620

Leu Asn Ala Asp Ser Val Leu Trp Gly Gly His Lys Val Phe Met Val
625                 630                 635                 640

Lys Pro Glu Glu Pro Phe Gln Pro Val Lys Glu Ala Thr Gln Leu Met
                645                 650                 655

Asn

<210> SEQ ID NO 25
<211> LENGTH: 2640
<212> TYPE: DNA
<213> ORGANISM: Artificial sequence
<220> FEATURE:
<223> OTHER INFORMATION: Synthetic

<400> SEQUENCE: 25
atgtgccgag ccatctctct taggcgcttg ctgctgctgc tgctgcagct gtcacaactc      60
ctagctgtca tcaagggat ggtgagcaag ggcgaggagg ataacatggc catcatcaag     120
gagttcatgc gcttcaaggt gcacatggag ggctccgtga acggccacga gttcgagatc     180
gagggcgagg gcgagggccg cccctacgag ggcacccaga ccgccaagct gaaggtgacc     240
aagggtggcc ccctgccctt cgcctgggac atcctgtccc ctcagttcat gtacggctcc     300
aaggcctacg tgaagcaccc cgccgacatc cccgactact tgaagctgtc cttccccgag     360
ggcttcaagt gggagcgcgt gatgaacttc gaggacggcg gcgtggtgac cgtgacccag     420
gactcctccc tgcaggacgg cgagttcatc tacaaggtga agctgcgcgg caccaacttc     480
ccctccgacg gccccgtaat gcagaagaag accatgggct gggaggcctc ctccgagcgg     540
atgtaccccg aggacggcgc cctgaagggc gagatcaagc agaggctgaa gctgaaggac     600
```

```
ggcggccact acgacgctga ggtcaagacc acctacaagg ccaagaagcc cgtgcagctg    660
cccggcgcct acaacgtcaa catcaagttg gacatcacct cccacaacga ggactacacc    720
atcgtggaac agtacgaacg cgccgagggc cgccactcca ccggcggcat ggacgagctg    780
tacaagaagc ttttttgggc actggtcgtg gttgctggag tcctgttttg ttatggcttg    840
ctagtgacag tggctctttg tgttgaaaac ctgtattttc agggtatgtc tagattagat    900
aaaagtaaag tgattaacag cgcattagag ctgcttaatg aggtcggaat cgaaggttta    960
acaacccgta aactcgccca aagctaggt gtagagcagc ctacattgta ttggcatgta   1020
aaaaataagc gggctttgct cgacgcctta gccattgaga tgttagatag caccatact   1080 cacttttgcc ctttagaagg ggaaagctgg caagatttt tacgtaataa cgctaaaagt   1140
tttagatgtg ctttactaag tcatcgcgat ggagcaaaag tacatttagg tacacggcct   1200
acagaaaaac agtatgaaac tctcgaaaat caattagcct ttttatgcca acaaggtttt   1260
tcactagaga atgcattata tgcactcagc gctgtggggc attttacttt aggttgcgta   1320
ttggaagatc aagagcatca agtcgctaaa gaagaaaggg aaacacctac tactgatagt   1380
atgccgccat tattacgaca agctatcgaa ttatttgatc accaaggtgc agagccagcc   1440
ttcttattcg gccttgaatt gatcatatgc ggattagaaa acaacttaa atgtgaaagt   1500 gggtccgcgt acagccgcgc gcgtacgaaa aacaattacg ggtctaccat cgagggcctg   1560
ctcgatctcc cggacgacga cgcccccgaa gaggcgcgggc tggcggctcc gcgcctgtcc   1620
tttctccccg cgggacacac gcgcagactg tcgacggccc cccgaccga tgtcagcctg   1680 ggggacgagc tccacttaga cggcgaggac gtggcgatgg cgcatgccga cgcgctagac   1740
gatttcgatc tggacatgtt gggggacggg gattccccgg tccgggatt taccccccac   1800 gactccgccc cctacggcgc tctggatatg gccgacttcg agtttgagca gatgtttacc   1860
gatgcccttg gaattgacga gtacggtgga ggtaccggcg gaggctccgg tggtggctct   1920
atggtgagca agggcgagga gctgttcacc ggggtggtgc ccatcctggt cgagctggac   1980
ggcgacgtaa acggccacaa gttcagcgtg aggggcgagg gcgagggcga tgccaccaac   2040
ggcaagctga ccctgaagtt catctgcacc accggcaagc tgcccgtgcc ctggcccacc   2100
ctcgtgacca cccctgagca cggcgtgcag tgcttcgccc gctaccccga ccacatgaag   2160
cagcacgact tcttcaagtc cgccatgccc gaaggctacg tccaggagcg caccatcttc   2220
ttcaaggacg acggcaccta caagacccgc gccgaggtga agttcgaggg cgacacccta   2280
gtgaaccgca tcgagctgaa gggcgtcgac ttcaaggagg acggcaacat cctggggcac   2340
aagctggagt acaacttcaa cagccacaac atctatatca tggccgtcaa gcagaagaac   2400
ggcatcaagg tgaacttcaa gatccgccac aacgtggagg acggcagcgt gcagctcgcc   2460
gaccactacc agcagaacac ccccatcggc gacggccccg tgctgctgcc cgacagccac   2520
tacctgagca cccagtccgt gctgagcaaa gaccccaacg agaagcgcga tcacatggtc   2580
ctgctggagt tccgcaccgc cgccgggatc actctcggca tggacgagct gtacaagtaa   2640
```

<210> SEQ ID NO 26
<211> LENGTH: 879
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (295)..(295)
<223> OTHER INFORMATION: Xaa is Gly, Ala, Glu, Leu, Ser, Tyr, or Lys

<400> SEQUENCE: 26

Met Cys Arg Ala Ile Ser Leu Arg Arg Leu Leu Leu Leu Leu Leu Gln
1               5                   10                  15

Leu Ser Gln Leu Leu Ala Val Thr Gln Gly Met Val Ser Lys Gly Glu
            20                  25                  30

Glu Asp Asn Met Ala Ile Ile Lys Glu Phe Met Arg Phe Lys Val His
        35                  40                  45

Met Glu Gly Ser Val Asn Gly His Glu Phe Glu Ile Glu Gly Glu Gly
    50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Met Tyr Gly Ser Lys Ala Tyr Val Lys His Pro Ala Asp Ile Pro Asp
            100                 105                 110

Tyr Leu Lys Leu Ser Phe Pro Glu Gly Phe Lys Trp Glu Arg Val Met
        115                 120                 125

Asn Phe Glu Asp Gly Gly Val Val Thr Val Thr Gln Asp Ser Ser Leu
130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
            180                 185                 190

Lys Gln Arg Leu Lys Leu Lys Asp Gly Gly His Tyr Asp Ala Glu Val
        195                 200                 205

Lys Thr Thr Tyr Lys Ala Lys Lys Pro Val Gln Leu Pro Gly Ala Tyr
210                 215                 220

Asn Val Asn Ile Lys Leu Asp Ile Thr Ser His Asn Glu Asp Tyr Thr
225                 230                 235                 240

Ile Val Glu Gln Tyr Glu Arg Ala Glu Gly Arg His Ser Thr Gly Gly
                245                 250                 255

Met Asp Glu Leu Tyr Lys Lys Leu Phe Trp Ala Leu Val Val Val Ala
            260                 265                 270

Gly Val Leu Phe Cys Tyr Gly Leu Leu Val Thr Val Ala Leu Cys Val
        275                 280                 285

Glu Asn Leu Tyr Phe Gln Xaa Met Ser Arg Leu Asp Lys Ser Lys Val
    290                 295                 300

Ile Asn Ser Ala Leu Glu Leu Leu Asn Glu Val Gly Ile Glu Gly Leu
305                 310                 315                 320

Thr Thr Arg Lys Leu Ala Gln Lys Leu Gly Val Glu Gln Pro Thr Leu
                325                 330                 335

Tyr Trp His Val Lys Asn Lys Arg Ala Leu Leu Asp Ala Leu Ala Ile
            340                 345                 350

Glu Met Leu Asp Arg His His Thr His Phe Cys Pro Leu Glu Gly Glu
        355                 360                 365

Ser Trp Gln Asp Phe Leu Arg Asn Asn Ala Lys Ser Phe Arg Cys Ala
    370                 375                 380

Leu Leu Ser His Arg Asp Gly Ala Lys Val His Leu Gly Thr Arg Pro
385                 390                 395                 400

Thr Glu Lys Gln Tyr Glu Thr Leu Glu Asn Gln Leu Ala Phe Leu Cys

```
                    405                 410                 415
Gln Gln Gly Phe Ser Leu Glu Asn Ala Leu Tyr Ala Leu Ser Ala Val
                420                 425                 430

Gly His Phe Thr Leu Gly Cys Val Leu Glu Asp Gln Glu His Gln Val
                435                 440                 445

Ala Lys Glu Glu Arg Glu Thr Pro Thr Thr Asp Ser Met Pro Pro Leu
    450                 455                 460

Leu Arg Gln Ala Ile Glu Leu Phe Asp His Gln Gly Ala Glu Pro Ala
465                 470                 475                 480

Phe Leu Phe Gly Leu Glu Leu Ile Ile Cys Gly Leu Glu Lys Gln Leu
                485                 490                 495

Lys Cys Glu Ser Gly Ser Ala Tyr Ser Arg Ala Arg Thr Lys Asn Asn
                500                 505                 510

Tyr Gly Ser Thr Ile Glu Gly Leu Leu Asp Leu Pro Asp Asp Asp Ala
                515                 520                 525

Pro Glu Glu Ala Gly Leu Ala Ala Pro Arg Leu Ser Phe Leu Pro Ala
    530                 535                 540

Gly His Thr Arg Arg Leu Ser Thr Ala Pro Pro Thr Asp Val Ser Leu
545                 550                 555                 560

Gly Asp Glu Leu His Leu Asp Gly Glu Asp Val Ala Met Ala His Ala
                565                 570                 575

Asp Ala Leu Asp Asp Phe Asp Leu Asp Met Leu Gly Asp Gly Asp Ser
                580                 585                 590

Pro Gly Pro Gly Phe Thr Pro His Asp Ser Ala Pro Tyr Gly Ala Leu
                595                 600                 605

Asp Met Ala Asp Phe Glu Phe Glu Gln Met Phe Thr Asp Ala Leu Gly
    610                 615                 620

Ile Asp Glu Tyr Gly Gly Thr Gly Gly Ser Gly Gly Gly Ser
625                 630                 635                 640

Met Val Ser Lys Gly Glu Glu Leu Phe Thr Gly Val Val Pro Ile Leu
                645                 650                 655

Val Glu Leu Asp Gly Asp Val Asn Gly His Lys Phe Ser Val Arg Gly
                660                 665                 670

Glu Gly Glu Gly Asp Ala Thr Asn Gly Lys Leu Thr Leu Lys Phe Ile
            675                 680                 685

Cys Thr Thr Gly Lys Leu Pro Val Pro Trp Pro Thr Leu Val Thr Thr
            690                 695                 700

Leu Ser His Gly Val Gln Cys Phe Ala Arg Tyr Pro Asp His Met Lys
705                 710                 715                 720

Gln His Asp Phe Phe Lys Ser Ala Met Pro Glu Gly Tyr Val Gln Glu
                725                 730                 735

Arg Thr Ile Phe Phe Lys Asp Asp Gly Thr Tyr Lys Thr Arg Ala Glu
            740                 745                 750

Val Lys Phe Glu Gly Asp Thr Leu Val Asn Arg Ile Glu Leu Lys Gly
            755                 760                 765

Val Asp Phe Lys Glu Asp Gly Asn Ile Leu Gly His Lys Leu Glu Tyr
    770                 775                 780

Asn Phe Asn Ser His Asn Ile Tyr Ile Met Ala Val Lys Gln Lys Asn
785                 790                 795                 800

Gly Ile Lys Val Asn Phe Lys Ile Arg His Asn Val Glu Asp Gly Ser
                805                 810                 815

Val Gln Leu Ala Asp His Tyr Gln Gln Asn Thr Pro Ile Gly Asp Gly
                820                 825                 830
```

```
Pro Val Leu Leu Pro Asp Ser His Tyr Leu Ser Thr Gln Ser Val Leu
            835                 840                 845

Ser Lys Asp Pro Asn Glu Lys Arg Asp His Met Val Leu Leu Glu Phe
    850                 855                 860

Arg Thr Ala Ala Gly Ile Thr Leu Gly Met Asp Glu Leu Tyr Lys
865                 870                 875

<210> SEQ ID NO 27
<211> LENGTH: 1518
<212> TYPE: DNA
<213> ORGANISM: Artificial sequence
<220> FEATURE:
<223> OTHER INFORMATION: Synthetic

<400> SEQUENCE: 27
atgtgccgag ccatctctct taggcgcttg ctgctgctgc tgctgcagct gtcacaactc      60
ctagctgtca ctcaagggat ggtgagcaag ggcgaggagg ataacatggc catcatcaag     120
gagttcatgc gcttcaaggt gcacatggag ggctccgtga acggccacga gttcgagatc     180
gagggcgagg gcgagggccg cccctacgag ggcacccaga ccgccaagct gaaggtgacc     240
aagggtggcc cctgccctt cgcctgggac atcctgtccc ctcagttcat gtacggctcc      300
aaggcctacg tgaagcaccc cgccgacatc cccgactact tgaagctgtc cttccccgag     360
ggcttcaagt gggagcgcgt gatgaacttc gaggacggcg gcgtggtgac cgtgacccag     420
gactcctccc tgcaggacgg cgagttcatc tacaaggtga agctgcgcgg caccaacttc     480
ccctccgacg gccccgtaat gcagaagaag accatgggct gggaggcctc ctccgagcgg     540
atgtaccccg aggacggcgc cctgaagggc gagatcaagc agaggctgaa gctgaaggac     600
ggcggccact acgacgctga ggtcaagacc acctacaagg ccaagaagcc cgtgcagctg     660
cccggcgcct acaacgtcaa catcaagttg gacatcacct cccacaacga ggactacacc     720
atcgtggaac agtacgaacg cgccgagggc cgccactcca ccgcggcat ggacgagctg      780 tacaagaagc ttttttgggc actggtcgtg gttgctggag tcctgttttg ttatggcttg     840
ctagtgacag tggctctttg tgttgagagc ttgtttaagg ggccgcgtga ttacaacccg     900
atatcgagca ccatttgtca tttgacgaat gaatctgatg ggcacacaac atcgttgtat     960
ggtattggat ttggtccctt catcattaca aacaagcact tgtttagaag aaataatgga    1020
acactgttgg tccaatcact acatggtgta ttcaaggtca agaacaccac gactttgcaa    1080
caacacctca ttgatgggag ggacatgata attattcgca tgcctaagga tttcccacca    1140
tttcctcaaa agctgaaatt tagagagcca caagggaag agcgcatatg tcttgtgaca     1200
accaacttcc aaactaagag catgtctagc atggtgtcag acactagttg cacattccct    1260
tcatctgatg gcatattctg gaagcattgg attcaaacca aggatgggca gtgtggcagt    1320
ccattagtat caactagaga tgggttcatt gttggtatac actcagcatc gaatttcacc    1380
aacacaaaca attatttcac aagcgtgccg aaaaacttca tggaattgtt gacaaatcag    1440
gaggcgcagc agtgggttag tggttggcga ttaaatgctg actcagtatt gtgggggggc    1500
cataaagttt tcatgtag                                                  1518

<210> SEQ ID NO 28
<211> LENGTH: 505
<212> TYPE: PRT
<213> ORGANISM: Artificial sequence
<220> FEATURE:
<223> OTHER INFORMATION: Synthetic
```

<400> SEQUENCE: 28

Met Cys Arg Ala Ile Ser Leu Arg Arg Leu Leu Leu Leu Leu Leu Gln
1               5                   10                  15

Leu Ser Gln Leu Leu Ala Val Thr Gln Gly Met Val Ser Lys Gly Glu
            20                  25                  30

Glu Asp Asn Met Ala Ile Ile Lys Glu Phe Met Arg Phe Lys Val His
        35                  40                  45

Met Glu Gly Ser Val Asn Gly His Glu Phe Glu Ile Glu Gly Glu Gly
50                  55                  60

Glu Gly Arg Pro Tyr Glu Gly Thr Gln Thr Ala Lys Leu Lys Val Thr
65                  70                  75                  80

Lys Gly Gly Pro Leu Pro Phe Ala Trp Asp Ile Leu Ser Pro Gln Phe
                85                  90                  95

Met Tyr Gly Ser Lys Ala Tyr Val Lys His Pro Ala Asp Ile Pro Asp
            100                 105                 110

Tyr Leu Lys Leu Ser Phe Pro Glu Gly Phe Lys Trp Glu Arg Val Met
        115                 120                 125

Asn Phe Glu Asp Gly Gly Val Val Thr Val Thr Gln Asp Ser Ser Leu
130                 135                 140

Gln Asp Gly Glu Phe Ile Tyr Lys Val Lys Leu Arg Gly Thr Asn Phe
145                 150                 155                 160

Pro Ser Asp Gly Pro Val Met Gln Lys Lys Thr Met Gly Trp Glu Ala
                165                 170                 175

Ser Ser Glu Arg Met Tyr Pro Glu Asp Gly Ala Leu Lys Gly Glu Ile
            180                 185                 190

Lys Gln Arg Leu Lys Leu Lys Asp Gly Gly His Tyr Asp Ala Glu Val
        195                 200                 205

Lys Thr Thr Tyr Lys Ala Lys Lys Pro Val Gln Leu Pro Gly Ala Tyr
210                 215                 220

Asn Val Asn Ile Lys Leu Asp Ile Thr Ser His Asn Glu Asp Tyr Thr
225                 230                 235                 240

Ile Val Glu Gln Tyr Glu Arg Ala Glu Gly Arg His Ser Thr Gly Gly
                245                 250                 255

Met Asp Glu Leu Tyr Lys Lys Leu Phe Trp Ala Leu Val Val Val Ala
            260                 265                 270

Gly Val Leu Phe Cys Tyr Gly Leu Leu Val Thr Val Ala Leu Cys Val
        275                 280                 285

Glu Ser Leu Phe Lys Gly Pro Arg Asp Tyr Asn Pro Ile Ser Ser Thr
290                 295                 300

Ile Cys His Leu Thr Asn Glu Ser Asp Gly His Thr Thr Ser Leu Tyr
305                 310                 315                 320

Gly Ile Gly Phe Gly Pro Phe Ile Ile Thr Asn Lys His Leu Phe Arg
                325                 330                 335

Arg Asn Asn Gly Thr Leu Leu Val Gln Ser Leu His Gly Val Phe Lys
            340                 345                 350

Val Lys Asn Thr Thr Thr Leu Gln Gln His Leu Ile Asp Gly Arg Asp
        355                 360                 365

Met Ile Ile Ile Arg Met Pro Lys Asp Phe Pro Pro Phe Pro Gln Lys
370                 375                 380

Leu Lys Phe Arg Glu Pro Gln Arg Glu Glu Arg Ile Cys Leu Val Thr
385                 390                 395                 400

Thr Asn Phe Gln Thr Lys Ser Met Ser Ser Met Val Ser Asp Thr Ser

```
            405                 410                 415
Cys Thr Phe Pro Ser Ser Asp Gly Ile Phe Trp Lys His Trp Ile Gln
            420                 425                 430

Thr Lys Asp Gly Gln Cys Gly Ser Pro Leu Val Ser Thr Arg Asp Gly
            435                 440                 445

Phe Ile Val Gly Ile His Ser Ala Ser Asn Phe Thr Asn Thr Asn Asn
450                 455                 460

Tyr Phe Thr Ser Val Pro Lys Asn Phe Met Glu Leu Leu Thr Asn Gln
465                 470                 475                 480

Glu Ala Gln Gln Trp Val Ser Gly Trp Arg Leu Asn Ala Asp Ser Val
                485                 490                 495

Leu Trp Gly Gly His Lys Val Phe Met
            500                 505

<210> SEQ ID NO 29
<211> LENGTH: 2631
<212> TYPE: DNA
<213> ORGANISM: Artificial sequence
<220> FEATURE:
<223> OTHER INFORMATION: Synthetic

<400> SEQUENCE: 29
```

| | | | | | |
|---|---|---|---|---|---|
| atgtgccgag | ccatctctct | taggcgcttg | ctgctgctgc | tgctgcagct | gtcacaactc | 60 |
| ctagctgtca | ctcaagggt | gagcaagggc | gaggaggtca | tcaaagagtt | catgcgcttc | 120 |
| aaggtgcgca | tggagggctc | catgaacggc | cacgagttcg | agatcgaggg | cgagggcgag | 180 |
| ggccgcccct | acgagggcac | ccagaccgcc | aagctgaagg | tgaccaaggg | cggccccctg | 240 |
| cccttcgcct | gggacatcct | gtcccccag | ttcatgtacg | gctccaaggc | gtacgtgaag | 300 |
| caccccgccg | acatccccga | ttacaagaag | ctgtccttcc | ccgagggctt | caagtgggag | 360 |
| cgcgtgatga | acttcgagga | cggcggtctg | gtgaccgtga | cccaggactc | ctccctgcag | 420 |
| gacggcacgc | tgatctacaa | ggtgaagatg | cgcggcacca | acttccccc | cgacggcccc | 480 |
| gtaatgcaga | agaagaccat | gggctgggag | gcctccaccg | agcgcctgta | ccccgcgac | 540 |
| ggcgtgctga | agggcgagat | ccaccaggcc | ctgaagctga | aggacggcgg | ccactacctg | 600 |
| gtggagttca | agaccatcta | catggccaag | aagcccgtgc | aactgcccgg | ctactactac | 660 |
| gtggacacca | agctggacat | cacctcccac | aacgaggact | acaccatcgt | ggaacagtac | 720 |
| gagcgctccg | agggccgcca | ccacctgttc | ctgtacggca | tggacgagct | gtacaagaag | 780 |
| ctttttttggg | cactggtcgt | ggttgctgga | gtcctgtttt | gttatggctt | gctagtgaca | 840 |
| gtggctcttt | gtgttgaaaa | cctgtatttt | cagggtatgt | ctagattaga | taaaagtaaa | 900 |
| gtgattaaca | gcgcattaga | gctgcttaat | gaggtcggaa | tcgaaggttt | aacaacccgt | 960 |
| aaactcgccc | agaagctagg | tgtagagcag | cctacattgt | attggcatgt | aaaaaataag | 1020 |
| cgggctttgc | tcgacgcctt | agccattgag | atgttagata | ggcaccatac | tcacttttgc | 1080 |
| cctttagaag | gggaaagctg | gcaagatttt | ttacgtaata | acgctaaaag | ttttagatgt | 1140 |
| gctttactaa | gtcatcgcga | tggagcaaaa | gtacatttag | gtacacggcc | tacagaaaaa | 1200 |
| cagtatgaaa | ctctcgaaaa | tcaattagcc | tttttatgcc | aacaaggttt | ttcactagag | 1260 |
| aatgcattat | atgcactcag | cgctgtgggg | catttttactt | taggttgcgt | attggaagat | 1320 |
| caagagcatc | aagtcgctaa | agaagaaagg | gaaacaccta | ctactgatag | tatgccgcca | 1380 |
| ttattacgac | aagctatcga | attatttgat | caccaaggtg | cagagccagc | cttcttattc | 1440 |
| ggccttgaat | tgatcatatg | cggattagaa | aaacaactta | aatgtgaaag | tgggtccgcg | 1500 |

```
tacagccgcg cgcgtacgaa aaacaattac gggtctacca tcgagggcct gctcgatctc      1560
ccggacgacg acgcccccga agaggcgggg ctggcggctc cgcgcctgtc ctttctcccc      1620
gcgggacaca cgcgcagact gtcgacggcc ccccgaccg atgtcagcct gggggacgag       1680
ctccacttag acggcgagga cgtggcgatg gcgcatgccg acgcgctaga cgatttcgat      1740
ctggacatgt tggggacgg ggattccccg gtccgggat ttaccccca cgactccgcc         1800 ccctacggcg ctctggatat ggccgacttc gagtttgagc agatgtttac cgatgccctt      1860
ggaattgacg agtacggtgg aggtaccggc ggaggctccg gtggtggctc tatggtgagc     1920
aagggcgagg agctgttcac cggggtggtg cccatcctgg tcgagctgga cggcgacgta     1980
aacggccaca gttcagcgt gaggggcgag ggcgagggcg atgccaccaa cggcaagctg      2040
accctgaagt tcatctgcac caccggcaag ctgcccgtgc cctggcccac cctcgtgacc     2100
accctgagcc acggcgtgca gtgcttcgcc cgctacccg accacatgaa gcagcacgac       2160
ttcttcaagt ccgccatgcc cgaaggctac gtccaggagc gcaccatctt cttcaaggac     2220
gacggcacct acaagacccg cgccgaggtg aagttcgagg gcgacaccct agtgaaccgc     2280
atcgagctga agggcgtcga cttcaaggag gacggcaaca tcctggggca caagctggag     2340
tacaacttca acagccacaa catctatatc atggccgtca agcagaagaa cggcatcaag     2400
gtgaacttca agatccgcca caacgtggag gacggcagcg tgcagctcgc cgaccactac     2460
cagcagaaca cccccatcgg cgacggcccc gtgctgctgc ccgacagcca ctacctgagc     2520
acccagtccg tgctgagcaa agaccccaac gagaagcgcg atcacatggt cctgctggag     2580
ttccgcaccg ccgccgggat cactctcggc atggacgagc tgtacaagta a               2631
```

<210> SEQ ID NO 30
<211> LENGTH: 876
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (292)..(292)
<223> OTHER INFORMATION: Xaa is Gly, Ala, Glu, Leu, Ser, Tyr, or Lys

<400> SEQUENCE: 30

```
Met Cys Arg Ala Ile Ser Leu Arg Arg Leu Leu Leu Leu Leu Gln
1               5                   10                  15

Leu Ser Gln Leu Leu Ala Val Thr Gln Gly Val Ser Lys Gly Glu Glu
                20                  25                  30

Val Ile Lys Glu Phe Met Arg Phe Lys Val Arg Met Glu Gly Ser Met
            35                  40                  45

Asn Gly His Glu Phe Glu Ile Glu Gly Glu Gly Glu Gly Arg Pro Tyr
        50                  55                  60

Glu Gly Thr Gln Thr Ala Lys Leu Lys Val Thr Lys Gly Gly Pro Leu
65                  70                  75                  80

Pro Phe Ala Trp Asp Ile Leu Ser Pro Gln Phe Met Tyr Gly Ser Lys
                85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140
```

```
Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
        165                 170                 175

Tyr Pro Arg Asp Gly Val Leu Lys Gly Glu Ile His Gln Ala Leu Lys
            180                 185                 190

Leu Lys Asp Gly Gly His Tyr Leu Val Glu Phe Lys Thr Ile Tyr Met
        195                 200                 205

Ala Lys Lys Pro Val Gln Leu Pro Gly Tyr Tyr Val Asp Thr Lys
210                 215                 220

Leu Asp Ile Thr Ser His Asn Glu Asp Tyr Thr Ile Val Glu Gln Tyr
225                 230                 235                 240

Glu Arg Ser Glu Gly Arg His His Leu Phe Leu Tyr Gly Met Asp Glu
                245                 250                 255

Leu Tyr Lys Lys Leu Phe Trp Ala Leu Val Val Ala Gly Val Leu
        260                 265                 270

Phe Cys Tyr Gly Leu Leu Val Thr Val Ala Leu Cys Val Glu Asn Leu
        275                 280                 285

Tyr Phe Gln Xaa Met Ser Arg Leu Asp Lys Ser Lys Val Ile Asn Ser
        290                 295                 300

Ala Leu Glu Leu Leu Asn Glu Val Gly Ile Glu Gly Leu Thr Thr Arg
305                 310                 315                 320

Lys Leu Ala Gln Lys Leu Gly Val Glu Gln Pro Thr Leu Tyr Trp His
                325                 330                 335

Val Lys Asn Lys Arg Ala Leu Leu Asp Ala Leu Ala Ile Glu Met Leu
            340                 345                 350

Asp Arg His His Thr His Phe Cys Pro Leu Glu Gly Glu Ser Trp Gln
            355                 360                 365

Asp Phe Leu Arg Asn Asn Ala Lys Ser Phe Arg Cys Ala Leu Leu Ser
        370                 375                 380

His Arg Asp Gly Ala Lys Val His Leu Gly Thr Arg Pro Thr Glu Lys
385                 390                 395                 400

Gln Tyr Glu Thr Leu Glu Asn Gln Leu Ala Phe Leu Cys Gln Gln Gly
                405                 410                 415

Phe Ser Leu Glu Asn Ala Leu Tyr Ala Leu Ser Ala Val Gly His Phe
            420                 425                 430

Thr Leu Gly Cys Val Leu Glu Asp Gln Glu His Gln Val Ala Lys Glu
        435                 440                 445

Glu Arg Glu Thr Pro Thr Thr Asp Ser Met Pro Pro Leu Leu Arg Gln
        450                 455                 460

Ala Ile Glu Leu Phe Asp His Gln Gly Ala Glu Pro Ala Phe Leu Phe
465                 470                 475                 480

Gly Leu Glu Leu Ile Ile Cys Gly Leu Glu Lys Gln Leu Lys Cys Glu
                485                 490                 495

Ser Gly Ser Ala Tyr Ser Arg Ala Arg Thr Lys Asn Asn Tyr Gly Ser
            500                 505                 510

Thr Ile Glu Gly Leu Leu Asp Leu Pro Asp Asp Ala Pro Glu Glu
        515                 520                 525

Ala Gly Leu Ala Ala Pro Arg Leu Ser Phe Leu Pro Ala Gly His Thr
        530                 535                 540

Arg Arg Leu Ser Thr Ala Pro Pro Thr Asp Val Ser Leu Gly Asp Glu
545                 550                 555                 560
```

| Leu | His | Leu | Asp | Gly | Glu | Asp | Val | Ala | Met | Ala | His | Ala | Asp | Ala | Leu |
|---|---|---|---|---|---|---|---|---|---|---|---|---|---|---|---|
| | | | | 565 | | | | 570 | | | | 575 | | | |

| Asp | Asp | Phe | Asp | Leu | Asp | Met | Leu | Gly | Asp | Gly | Asp | Ser | Pro | Gly | Pro |
| | | 580 | | | | | 585 | | | | | 590 | | | |

| Gly | Phe | Thr | Pro | His | Asp | Ser | Ala | Pro | Tyr | Gly | Ala | Leu | Asp | Met | Ala |
| | | | 595 | | | | | 600 | | | | | 605 | | |

| Asp | Phe | Glu | Phe | Glu | Gln | Met | Phe | Thr | Asp | Ala | Leu | Gly | Ile | Asp | Glu |
| | | 610 | | | | | 615 | | | | | 620 | | | |

| Tyr | Gly | Gly | Gly | Thr | Gly | Gly | Ser | Gly | Gly | Ser | Met | Val | Ser |
| 625 | | | | | 630 | | | | 635 | | | | 640 |

| Lys | Gly | Glu | Glu | Leu | Phe | Thr | Gly | Val | Val | Pro | Ile | Leu | Val | Glu | Leu |
| | | | | 645 | | | | 650 | | | | 655 | | | |

| Asp | Gly | Asp | Val | Asn | Gly | His | Lys | Phe | Ser | Val | Arg | Gly | Glu | Gly | Glu |
| | | | 660 | | | | | 665 | | | | | 670 | | |

| Gly | Asp | Ala | Thr | Asn | Gly | Lys | Leu | Thr | Leu | Lys | Phe | Ile | Cys | Thr | Thr |
| | | | 675 | | | | | 680 | | | | | 685 | | |

| Gly | Lys | Leu | Pro | Val | Pro | Trp | Pro | Thr | Leu | Val | Thr | Thr | Leu | Ser | His |
| | | 690 | | | | | 695 | | | | | 700 | | | |

| Gly | Val | Gln | Cys | Phe | Ala | Arg | Tyr | Pro | Asp | His | Met | Lys | Gln | His | Asp |
| 705 | | | | 710 | | | | | 715 | | | | | 720 | |

| Phe | Phe | Lys | Ser | Ala | Met | Pro | Glu | Gly | Tyr | Val | Gln | Glu | Arg | Thr | Ile |
| | | | | 725 | | | | 730 | | | | | 735 | | |

| Phe | Phe | Lys | Asp | Asp | Gly | Thr | Tyr | Lys | Thr | Arg | Ala | Glu | Val | Lys | Phe |
| | | | 740 | | | | | 745 | | | | | 750 | | |

| Glu | Gly | Asp | Thr | Leu | Val | Asn | Arg | Ile | Glu | Leu | Lys | Gly | Val | Asp | Phe |
| | | 755 | | | | | 760 | | | | | 765 | | | |

| Lys | Glu | Asp | Gly | Asn | Ile | Leu | Gly | His | Lys | Leu | Glu | Tyr | Asn | Phe | Asn |
| 770 | | | | 775 | | | | | 780 | | | | | | |

| Ser | His | Asn | Ile | Tyr | Ile | Met | Ala | Val | Lys | Gln | Lys | Asn | Gly | Ile | Lys |
| 785 | | | | 790 | | | | | 795 | | | | | 800 | |

| Val | Asn | Phe | Lys | Ile | Arg | His | Asn | Val | Glu | Asp | Gly | Ser | Val | Gln | Leu |
| | | | 805 | | | | | 810 | | | | | 815 | | |

| Ala | Asp | His | Tyr | Gln | Gln | Asn | Thr | Pro | Ile | Gly | Asp | Gly | Pro | Val | Leu |
| | | | 820 | | | | | 825 | | | | | 830 | | |

| Leu | Pro | Asp | Ser | His | Tyr | Leu | Ser | Thr | Gln | Ser | Val | Leu | Ser | Lys | Asp |
| | | 835 | | | | | 840 | | | | | 845 | | | |

| Pro | Asn | Glu | Lys | Arg | Asp | His | Met | Val | Leu | Leu | Glu | Phe | Arg | Thr | Ala |
| | 850 | | | | | 855 | | | | | 860 | | | | |

| Ala | Gly | Ile | Thr | Leu | Gly | Met | Asp | Glu | Leu | Tyr | Lys |
| 865 | | | | | 870 | | | | | 875 | |

<210> SEQ ID NO 31
<211> LENGTH: 1509
<212> TYPE: DNA
<213> ORGANISM: Artificial sequence
<220> FEATURE:
<223> OTHER INFORMATION: Synthetic

<400> SEQUENCE: 31

| atgtgccgag | ccatctctct | taggcgcttg | ctgctgctgc | tgctgcagct | gtcacaactc | 60 |
| ctagctgtca | ctcaagggt | gagcaagggc | gaggaggtca | tcaaagagtt | catgcgcttc | 120 |
| aaggtgcgca | tggagggctc | catgaacggc | cacgagttcg | agatcgaggg | cgagggcgag | 180 |
| ggccgcccct | acgagggcac | ccagaccgcc | aagctgaagg | tgaccaaggg | cggccccctg | 240 |
| cccttcgcct | gggacatcct | gtcccccag | ttcatgtacg | gctccaaggc | gtacgtgaag | 300 |

```
cacccccgccg acatcccccga ttacaagaag ctgtccttcc ccgagggctt caagtgggag    360
cgcgtgatga acttcgagga cggcggtctg gtgaccgtga cccaggactc ctccctgcag    420
gacggcacgc tgatctacaa ggtgaagatg cgcggcacca acttcccccc cgacggcccc    480
gtaatgcaga agaagaccat gggctgggag gcctccaccg agcgcctgta ccccccgcgac   540
ggcgtgctga agggcgagat ccaccaggcc ctgaagctga aggacggcgg ccactacctg    600
gtggagttca gaccatcta catggccaag aagcccgtgc aactgcccgg ctactactac    660
gtggacacca agctggacat cacctcccac aacgaggact acaccatcgt ggaacagtac    720
gagcgctccg agggccgcca ccacctgttc ctgtacggca tggacgagct gtacaagaag    780
cttttttggg cactggtcgt ggttgctgga gtcctgtttt gttatggctt gctagtgaca    840
gtggctcttt gtgttgagag cttgtttaag gggccgcgtg attacaaccc gatatcgagc    900
accatttgtc atttgacgaa tgaatctgat gggcacacaa catcgttgta tggtattgga    960
tttggtccct tcatcattac aaacaagcac ttgtttagaa gaataatgg aacactgttg    1020
gtccaatcac tacatggtgt attcaaggtc aagaacacca cgactttgca acaacacctc   1080
attgatggga gggacatgat aattattcgc atgcctaagg atttcccacc atttcctcaa   1140
aagctgaaat ttagagagcc acaaagggaa gagcgcatat gtcttgtgac aaccaacttc   1200
caaactaaga gcatgtctag catggtgtca gacactagtt gcacattccc ttcatctgat   1260
ggcatattct ggaagcattg gattcaaacc aaggatgggc agtgtggcag tccattagta   1320
tcaactagag atgggttcat tgttggtata cactcagcat cgaatttcac caacacaaac   1380
aattatttca caagcgtgcc gaaaaacttc atggaattgt tgacaaatca ggaggcgcag   1440
cagtgggtta gtggttggcg attaaatgct gactcagtat tgtgggggg ccataaagtt    1500
ttcatgtag                                                           1509
```

<210> SEQ ID NO 32
<211> LENGTH: 502
<212> TYPE: PRT
<213> ORGANISM: Artificial sequence
<220> FEATURE:
<223> OTHER INFORMATION: Synthetic

<400> SEQUENCE: 32

```
Met Cys Arg Ala Ile Ser Leu Arg Arg Leu Leu Leu Leu Leu Leu Gln
1               5                   10                  15

Leu Ser Gln Leu Leu Ala Val Thr Gln Gly Val Ser Lys Gly Glu Glu
            20                  25                  30

Val Ile Lys Glu Phe Met Arg Phe Lys Val Arg Met Glu Gly Ser Met
        35                  40                  45

Asn Gly His Glu Phe Glu Ile Glu Gly Glu Gly Glu Gly Arg Pro Tyr
    50                  55                  60

Glu Gly Thr Gln Thr Ala Lys Leu Lys Val Thr Lys Gly Gly Pro Leu
65                  70                  75                  80

Pro Phe Ala Trp Asp Ile Leu Ser Pro Gln Phe Met Tyr Gly Ser Lys
                85                  90                  95

Ala Tyr Val Lys His Pro Ala Asp Ile Pro Asp Tyr Lys Lys Leu Ser
            100                 105                 110

Phe Pro Glu Gly Phe Lys Trp Glu Arg Val Met Asn Phe Glu Asp Gly
        115                 120                 125

Gly Leu Val Thr Val Thr Gln Asp Ser Ser Leu Gln Asp Gly Thr Leu
    130                 135                 140
```

Ile Tyr Lys Val Lys Met Arg Gly Thr Asn Phe Pro Pro Asp Gly Pro
145                 150                 155                 160

Val Met Gln Lys Lys Thr Met Gly Trp Glu Ala Ser Thr Glu Arg Leu
            165                 170                 175

Tyr Pro Arg Asp Gly Val Leu Lys Gly Glu Ile His Gln Ala Leu Lys
            180                 185                 190

Leu Lys Asp Gly Gly His Tyr Leu Val Glu Phe Lys Thr Ile Tyr Met
            195                 200                 205

Ala Lys Lys Pro Val Gln Leu Pro Gly Tyr Tyr Val Asp Thr Lys
210                 215                 220

Leu Asp Ile Thr Ser His Asn Glu Asp Tyr Thr Ile Val Glu Gln Tyr
225                 230                 235                 240

Glu Arg Ser Glu Gly Arg His His Leu Phe Leu Tyr Gly Met Asp Glu
            245                 250                 255

Leu Tyr Lys Lys Leu Phe Trp Ala Leu Val Val Ala Gly Val Leu
            260                 265                 270

Phe Cys Tyr Gly Leu Leu Val Thr Val Ala Leu Cys Val Glu Ser Leu
            275                 280                 285

Phe Lys Gly Pro Arg Asp Tyr Asn Pro Ile Ser Ser Thr Ile Cys His
            290                 295                 300

Leu Thr Asn Glu Ser Asp Gly His Thr Thr Ser Leu Tyr Gly Ile Gly
305                 310                 315                 320

Phe Gly Pro Phe Ile Ile Thr Asn Lys His Leu Phe Arg Arg Asn Asn
                325                 330                 335

Gly Thr Leu Leu Val Gln Ser Leu His Gly Val Phe Lys Val Lys Asn
                340                 345                 350

Thr Thr Thr Leu Gln Gln His Leu Ile Asp Gly Arg Asp Met Ile Ile
                355                 360                 365

Ile Arg Met Pro Lys Asp Phe Pro Pro Phe Pro Gln Lys Leu Lys Phe
370                 375                 380

Arg Glu Pro Gln Arg Glu Glu Arg Ile Cys Leu Val Thr Thr Asn Phe
385                 390                 395                 400

Gln Thr Lys Ser Met Ser Ser Met Val Ser Asp Thr Ser Cys Thr Phe
                405                 410                 415

Pro Ser Ser Asp Gly Ile Phe Trp Lys His Trp Ile Gln Thr Lys Asp
            420                 425                 430

Gly Gln Cys Gly Ser Pro Leu Val Ser Thr Arg Asp Gly Phe Ile Val
            435                 440                 445

Gly Ile His Ser Ala Ser Asn Phe Thr Asn Thr Asn Asn Tyr Phe Thr
            450                 455                 460

Ser Val Pro Lys Asn Phe Met Glu Leu Leu Thr Asn Gln Glu Ala Gln
465                 470                 475                 480

Gln Trp Val Ser Gly Trp Arg Leu Asn Ala Asp Ser Val Leu Trp Gly
            485                 490                 495

Gly His Lys Val Phe Met
            500

<210> SEQ ID NO 33
<211> LENGTH: 7
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE -continued

```
<222> LOCATION: (7)..(7)
<223> OTHER INFORMATION: Xaa is Gly, Ala, Glu, Leu, Ser, Tyr, or Lys

<400> SEQUENCE: 33

Glu Asn Leu Tyr Phe Gln Xaa
1               5
```

MODULAR SENSOR ARCHITECTURE FOR CELL BASED BIOSENSORS

The present application claims priority to U.S. Provisional Application Ser. No. 61/515,704, filed Aug. 5, 2011, which is herein incorporated by reference in its entirety.

This invention was made with government support under grant number W911NF-11-2-066 awarded by the Army Research Office (DARPA). The government has certain rights in the invention.

FIELD OF THE INVENTION

The present invention provides modular extracellular sensors, nucleic acids encoding such sensors, cells expressing such sensors, and methods of employing such sensors and cells for detecting extracellular ligands. In certain embodiments, the extracellular sensors comprise a ligand binding domain, a transmembrane domain, a protease domain, a protease cleavage site, and a functional domain (e.g., transcription factor). In other embodiments, a pair of extracellular receptors is provided where both receptors contain a ligand binding domain and transmembrane domain, and one receptor contains a protease cleavage site and a functional domain (e.g., transcription factor) and the other receptor contains a protease domain.

BACKGROUND

In general, reporter constructs rely upon natural mechanisms for sensing an extracellular ligand via a reporter, inducing an intracellular signaling cascade (such as a relay of kinases), and eventually causing a transcription factor to be active and present in the cell nucleus. The reporter construct may incorporate a natural promoter (which may be regulated by multiple transcription factors) or an engineered promoter (which may be regulated by one specific transcription factor) to drive the conditional expression of a reporter gene. While this approach is useful for monitoring native signaling, it is not well-suited to robust biosensor engineering for several reasons. Because native receptors and signaling proteins are required, these components must either be already present in the cell type of interest or they must be exogenously expressed (e.g., by transfection of expression plasmids) at levels that guarantee adequate ligand-inducible signaling without risking ligand-independent constitutive signaling. In addition, native mechanisms often exist for promoting or suppressing the activity of receptors, intracellular signaling proteins, and promoters. Consequently, it is often not efficient (or even possible) to transfer reporter systems between cell types, and potential interference by native regulatory mechanisms complicates the interpretation of reporter gene outputs.

The TANGO assay system is marketed by Life Technologies and was originally described by Barnea et al. (Proc Natl Acad Sci USA. 2008 Jan. 8; 105(1):64-9). The TANGO system is designed to detect the interaction of two native proteins: one protein is fused (genetically) to the Tev protease and the second protein is fused (genetically) to a Tev PCS-transcription factor domain. In TANGO, when the two engineered proteins are held in proximity, which is mediated by a native protein-protein interaction, Tev cleaves the PCS to release the transcription factor. Although the TANGO approach can be used to monitor signaling through a native receptor, this strategy still relies upon native mechanisms and interactions (such as ligand binding-dependent recruitment of an intracellular signaling protein to a receptor complex), which are subject to interference from native regulatory mechanisms. Moreover, designing a new TANGO biosensor requires identifying both a suitable native receptor and a corresponding intracellular signaling protein or proteins.

SUMMARY OF THE INVENTION

The present invention provides modular extracellular sensors, nucleic acids encoding such sensors, cells expressing such sensors, and methods of employing such sensors and cells for detecting extracellular ligands. In certain embodiments, the extracellular sensors comprise a ligand binding domain, a transmembrane domain, a protease domain, a protease cleavage site, and a functional domain (e.g., transcription factor). In other embodiments, a pair of extracellular receptors is provided where both receptors contain a ligand binding domain and transmembrane domain, and one receptor contains a protease cleavage site and a functional domain (e.g., transcription factor) and the other receptor contains a protease domain.

In certain embodiments, the modular extracellular sensor architecture (MESA) of the present invention is fully orthogonal, such that it can easily be adapted to any cell type. Moreover, generation of a novel MESA biosensor is much more efficient in that it requires only the incorporation of a suitable ligand-binding domain (LB), rather than coopting an entire native receptor, intracellular signaling protein, and a corresponding promoter system. A related and important consequence is that novel MESA biosensors provided herein may be engineered to detect ligands for which no natural receptor exists, since all that is required is that LB domains be identified (e.g., using approaches such as phage-displayed peptides or antibody fragments) and incorporated into a MESA receptor.

In certain embodiments, the MESA biosensors of the present invention, unlike the TANGO system, fully decouple a biosensor system from the endogenous signaling machinery of the cell, thereby eliminating cross-talk and ensuring that activation is only induced by binding of the target ligand. The MESA receptors of the present invention may be engineered to detect ligands for which no natural receptor exists (e.g., by incorporating ligand-binding domains identified from random libraries), which is not possible using the TANGO approach. Unlike TANGO systems, MESA receptors are highly "engineerable", such that biophysical properties may be modulated in a straightforward fashion to optimize biosensor performance characteristics.

In some embodiments, the present invention provides compositions comprising: i) an exogenous extracellular sensor (e.g., in a cell), and/or ii) a nucleic acid sequence encoding the exogenous extracellular sensor, wherein the exogenous extracellular sensor comprises: a) a ligand binding domain, b) a transmembrane domain, c) a protease cleavage site, and d) a functional domain (e.g., transcription factor). In certain embodiments, the transmembrane domain and protease domains are directly linked together with no intervening amino acids (e.g., there is no intracellular spacer or other sequences). In particular embodiments, there is an intracellular spacer between the transmembrane domain and protease domain which is 1, 2, 3, 4, 5, or 6 amino acids in length.

In certain embodiments, the exogenous extracellular sensor further comprises a protease domain. In other embodiments, the exogenous extracellular sensor further comprises an extracellular spacer. In additional embodiments, the exogenous extracellular sensor further comprises an intracellular spacer. In further embodiments, the compositions further comprise a genetic construct, wherein the genetic construct is configured to express a gene in response to the transcription factor. In additional embodiments, the gene is a reporter gene or a therapeutic gene (or any other gene). In particular embodiments, the compositions comprise the cell. In other embodiments, the compositions comprise the nucleic acid sequence (e.g., plasmid or other vector).

In some embodiments, the compositions further comprise an additional exogenous extracellular sensor, wherein the additional exogenous extracellular sensor comprises: a different ligand binding domain, a transmembrane domain, a protease cleavage site, and a different functional domain (e.g., different transcription factor). In further embodiments, the compositions further comprise a genetic construct, wherein the genetic construct is configured to express a reporter or therapeutic gene in response to the functional domain (e.g., transcription factor) and the different functional domain (e.g., different transcription factor). In other embodiments, the compositions further comprise a third (or fourth or fifth) exogenous extracellular sensor, wherein third additional exogenous extracellular sensor comprises: a third ligand binding domain, a transmembrane domain, a protease cleavage site, and a third functional domain (e.g., transcription factor).

In particular embodiments, the present invention provides compositions comprising: i) first and second exogenous extracellular sensors (e.g., in a cell), and/or ii) one or more nucleic acid sequences encoding the first and second exogenous extracellular sensors, wherein the first exogenous extracellular sensor comprises: a) a ligand binding domain, b) a transmembrane domain, c) a protease cleavage site, and d) a functional domain (e.g., transcription factor); and wherein the second exogenous extracellular sensor comprises: e) a ligand binding domain, f) a transmembrane domain, and g) a protease domain. In certain embodiments, the compositions further comprise third and fourth (or fifth, sixth, etc.) exogenous extracellular sensors.

In some embodiments, the present invention provides methods of detecting a ligand in a sample comprising: a) contacting the cell described herein (e.g., as described above) with a sample or a subject suspected of containing a ligand bound by the exogenous extracellular domain, wherein the cell contains a reporter construct, wherein the reporter construct is configured to express a reporter gene in response to the transcription factor; and b) detecting the presence or absence of expression of the reporter gene as indicating of the presence or absence of the ligand in the sample or subject.

In certain embodiments, the ligand is a natural or non-natural analyte for which no natural receptor exists. In other embodiments, the reporter gene allows for in vivo imaging of the subject.

In some embodiments, the present invention provides methods of treating a subject comprising: contacting the cell described herein (e.g., described above) with a subject suspected of containing a ligand bound by the exogenous extracellular domain, wherein the cell contains a therapeutic construct, wherein the therapeutic construct is configured to express a therapeutic gene in response to the functional domain (e.g., transcription factor).

In some embodiments, the present invention provides methods of detecting a ligand in a sample or subject comprising: a) contacting a sample or a subject with a cell comprising a first and/or second extracellular receptor, wherein said first extracellular sensor comprises: a) a first ligand binding domain, b) a first transmembrane domain, c) a protease cleavage site, and d) a functional domain; wherein said second exogenous extracellular sensor comprises: e) a second ligand binding domain, f) a second transmembrane domain, and g) a protease domain, and wherein said sample or said subject are suspected of containing a ligand bound by said first and/or second extracellular sensors, wherein said cell contains a reporter construct, wherein said reporter construct is configured to produce a detectable signal in response to said functional domain; and b) detecting the presence or absence of said detectable signal as indicating the presence or absence of said ligand in said sample or subject.

In certain embodiments, the present invention provides methods of treating a subject comprising: contacting a subject with: a) a composition comprising: i) first and second extracellular sensors, and/or ii) a nucleic acid sequence encoding said first and second extracellular receptors, wherein said first extracellular sensor comprises: A) a first ligand binding domain, B) a first transmembrane domain, C) a protease cleavage site, and D) a functional domain; and wherein said second extracellular sensor comprises: E) a second ligand binding domain, F) a second transmembrane domain, and G) a protease domain; and wherein said subject is suspected of containing a ligand bound by said first and/or second exogenous extracellular sensors; and b) a therapeutic construct configured to express a therapeutic gene in response to said functional domain.

DESCRIPTION OF THE FIGURES

FIG. 4A shows predicted kinetic constants for cleavage of PCS sequences in which the final or P1' amino acid (i.e., X in ENLYFQX (SEQ ID NO:33)) is selected as indicated (5). FIGS. 4B and 4C show results from experiments where human HEK293FT cells were transfected with a tTA-responsive reporter plasmid and either plasmids encoding both target chain (TC) and protease chain (PC) receptors containing extracellular domains comprised of mCherry (M), dTomato (T) or CD4 ectodomain (C), or with a plasmid encoding free tTA as a control (where indicated). Transfected cells were incubated for 24 hours, and then expression of the tTA-induced reporter gene (GFP) was quantified by flow cytometry. An additional plasmid encoding DsRedExpress2 was included in all samples, such that only successfully transfected cells were analyzed for GFP expression, and GFP expression was normalized as a percentage of the free tTA positive control. In each case, the TC and PC contain an intracellular spacer (ISP) of 6 amino acids (2 flexible amino acids plus an additional 4 charged residues adjacent to the membrane, termed ISP:2) (B) or 0 amino acids (termed ISP:0) (C). Amino acid in P1' position of PCS on TC is indicated by "PCS". Data are presented as mean+/- standard deviation for experimental triplicates.

FIG. 5A shows schematics of the dTomato and mCherry autoinhibitory TEV-based protease chain (PC) variants which include the C-terminal portions of the native TEV protease that are autocleaved and occupy the catalytic site post-cleavage. FIG. 5B shows target chain (TC) variants of dTomato and mCherry that include a tTA-BFP fusion enable quantifying TC expression level for different receptor designs.

FIG. 7A shows a schematic view of the mCherry_PCS-0X-tTa MESA receptor construct, composed of the mCherry extracellular domain, a transmembrane domain (TM), protease cleavage site (PCS), and a tetracycline-responsive transactivator (tTA) transcription factor. FIG. 7B shows the nucleotide sequence (SEQ ID NO:1) of this construct, and FIG. 7C shows the amino acid sequence (SEQ ID NO:2) of this construct, which shows the PCS underlined (with a terminal amino acid "X" that is either Gly, Ala, Glu, Leu, Ser, Tyr, or Lys).

FIG. 8A shows a schematic view of the mCherry_PCS-2X-tTa MESA receptor construct, composed of the mCherry extracellular domain, a transmembrane domain (TM), protease cleavage site (PCS), a six amino acid spacer (2X), and a tetracycline-responsive transactivator (tTA) transcription factor. FIG. 8B shows the nucleotide sequence (SEQ ID NO:3) of this construct, and FIG. 8C shows the amino acid sequence (SEQ ID NO:4) of this construct, which shows the PCS highlighted and underlined (with a terminal amino acid "X" that is either Gly, Ala, Glu, Leu, Ser, Tyr, or Lys) and shows a six amino acid spacer underlined and highlighted.

FIG. 9A shows a schematic view of the mCherry_ISP_0_TEV MESA receptor construct, composed of an mCherry extracellular domain, a transmembrane domain (TM), no intracellular spacer (ISP-0) (i.e., zero amino acids in length), and a protease domain (TEV) which is a tobacco Etch virus protease. FIG. 9B shows the nucleotide sequence (SEQ ID NO:5) of this construct, and FIG. 9C shows the amino acid sequence (SEQ ID NO:6) of this construct.

FIG. 10A shows a schematic view of the mCherry_ISP-2_TEV MESA receptor construct, composed of an mCherry extracellular domain, a transmembrane domain (TM), a six amino acid intracellular spacer (ISP-2), and a protease domain (TEV) which is a tobacco Etch virus protease. FIG. 10B shows the nucleotide sequence (SEQ ID NO:7) of this construct, and FIG. 10C shows the amino acid sequence (SEQ ID NO:8) of this construct.

FIG. 11A shows a schematic view of the dTomato_PCS-0X-tTa MESA receptor construct, composed of the dTomato extracellular domain, a transmembrane domain (TM), protease cleavage site (PCS), and a tetracycline-responsive transactivator (tTA) transcription factor. No intracellular spacer is included in this construct. FIG. 11B shows the nucleotide sequence (SEQ ID NO:9) of this construct, and FIG. 11C shows the amino acid sequence (SEQ ID NO:10) of this construct, which shows the PCS underlined (with a terminal amino acid "X" that is either Gly, Ala, Glu, Leu, Ser, Tyr, or Lys).

FIG. 12A shows a schematic view of the dTomato_PCS-2X-tTa MESA receptor construct, composed of the dTomato extracellular domain, a transmembrane domain (TM), protease cleavage site (PCS), a six amino acid spacer (2X), and a tetracycline-responsive transactivator (tTA) transcription factor. FIG. 12B shows the nucleotide sequence (SEQ ID NO:11) of this construct, and FIG. 12C shows the amino acid sequence (SEQ ID NO:12) of this construct, which shows the PCS highlighted and underlined (with a terminal amino acid "X" that is either Gly, Ala, Glu, Leu, Ser, Tyr, or Lys) and shows a six amino acid spacer underlined and highlighted.

FIG. 13A shows a schematic view of the dTomato_ISP_0_TEV MESA receptor construct, composed of a dTomato extracellular domain, a transmembrane domain (TM), no intracellular spacer (ISP-0) (i.e., zero amino acids in length), and a protease domain (TEV) which is a tobacco Etch virus protease. FIG. 13B shows the nucleotide sequence (SEQ ID NO:13) of this construct, and FIG. 13C shows the amino acid sequence (SEQ ID NO:14) of this construct.

FIG. 14A shows a schematic view of the dTomato_ISP-2_TEV MESA receptor construct, composed of a dTomato extracellular domain, a transmembrane domain (TM), a six amino acid intracellular spacer (ISP-2), and a protease domain (TEV) which is a tobacco Etch virus protease. FIG. 14B shows the nucleotide sequence (SEQ ID NO:15) of this construct, and FIG. 14C shows the amino acid sequence (SEQ ID NO:16) of this construct.

FIG. 15A shows a schematic view of the CD4_PCS-0X-tTa MESA receptor construct, composed of the CD4 construct extracellular domain, a transmembrane domain (TM), protease cleavage site (PCS), and a tetracycline-responsive transactivator (tTA) transcription factor. No intracellular spacer is included in this construct. FIG. 15B shows the nucleotide sequence (SEQ ID NO:17) of this construct, and FIG. 15C shows the amino acid sequence (SEQ ID NO:18) of this construct, which shows the PCS underlined (with a terminal amino acid "X" that is either Gly, Ala, Glu, Leu, Ser, Tyr, or Lys).

FIG. 16A shows a schematic view of the CD4_PCS-2X-tTa MESA receptor construct, composed of the CD4 construct extracellular domain, a transmembrane domain (TM), protease cleavage site (PCS), a six amino acid spacer (2X), and a tetracycline-responsive transactivator (tTA) transcription factor. FIG. 16B shows the nucleotide sequence (SEQ ID NO:19) of this construct, and FIG. 16C shows the amino acid sequence (SEQ ID NO:20) of this construct, which shows the PCS highlighted and underlined (with a terminal amino acid "X" that is either Gly, Ala, Glu, Leu, Ser, Tyr, or Lys) and shows a six amino acid spacer underlined and highlighted.

FIG. 17A shows a schematic view of the CD4_ISP-0_TEV MESA receptor construct, composed of a CD4 construct extracellular domain, a transmembrane domain (TM), no intracellular spacer (ISP-0) (i.e., zero amino acids in length), and a protease domain (TEV) which is a tobacco Etch virus protease. FIG. 17B shows the nucleotide sequence (SEQ ID NO:21) of this construct, and FIG. 17C shows the amino acid sequence (SEQ ID NO:22) of this construct.

FIG. 18A shows a schematic view of the CD4_ISP-2_TEV MESA receptor construct, composed of a CD4 construct extracellular domain, a transmembrane domain (TM), a six amino acid intracellular spacer (ISP-2), and a protease domain (TEV) which is a tobacco Etch virus protease. FIG. 18B shows the nucleotide sequence (SEQ ID NO:23) of this construct, and FIG. 18C shows the amino acid sequence (SEQ ID NO:24) of this construct.

FIG. 19A shows a schematic view of the mCherry_PCS-0X-tTa-BFP MESA receptor construct, composed of the mCherry extracellular domain, a transmembrane domain (TM), protease cleavage site (PCS), and a tetracycline-responsive transactivator (tTA) transcription factor linked to BFP (blue fluorescent protein). No intracellular spacer is included in this construct. FIG. 19B shows the nucleotide sequence (SEQ ID NO:25) of this construct, and FIG. 19C shows the amino acid sequence (SEQ ID NO:26) of this construct, which shows the PCS underlined (with a terminal amino acid "X" that is either Gly, Ala, Glu, Leu, Ser, Tyr, or Lys).

FIG. 20A shows a schematic view of the mCherry_ISP-0_TEV-AI MESA receptor construct, composed of a mCherry extracellular domain, a transmembrane domain (TM), no intracellular spacer (ISP-0) (i.e., zero amino acids in length), and a protease domain (TEV) which is a tobacco Etch virus protease which is linked to the natural auto-inhibitory (AI) tail. FIG. 20B shows the nucleotide sequence (SEQ ID NO:27) of this construct, and FIG. 20C shows the amino acid sequence (SEQ ID NO:28) of this construct.

FIG. 21A shows a schematic view of the dTomato_PCS-0X-tTa-BFP MESA receptor construct, composed of the dTomato extracellular domain, a transmembrane domain (TM), protease cleavage site (PCS), and a tetracycline-responsive transactivator (tTA) transcription factor linked to BFP (blue fluorescent protein). No intracellular spacer is included in this construct. FIG. 21B shows the nucleotide sequence (SEQ ID NO:29) of this construct, and FIG. 21C shows the amino acid sequence (SEQ ID NO:30) of this construct, which shows the PCS underlined (with a terminal amino acid "X" that is either Gly, Ala, Glu, Leu, Ser, Tyr, or Lys).

FIG. 22A shows a schematic view of the dTomato_ISP-0_TEV-AI MESA receptor construct, composed of a dTomato extracellular domain, a transmembrane domain (TM), no intracellular spacer (ISP-0) (i.e., zero amino acids in length), and a protease domain (TEV) which is a tobacco Etch virus protease which is linked to the natural auto-inhibitory (AI) tail. FIG. 22B shows the nucleotide sequence (SEQ ID NO:31) of this construct, and FIG. 22C shows the amino acid sequence (SEQ ID NO:32) of this construct.

DETAILED DESCRIPTION

The present invention provides modular extracellular sensors, nucleic acids encoding such sensors, cells expressing such sensors, and methods of employing such sensors and cells for detecting extracellular ligands. In certain embodiments, the extracellular sensors comprise a ligand binding domain, a transmembrane domain, a protease domain, a protease cleavage site, and a functional domain (e.g., transcription factor). In other embodiments, a pair of extracellular receptors is provided where both receptors contain a ligand binding domain and transmembrane domain, and one receptor contains a protease cleavage site and a functional domain (e.g., transcription factor) and the other receptor contains a protease domain.

The present invention provides a general technology for building living cell-based biosensors. In certain embodiments, the MESA system comprises engineered receptor proteins that can detect extracellular ligands (e.g., such as cytokines or other large macromolecules) and transduce this information across the cell membrane to release an engineered transcription factor that drives the expression of an engineered gene. This sensing modality is novel in that it does not require the utilization of any native protein-protein interactions for signal transduction (i.e., it can be fully "orthogonal"), and thus it is not susceptible to native regulatory mechanisms. Therefore, in certain embodiments, MESA is the first system to enable fully orthogonal sensing of extracellular cues, a capability generally required for engineering robust cell-based biosensors.

Such biosensors have a wide variety of uses including in vitro laboratory assays (e.g., to detect/quantify specific analytes), as powerful new experimental tools for studying in vivo animal models (e.g., wherein engineered cell-based biosensors could be adoptively transferred, generated from transplanted bone marrow, or genetically engineered in a transgenic animal), and as human therapeutics (e.g., for augmenting the functionality of engineered cell-based therapies). This invention could also be adapted to function in other cell types, such as insect cells or microbes (e.g., yeast) to create cell-based biosensors for a variety of applications.

Figure 1:
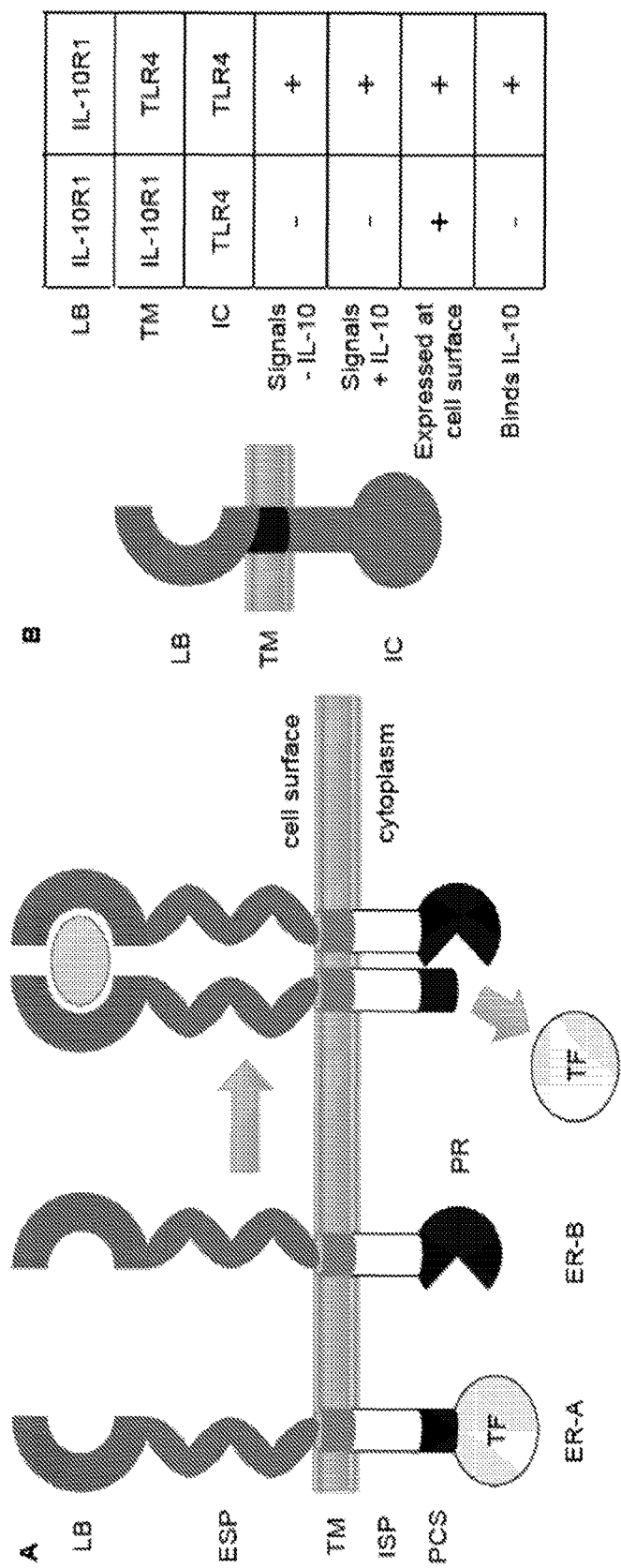
FIG. 1a shows an exemplary Implementation of the Modular Extracellular Sensor Architecture (MESA) for a heterodimerization/multimerization-based signaling mechanism. Engineered receptor alpha (ER-A) and beta (ER-B) chains comprise ligand-binding (LB), extracellular spacer (ESP), transmembrane (TM), intracellular spacer (ISP), protease cleavage site (PCS), transcription factor (TF) and protease (PR) domains. In this exemplary scheme, ligand binding-induced dimerization (or multimerization) allows the protease to cleave its cognate cleavage site, releasing the engineered transcription factor to traffic to the nucleus and regulate gene expression from an engineered promoter.
FIG. 1b shows Preliminary findings for receptor engineering. Results are summarized for two representative chimeras composed of LB, TM, and intracellular (IC) domains of either IL-10R1 or TLR4 (murine). Signaling +/− recombinant IL-10 was assessed using HEK 293 cells engineered to express GFP under the control of NF-KB, which is activated downstream of TLR4 IC domain dimerization. Cell surface expression was assessed by flow cytometry using antibodies against IL-10R1 LB domain. Since IL-10 competes with this antibody for binding to IL-10R1, a competition assay was performed to evaluate IL-10 binding to cell surface receptors. This binding assay was repeated at both 4 degrees C. and 25 degrees C. to assess whether ligand binding requires receptor diffusion in the membrane; results were comparable, suggesting that the constitutively active receptor oligomerizes in the absence of ligand.

In certain embodiments where two receptors are employed, the general mode of action of the MESA platform is that ligand binding induces the aggregation of two or more MESA receptors, bringing an intracellular protease domain (PR) into proximity with a cognate intracellular protease cleavage site (PCS), and upon cleavage of the PCS by PR, a transcription factor (TF) or other functional domain is released from the MESA receptor at the cell membrane to carry out its function (e.g., a TF may localize to the nucleus to induce gene expression). One implementation of this architecture would be a heterodimerization- (or heteromultimerization-) based signaling mechanism, which is summarized in FIG. 1. In this system, one engineered receptor chain contains the PR and the other engineered receptor chain contains the PCS-TF domain. Other implementations include, for example, a homodimerization- (or homomultimerization-) based mechanism in which each MESA chain contains both PR and PCS-TF domains, but the receptor is engineered such that cleavage may occur in trans, but not in cis (i.e., one chain may not release its own TF).

A general implementation of one embodiment of the MESA system is as follows: receptors are designed, DNA sequences encoding these receptors are generated (by molecular biology and/or DNA synthesis) and inserted into a suitable expression vector (such as a plasmid or a viral gene delivery system), the expression vector is transfected or transduced into a suitable cell line or stock of primary cells (together with a suitable reporter construct, which expresses a reporter gene in response to nuclear-localized TF), ligand is added to the cell culture medium, and induced reporter gene expression is quantified by suitable means.

In certain embodiments, the present invention provides: i) a cell-based biosensor for detecting a natural analyte of interest in vitro; ii) a cell-based biosensor for detecting a natural analyte of interest in vivo; iii) a cell-based biosensor for in vitro detection of a natural analyte for which no natural receptor exists; iv) a cell-based biosensor for in vivo detection of a natural analyte for which no natural receptor exists; v) a cell-based biosensor for in vitro detection of an engineered analyte for which no natural receptor exists.

In some embodiments, the present invention provides: i) an approach where a pair of MESA receptors are engineered with ligand-binding domains that recognize a specific peptide, and then a polypeptide ligand is engineered to include two or more copies of the target peptide; ii) a cell-based biosensor for detecting a specific pattern of multiple analytes of interest (e.g., by coupling MESA receptors to engineered gene circuits to enable signal processing) in vitro; iii) a cell-based biosensor for detecting a specific pattern of multiple analytes of interest (e.g., by coupling MESA receptors to engineered gene circuits to enable signal processing) in vivo; iv) a cell-based biosensor coupled to expression of a gene that enables in vivo imaging (e.g., by MRI) for diagnostic purposes; v) a cell-based biosensor coupled to expression of a therapeutic agent to create targeted cellular therapies, which may be used to treat cancer, autoimmune disease, and other diseases; vi) a multicellular network using synthetic intercellular communication (e.g., engineering some cells to express MESA receptors and others to secrete MESA ligands), with applications including: scientific investigation of biological processes including development, immune function, wound healing, etc., cell & tissue-based products for applications including tissue engineering, regenerative medicine, immune therapy, transplantation medicine, cellular therapies, etc.

In additional embodiments, the present invention provides: i) synthetic multicellular networks for engineering customized multicellular organisms; ii) cell-based biosensor for in vivo detection of an engineered analyte for which no natural receptor exists. One example of this approach would be to pair MESA receptors engineered with ligand-binding domains that recognize a specific peptide, and then engineer a polypeptide ligand that includes two or more copies of the target peptide.

In some embodiments, the present invention provides all-in-one receptors. For example, in such embodiments of the MESA platform, the protease, protease target sequence, and released functional domain (e.g., a transcription factor) are encoded on a single polypeptide chain. For example, such a chain may be engineered such that the protease does not cleave its target in cis, but upon the binding of two or more MESA chains to the target ligand, the protease on one chain cleaves the protease target sequence on another MESA chain (in trans) within the receptor-ligand complex, thus releasing the transcription factor.

All MESA receptors can be modified in order to optimize specific receptor properties. Modifications include, for example, the following (and abbreviations refer to protein domains described in FIG. 1 of the disclosure): i) varying the length of ISP (on either MESA chain) to include, for example, between 0-20, 0-50, or 0-150 (e.g., 0 . . . 5 . . . 50 . . . 100 . . . 130 . . . or 150) non-structured amino-acid residues (e.g., glycines or alternating glycine-serine residues); ii) varying the predicted mechanical properties of ISP (on either MESA chain) by replacing non-structured amino acids with structured subdomains (e.g., an alpha-helical domain); iii) including an ESP domain (either structured or unstructured, of lengths between 0-20 or 0-50 or 0-150 amino acids). Structured domains may include, for example, an immunoglobulin motif, (e.g., for presentation of LB domains that are derived from antibody fragments at a certain distance away from the cell surface); altering the sequence of the PCS to enhance or inhibit the rate of PR-mediated cleavage; or varying the combinations of ER-A and ER-B chains uses to constitute a complete MESA receptor system.

MESA variants may use, for example, ligand-binding domain interactions including: i) using an antibody (or a fragment thereof) to bind to the target ligand; ii) implementation in a homodimeric MESA receptor (both antibody fragments are identical and bind to identical sites on a polyvalent ligand, such as a homodimeric cytokine); iii) implementation in a heterodimeric MESA receptor (e.g., each MESA chain incorporates a distinct antibody fragment, such that a monovalent ligand can still induce MESA receptor dimerization or multimerization); iv) incorporating a modular protein-peptide interaction that is not from a receptor ligand system (e.g., conserved protein motifs such as SH3, PDZ, and GBD domains bind distinct and unique consensus peptide motifs) to create an engineered MESA receptor-ligand system.

In certain embodiments, the released transcription factor on ER-A is replaced with another functional domain, such as a catalytic domain (whose activity requires cleavage-mediated release), a separate protease domain (whose activity requires cleavage-mediated release), a DNA-binding domain (e.g., zinc-finger or TAL Effector-based domains) coupled to a functional domain (e.g., an endonuclease, a chromatin modifying enzyme such as the Krueppel-associated box or KRAB protein, or other enzymes or cofactor-recruiting domains). In particular embodiments, modification of the MESA system to detect intracellular analytes, such that intracellular versions of the MESA receptors may be: ER-A could contain LB-ISP-PCS-TF domains and ER-B could contain LB-ISP-PR domains. Ligand-binding by the two chains would again enable protease-mediated cleavage and release of a functional domain (such as transcription factor, TF).

Exemplary applications of MESA-based biosensors may be constructed in multiple cellular contexts for applications in basic science, biotechnology, and medicine (including both diagnostics and therapeutics). MESA biosensors (e.g., implemented in mammalian cells) would have a wide variety of potential uses including in vitro laboratory assays (e.g., to detect/quantify specific analytes), as powerful new experimental tools for studying in vivo animal models (e.g., engineered cell-based biosensors could be adoptively transferred, generated from transplanted bone marrow, or genetically engineered in a transgenic animal to monitor extracellular species in real time in living animals), and potentially as human therapeutics (e.g., for engineering cell-based therapies that probe their environment and deliver a therapeutic payload only at desirable locations). This powerful synthetic biology technology may also be adapted to function in other cell types, such as insect cells or microbes (e.g., yeast) to create cell-based biosensors for applications in biotechnology.

Embodiments of the Modular Extracellular Sensor Architecture (MESA) are based upon a mechanism summarized in FIG. 1A. Exemplary details are as follows. Each engineered receptor (ER) is composed of two chains, each of which is a type I transmembrane protein. The alpha chain (ER-A) may be fused at its C-terminus to an engineered transcription factor (TF), bridged by a peptide harboring a TEV protease cleavage site (PCS). The beta chain (ER-B) may be fused at its C-terminus to the TEV protease (PR). Other domains include ligand-binding domains (LB), extracellular spacers (ESP), intracellular spacers (ISP) (e.g., which may be absent or a short length), and transmembrane domains (TM). In such embodiments the binding of ER-A and ER-B to a ligand may lead to receptor oligomerization and PR-mediated cleavage and release of TF. This strategy is suitable for recognition of any ligand possessing more than one domain that may be recognized by a LB domain, as described in detail below. Modular receptor construction is intrinsic to the MESA strategy, since receptor design may, in certain embodiments, require adjustment for each receptor-ligand combination. Domain junctions may be engineered by introducing unique restriction sites to facilitate exchange(42).

In certain embodiments, the platform uses a TM domain from CD28, which is amenable to monomeric cell surface expression of engineered receptors. Optional ESP may include immunoglobulin-like hinge domains from IgG1 and CD8, which confer varying degrees of conformation flexibility and are often used in engineered T cell receptors, as well as non-structured, polar, glycine-rich linkers of various lengths. Excessive conformational flexibility in the ESP may increase the entropic penalty for receptor dimerization, thereby reducing the effective affinity of the receptor for its ligand. LB domains may be unique for each ligand. Intracellular signaling may be largely conserved between engineered receptors. For example, one can test ISP using flexible glycine-rich linkers of varying lengths or more structured linear peptides, which can be incorporated as repeat units to confer discrete amounts of spacing.

To evaluate intracellular signaling architectures, one can perform experiments that utilize engineered receptors in which the target and protease chains both include the extracellular domain from dTomato, which promotes the formation of constitutive dimers (such that no ligand is required for activation). Functional intracellular signaling architectures can be carried forward to identify ligand binding-inducible receptors. To evaluate receptor signaling, tTA may be selected as the test TF, and human HEK 293 cells may be engineered to express GFP under the control of a tTA-responsive promoter. These stable reporter cells may be generated using lentiviral vectors incorporating both the PtTA-GFP expression module and a drug resistance cassette, as has been done in similar systems. Reporter cells may be transiently transfected with plasmids expressing the test receptors for 24 hours, stimulated with various concentrations of the test ligand (when appropriate), and GFP reporter expression may be quantified by flow cytometry 24-48 hours later.

On can investigate the function and utility of the MESA strategy by attempting to implement it for three ligand targets, such as interleukins 10 and 12 (IL-10, IL-12) and vascular endothelial growth factor (VEGF, also called VEGF-A). These ligands are proposed due to the unique recognition challenges they comprise and for their importance to immune function in vivo. IL-10 and VEGF are both potent mediators of immune suppression in cancer, and IL-12 induces immune stimulation that counters this suppression. IL-10 and VEGF are each homodimers, and IL-12 is a heterodimer consisting of disulfide-bridged p35 and p40 subunits. Each engineered receptor may be designed based upon known mechanisms of native receptor function. The native IL-10 receptor is part of the broad cytokine receptor family, and it consists of IL-10R1 and IL-10R2 chains. IL-10R1 dimerizes upon binding IL-10 (with high affinity), after which IL-10R2 is recruited to the complex to induce signaling. Consequently, in the MESA architecture, both ER-A and ER-B may include LB domains from IL-10R1. The VEGF receptor VEGFR2 belongs to a structurally distinct family of receptor tyrosine kinases, and its extracellular domain consists of 7 immunoglobulin-like domains. However, since this ligand is also homodimeric, both ER-A and ER-B may again incorporate identical LB domains, in this case from VEGFR2. Reproducing the IL-12 receptor is more challenging, since it is composed of IL-12RB1 and IL-12RB2 chains, and each (alone) binds IL-12 with low affinity. Only the heteromeric complex binds with high affinity to induce signaling, and evidence indicates that each receptor chain recognizes a unique IL-12 subunit. Consequently, the MESA receptor chains ER-A and ER-B may each incorporate binding domains from IL-12RB1 and IL-12RB2, respectively.

In work conducted during the development of embodiments of the present invention using novel IL-10 receptors (in this case, by redirecting signaling into the TLR4 pathway using modular domain recombination), it was observed that only receptors displaying constitutive ligand-independent signaling were able to bind IL-10 with high affinity (representative results summarized in FIG. 1B). Thus, ligand binding and signal induction may be investigated separately. In addition, not all dimerization events are equivalent. An illustrative analogy comes from the erythropoietin receptor (EPOR), which is structurally related to IL-10R and other cytokine receptors. Some peptides that induce EPOR dimerization act as antagonists, indicating that dimerization is not sufficient to induce signaling. Moreover, covalently dimerized versions of these same peptides are agonists, suggesting that receptor chain orientation also regulates activation. In certain embodiments, one may use TEV PCS variants with different susceptibilities to TEV PR, in order to maximize the difference in Gal expression between uninduced and induced states (signal-to-noise ratio).

Some of the MESA strategies described above rely upon the formation of heteromeric complexes. In alternative embodiments, each chain may include both PR and TF domains separated by a PCS and oriented such that each PR domain cleaves in trans but not in cis (i.e., PR cleaves neighboring receptors upon ligand binding-induced aggregation).

In certain embodiments, one may start with a native receptor mechanism-based strategy more like that used by Barnea et. al. For example, in the case of IL-12, the intracellular domain of IL-12R1 could be fused to PCS-TF and PR could be fused to IL-12R2, such that assembly (or perhaps rearrangement) of the functional signaling complex induces PR-mediated release of the TF.

In some embodiments, the present invention provides cell-based biosensors that perform multifactorial logical evaluation of extracellular signals using the MESA receptors described herein, which transduce extracellular cues into synthetic pathways. Such pathways may be constructed into genetic circuit architectures that can process information in useful ways. For example, one may engineer cells to perform multifactorial evaluations of extracellular inputs using Boolean logic, which is a strategy that has been implemented to date using intracellular sensors. Successful implementation of this strategy using extracellular inputs is an important step toward building mammalian cell-based sensors that interface with natural systems in vivo. For example, initially, three representative types of circuits may be constructed. Exemplary architectures for constructing "OR", "NOT IF", and "AND" gate genetic circuits are described in FIG. 2 using generic functional descriptions. Transcriptional control may be implemented using the well-characterized systems described below. For example, certain embodiments utilize the microbial antibiotic response proteins (TetR, Pir, E) and their cognate operons. Post-transcriptional control may use miRNA that are processed into siRNA to induce RNAi. Each of these strategies may be implemented initially by transient transfection into HEK 293 cells. For the GOI, a PEST tag-destabilized version of GFP may be used, because the reduced protein half-life makes this system well-suited to monitoring transcriptional dynamics. GOI expression may be assessed using flow cytometry as before.

Figure 2:
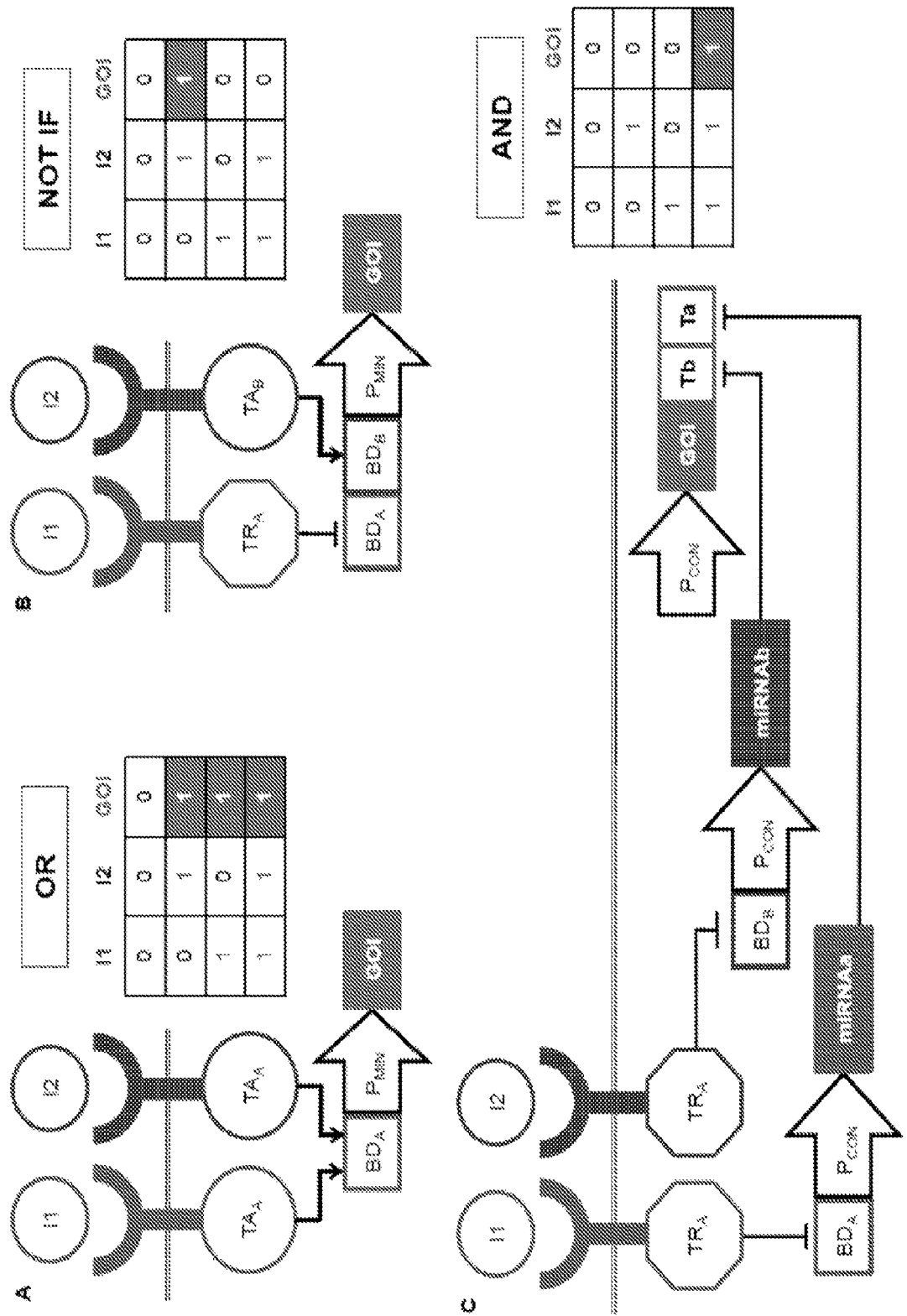
FIG. 2 shows logical evaluation of extracellular inputs. Proposed circuit architectures for performing Boolean logical evaluation including (A) "OR" (B) "NOT IF" and (C) "AND" gates. Each panel includes a truth table that indicates (qualitatively) whether GOI may be expressed given each combination of inputs. In each case, I1 and I2 are distinct inputs, GOI is a reporter gene of interest, transactivator TA, and transrepressor TR, each bind to cognate DNA TF-binding domain BD. PMIN is a minimal promoter, Pcon is a constitutive promoter, miRNAx is an engineered miRNA that is processed into an siRNA that targets sequence Tx in the 3' untranslated region of a mRNA for RNAi mediated degradation. Transcriptional control by TR, and TAi may be implemented using the microbial antibiotic response proteins TetR, Pip, and E with their cognate DNA operators, fused to either VP16 (TAi) or KRAB (TRi), as described below.

One may investigate the following circuit architectures, each of which would be useful for probing immune function: an OR gate that reports in response to either IL-10 or VEGF (i.e., a general sensor for immunosuppressive signals), a NOT IF gate that reports in response to IL-10 but only when IL-12 is absent (i.e., a sensor for uniformly immunosuppressive signals), and an AND gate that reports only in response to IL-10 and VEGF (i.e., a sensor specific for multimodal immunosuppressive signals). After characterizing the qualitative behavior of these circuits (predicted in truth tables in FIG. 3), one may also characterize the quantitative function of these circuits. These investigations may be facilitated by our choice of engineered transcription factors, since the efficiency of intracellular signal transduction may be modulated experimentally by adding antibiotic to the culture medium. Plasmid doses may also be varied to modulate the level of engineered receptor expression. Using these tunable parameters, one may determine the sensitivity of these circuits to various input combinations and strengths (concentrations) and characterize the resulting transfer functions (quantitative relationships between inputs and outputs). One may also evaluate the dynamic responses of these circuits when extracellular inputs are removed from the system (e.g., by replacing the culture medium). To facilitate these analyses, one may use computational mathematical modeling, as has previously been done for other intracellular genetic circuits. An important extension may be developing systems for stably expressing these circuits and characterizing their performance under these expression conditions. Important considerations are that lentivirus vectors are limited to a cargo length of ~8,000 bp, and using multiple vectors may necessitate using several independent antibiotic selections (such as puromycin, G418-sulfate, hygromycin, blasticidin, and zeocin-resistance genes, each of which has been used). More importantly, expression from lentiviral vectors varies quantitatively depending on the site at which the vector pseudo-randomly integrates into the host genome. One may need to evaluate the influence of this effect on circuit performance, stability, and variability. Strategies for coping with these challenges include expressing both receptor chains (ER-A and ER-B) from a single multicistronic lentiviral vector, which reduces the number of vectors required. Bicistronic expression would suffice for implementing even the relatively more complicated "AND" gate (FIG. 2). It certain embodiments, it might be possible to reduce the effect of integration site variability by transducing each cell with multiple copies of each vector, but this must be investigated. These studies may facilitate the translation of these and other sensory circuit architectures to a variety of cellular platforms. If KRAB-mediated silencing confers unfavorable circuit performance (e.g., slow responses or high background silencing due to the epigenetic mechanism of repression), an alternative is to implement transcription repression via steric hindrance using the Lac system, by inserting lacO sites between the promoter and GOI. If receptor sensitivity is insufficient, it is also possible to add positive feedback "amplifiers" to the initial architecture.

In certain embodiments, the present invention provides cell-based probes that identify user-defined microenvironmental features in vivo. The receptors described above may be implemented in a physiologically relevant system for operation such as mammalian cell-based probes that can operate within an animal (in vivo). Such implementation requires use of a cell type suitable for use as a synthetic cell-based probe, and macrophages, for example, are an ideal cellular platform. Macrophages are cells of the innate immune system that traffic naturally to multiples sites throughout the body (especially to sites of immune activity). Importantly, both macrophage cell lines and primary bone marrow-derived macrophages (BMM) can be cultured and genetically modified in vitro. Macrophages are also an attractive choice for therapeutic applications. Adoptive transfer of engineered macrophages is amenable to clinical practice, and similar methods have been used in clinical trials in the field of cancer vaccination and immunotherapy. In these strategies, a patient's own innate immune cells are collected from a blood sample, manipulated outside the body (for example, dendritic cells may be loaded with recombinant peptides derived from tumor-associated protein antigens, or they may be genetically modified to express these antigens directly), and re-administered to the patient to carry out their intended function (in this example, this function would be to stimulate an antigen specific immune response by activating and expanding tumor-reactive cytotoxic T cells). Although the application proposed here is to employ synthetic macrophage-based probes, this analogy with therapeutic models illustrates how this concept may be extended to engineer medically-relevant synthetic mammalian cell-based devices.

For example, one may endeavor to translate several of the genetic circuits described herein to the murine RAW 264.7 macrophage cell line and to primary BMM. For example, using MESA receptors that individually sense IL-10 and VEGF, one may generate two types of sensors: one that responds to IL-10, and one that responds to VEGF. For these in vivo applications, firefly luciferase may serve as the Gal. Luciferase can be used to monitor transgene expression and immune cell trafficking in live animals. Lentiviral vectors may be used to stably transduce RAW cells and BMM to construct these single-input sensors (i.e., ER-A and ER-B, which may signal through ITA, and the PtTA-luciferase reporter construct). Responses of each these sensors to recombinant IL-10 and VEGF may be assessed in vitro by quantifying luciferase expression using a standard bioluminescence assay. Sensor transfer functions may be quantified, again using antibiotics to modulate intracellular signaling efficiency. For in vivo experiments, one may use a mouse model of melanoma, an aggressive type of cancer in which local immunosuppression plays an especially important role in disease progression. In particular, one may use the well-characterized syngeneic B16 model, in which the melanoma cell line B16 and the host animal share the same genetic background (C57/BL6 strain). Therefore, when B16 cells are injected subcutaneously, the host animal's immune system doesn't recognize the B16 cells as foreign, and they grow into a tumor. Unlike some melanomas, B16 cells do not constitutively secrete appreciable quantities of IL-10, so these cells may be engineered to overexpress IL-10 using a lentiviral vector. Similarly, other B16 lines may be engineered to overexpress VEGF. Each of these B16 lines may next be tested for their ability to stimulate the sensor lines using a transwell system, in which the two cell populations are physically separated but may exchange soluble factors through shared culture media. Finally, one may determine whether the macrophage-based sensors can function as probes that identify and discriminate between these various model tumors in live animals.

An exemplary experimental design is as follows. Tumors may be established by suspending $3\times10^5$ B16 cells (B16, B16-IL10, or B16-VEGF) in 150 microliters of phosphate-buffered saline (PBS) and injecting this volume subcutaneously into one thigh of C57/BL6 mice. Control mice may receive a PBS-only control. Tumor growth may be monitored at 2 day intervals. On day 14 (based on) or when tumors become apparent in all series, $10^7$ BMM-based sensors (or control BMM engineered to constitutively expresses luciferase) may be injected intravenously. Subsequently, at 24 hour intervals, mice are injected with D-luciferin and imaged as described. Mice may be euthanized on day 18, and tumors excised, sectioned, and stained with antibodies for tTA and luciferase to determine whether probe cells are present or activated, respectively, within the tumors. Before finalizing this experimental design, pilot studies may be performed with BMM constitutively expressing luciferase to determine (a) how many BMM must be injected in order to visualize them, (b) how long BMM remain detectable after injection, and (c) where these control BMM traffic in the presence or absence of B16 tumors. In sum, these experiments may evaluate this implementation of the novel concept of mammalian cell-based probes, and they may also provide insights into patterns of IL-10 and VEGF expression in this model of melanoma.

In macrophages, it is important to assess whether signaling through engineered receptors remains orthogonal. For example, since macrophages express native IL-10R1 and IL-10R2, these may compete with or interact with the engineered receptors. The significance of this effect could be evaluated by alternately over-expressing or knocking down (by RNAi) the native receptor chains and determining whether this modulates the sensor cell's transfer function. If the cell-based probes fail to localize to the site of interest, or fall to remain at those sites, it may be possible to enhance localization by linking the sensor pathway to cellular chemotaxis. For example, one strategy would be to engineer the cell such that activation of the sensor genetic circuit also induces the expression of a constitutively active form of the chemokine receptor CCR2, which is involved in chemotaxis. This strategy could be elaborated upon by knocking down native chemotaxis-inducing receptors (e.g., CCR2, CCR5, and CCR3) using RNAi. These localization challenges may be more pronounced when attempting to probe sites that do not naturally secrete macrophage-recruiting chemokines as tumors do.

In certain embodiments, the MESA biosensors described herein are implemented in mammalian cells, and are employed in any suitable use, such as in vitro laboratory assays (e.g., to detect/quantify specific analytes), as powerful experimental tools for studying in vivo animal models (e.g., engineered cell-based biosensors could be adoptively transferred, generated from transplanted bone marrow, or genetically engineered in a transgenic animal to monitor extracellular species in real time in living animals), and as human therapeutics (e.g., for engineering cell-based therapies that probe their environment and delivery a therapeutic payload only at desirable locations). In other embodiments, the MESA biosensors described herein are employed with other cell types, such as insect cells or microbes (e.g., yeast) to create cell-based biosensors for applications in biotechnology.

Any type of suitable ligand binding domain (LB) can be employed with the receptors of the present invention. Ligand binding domains can, for example, be derived from either an existing receptor ligand-binding domain or from an engineered ligand binding domain. Existing ligand-binding domains could come, for example, from cytokine receptors, chemokine receptors, innate immune receptors (TLRs, etc.), olfactory receptors, steroid and hormone receptors, growth factor receptors, mutant receptors that occur in cancer, neurotransmitter receptors. Engineered ligand-binding domains can be, for example, single-chain antibodies (see scFv constructs discussion below), engineered fibronectin based binding proteins, and engineered consensus-derived binding proteins (e.g., based upon leucine-rich repeats or ankyrin-rich repeats, such as DARPins).

Any suitable extracellular space (ESP) can be used with the receptors of the present invention. In certain embodiments, the ESP is from 0-30 amino acids long (e.g., 1 . . . 5 . . . 15 . . . 25 . . . or 30), where each amino acid can be, for example, any of the 20 naturally occurring amino acids. In certain embodiments, ESP can be nonstructured or comprised partially or entirely of amino acids predicted to fold into a secondary structure (i.e., an alpha helix) or a tertiary structure. ESP sequences flanking the TM domain may be selected to adjust the stability of the TM in the membrane (i.e., adding a polar or charged residue to ESP next to TM should make it more difficult for that amino acid to be pulled into the membrane).

Any suitable transmembrane domain (TM) can be used with the receptors of the present invention. In certain embodiments, the TM is, for example, a TM domain taken from an existing receptor (e.g., TLR4, CD28, etc.) or engineered using a novel sequence, for example using TM consensus sequence features.

Any suitable intracellular spacer (ISP) can be used with the receptors of the present invention. In particular embodiments, no ISP is present. In certain embodiments, the ISP is, for example, 0-30 amino acids long (e.g., 1, 2, 3, 4, 5, 6, ... 15 ... 25 ... or 30 amino acids) where each amino acid can be, for example, any of the 20 naturally occurring amino acids. ISP can be, for example, nonstructured or comprised partially or entirely of amino acids predicted to fold into a secondary structure (i.e., an alpha helix) or a tertiary structure. ISP sequences flanking the TM domain may be selected to adjust the stability of the TM in the membrane (i.e., adding a polar or charged residue to ESP next to TM should make it more difficult for that amino acid to be pulled into the membrane).

Any suitable protease cleavage sequence may be employed with the receptors of the present invention. In certain embodiments, the PCSs, for example, are varied by mutating the amino acid at the P1' position, for example, to any of the 20 amino acids or by introducing 1 or more mutations into the rest of the PCS, e.g., to modify kinetic parameters governing PCS cleavage.

The present invention is not limited to any particular protease or corresponding protease cleavage site. In some embodiments, the protease and cleavage site are from a virus. For example, in certain embodiments, the protease and protease cleavage site are from a virus selected from: tobacco etch virus (TEV), a chymotrypsin-like serine protease and corresponding cleavage sites, alphavirus proteases and cleavage sites, Hepatitis C virus proteases (e.g., N S3 proteases) and corresponding cleavage sites, chymotrypsin-like cysteine proteases and corresponding cleavage sites, papain-like cysteine proteases and cleavage sites, picornavirus leader proteases and cleavage sites, HIV proteases and cleavage sites, Herpesvirus proteases and cleavage sites, and adenovirus proteases and cleavage sites (see, Tong, Chem. Rev. 2002, 102, 4609-4626, herein incorporated by reference in its entirety). In particular embodiments, the proteases and cleavage sites are bacterial in original, such as, for example, from *Streptomyces griseus* protease A (SGPA), SGPB, and alpha-lytic protease and corresponding cleavage sites. In some embodiments, the proteases and cleavage sites are mammalian. For example, the proteases could be one of the five major classes of proteases known in mammals which include serine proteases, cyteine proteases, metallo proteases, aspartic proteases, and thereonine proteases (see, e.g., Turk et al., The EMBO Journal, 2012, 31, 1630-1643; Lopez-Otin and Overall, 2002, Nat. Rev. Mol. Cell Biol., 2:509-519; Overall and Blobel, 2007, Nat. Rev. Mol. Cell Biol., 8: 245-257; and Lopez-Otin and Bond, 2008, J. Biol. Chem., 283:30422-30437, all of which are herein incorporated in their entireties by references).

Figure 23:
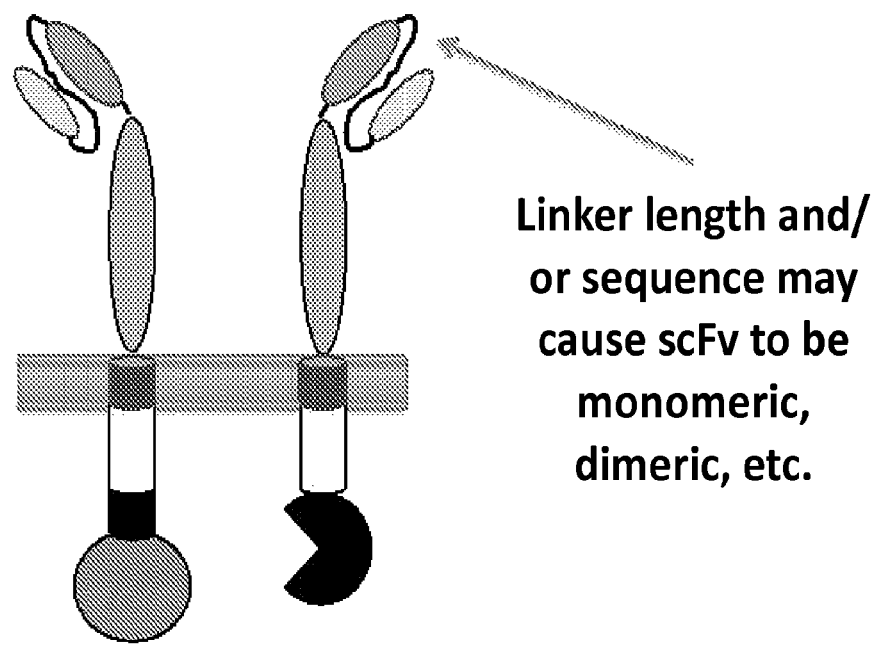
FIG. 23 shows an exemplary scFv-based MESA scheme, in which scFv linker is selected such that in this case, PC and TC do not dimerize in a ligand-independent fashion. Variants on this scheme would be to engineer scFv (and/or other MESA domains) to favor homodimerization (e.g., TC-TC and/or PC-PC), such that these dimerized chains are brought together in a hetero-fashion (e.g., TC-TC multimerizes with PC-PC) upon ligand binding.

In certain embodiments, MESA constructs may be designed using engineered ligand binding domains based upon single chain antibody variable fragments (scFv) (FIG. 23). The loop linking heavy and light chain-derived fragments of an scFv may be designed (both in length and sequence) to favor monomeric scFvs, dimeric scFvs, trimeric scFvs, etc. (8). Loop length may be, for example, 0-30 amino acids long, where each amino acid may be, for example, any of the 20 naturally occurring amino acids. One may select a loop to favor scFvs (depicted) or to favor homomultimeric scFvs (see description of FIG. 23 above). ScFv may be engineered, for example, from isolated antibody, BCR, or TCR sequences, or they may be isolated from a random library, such as phage-display, bacterial-display (9), or yeast-display (10).

Figure 24:
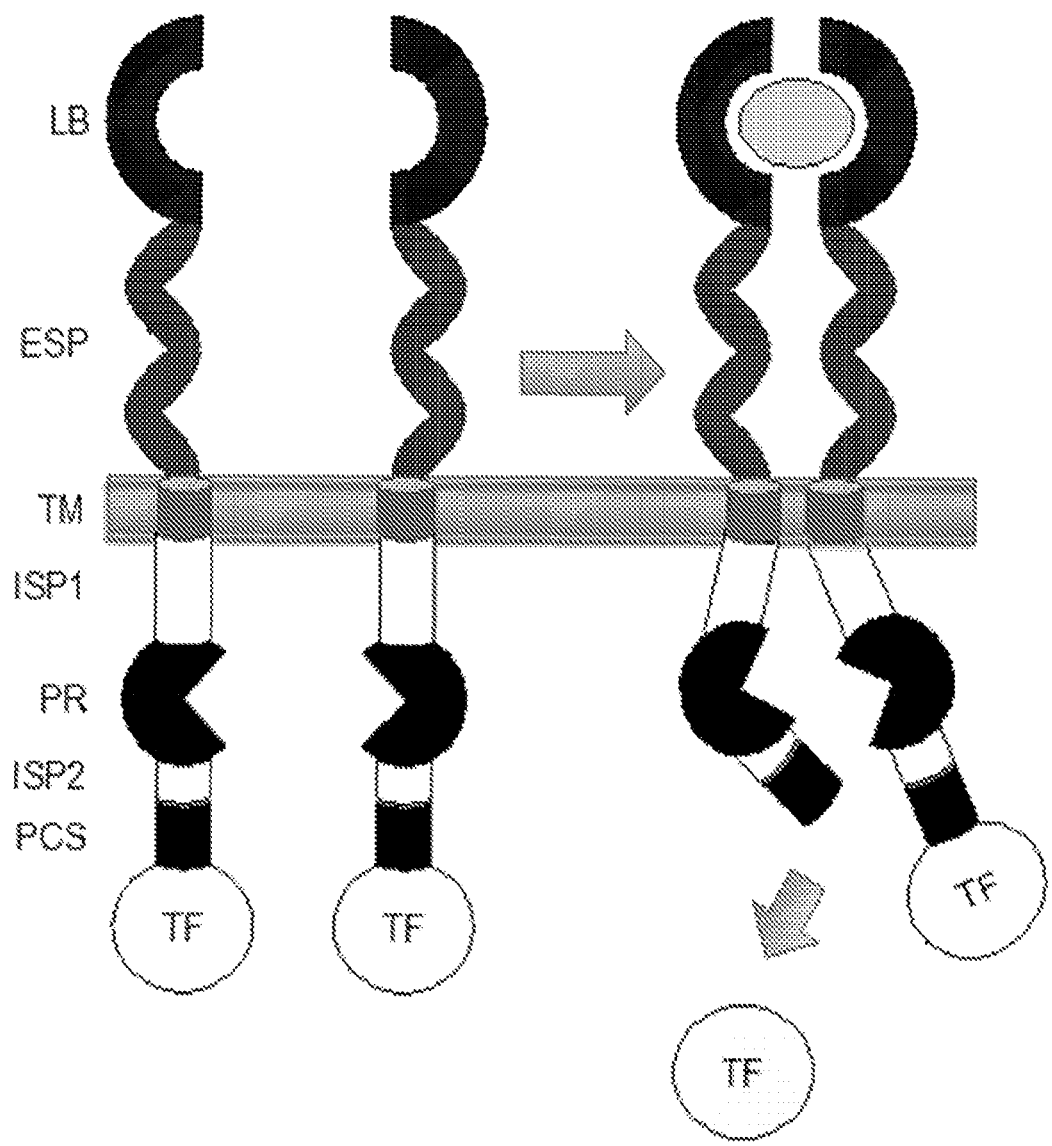
FIG. 24 shows exemplary MESA constructs utilizing a single-chain design. In this scheme, PR is separated from PCS on its own chain by ISP2, with all sequences and orientations selected such that cis-cleavage is prevented, but trans-cleavage is possible when LB are dimerized by binding to the target ligand.

In certain embodiments, an "all in one receptor" approach is employed. For example, the two chain MESA scheme (TC+PC) may be varied such that all components are included on a single chain, and ligand binding-induced homodimerization induces signaling (FIG. 24). In FIG. 24, the receptor includes both ISP1 and ISP2, which could be optimized in length (e.g., 0-30 amino acids) and composition (e.g., any of the 20 naturally occurring amino acids at any position) to optimize receptor performance.

In particular embodiments, the receptors are employed in yeast cells. For example, one could employ yeast-specific expression plasmids that include N-terminal sequences targeting the MESA receptor to the secretory pathway to enable expression on the yeast cell surface. One could also include a transcription factor that includes a previously-described additional nuclear localization sequence that enhances tTA activity in yeast (11). TM domains could be taken from a yeast protein sequence, such as Mid2.

Figure 25:
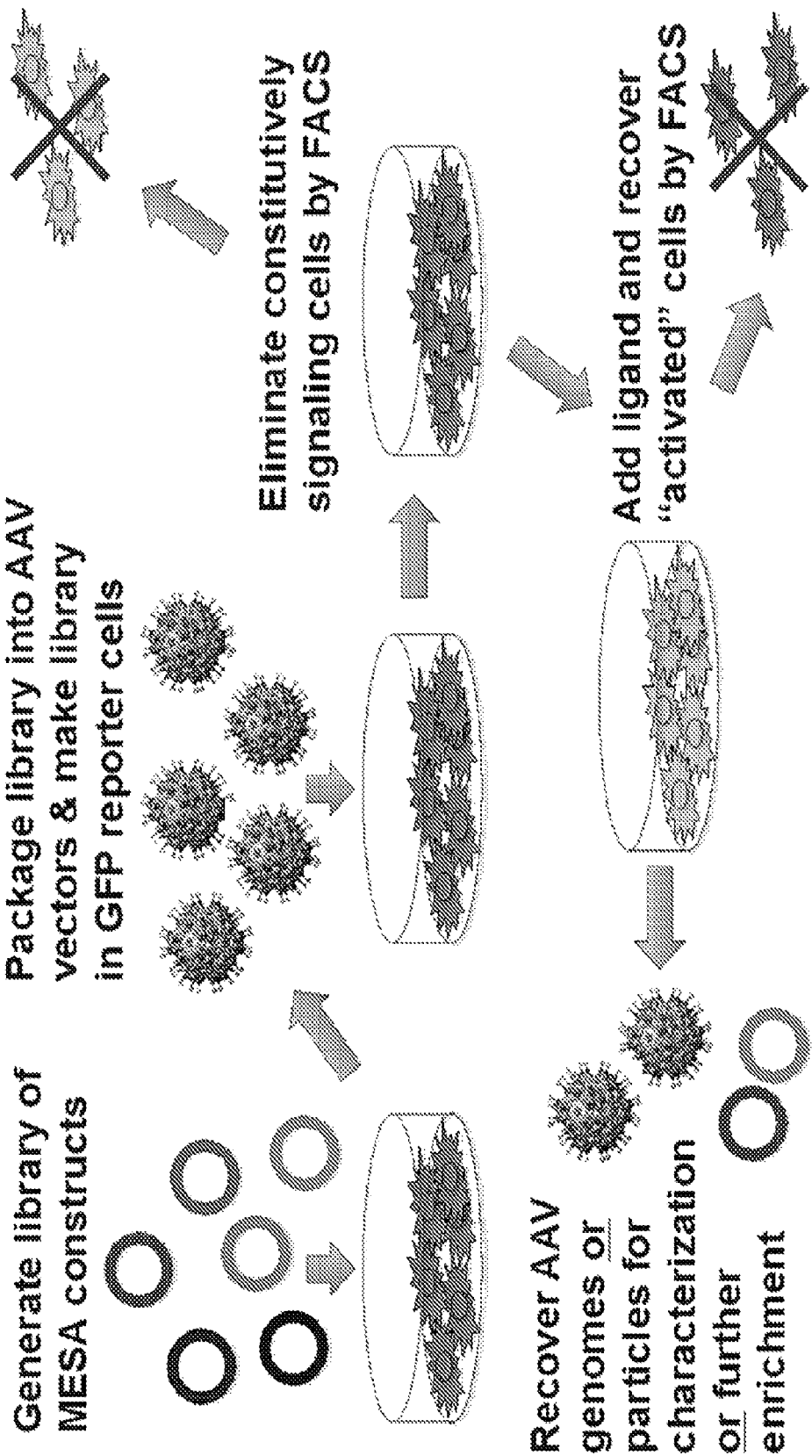
FIG. 25 shows an exemplary method for directed evolution of MESA receptors. This directed evolution scheme could be used to enhance MESA receptors that exhibit desirable on-off states. Enrichment over several rounds (e.g., without introducing additional diversity) could select for more robust receptors or receptors that perform well when expressed at different levels. A variation upon this scheme would be to introduce additional genetic variability into recovered genomes (e.g., using error-prone PCR), and then to take this new diversified genetic library back to the viral packaging stage before proceeding to perform additional selection as depicted. Here, adeno-associated virus (AAV)-based expression vectors are used to enable a setup in which each cell expresses only one MESA variant.

In certain embodiments, directed evolution could be used to optimize performance characteristics including, for example: low background signaling, enhanced signal-to-noise ratio, enhanced sensitivity for low ligand concentrations, and enhanced dynamic range (differential responsiveness over a wider range of ligand concentrations). Directed evolution could be performed, for example, by a scheme in which (a) a library of genetic variants upon an initial receptor design are created (b) each variant is expressed in a separate cell (c) this pool of cells is exposed to a functional screen to either eliminate cells (and therefore receptor variants) exhibiting undesirable activity or retain cells (and therefore receptor variants) that exhibit some desirable activity. This process could be repeated to enrich for variants with desirable properties. A variation upon this method would be to isolate variants in this fashion after 1 or more rounds of enrichment, introduce additional genetic diversity into this library, and return to the cell-based screening; this could be repeated for multiple rounds until the pool or individual constructs within the pool exhibit properties that meet some threshold for considering it a success. One way to implement this scheme is depicted in FIG. 25. Briefly, one could (a) generate a library of DNA sequences encoding MESA variants using error-prone PCR or other molecular biology techniques to incorporate chemically synthesized DNA oligonucleotides including variation at defined positions; variation could be introduced at ISP, PCS, PR, TM, ESP, LB, or combinations of these sites, (b) each variant could be cloned into an expression vector based upon adeno-associated virus (AAV), viral vectors could be packaged by standard techniques, and AAV vectors could be used to transduce cells at a ratio of viruses to cells such that each cell expresses only one variant of the MESA library, and then (c) this pool of cells that expresses the MESA library (one variant per cell) could be used for cell-based assays; for example, cells could be transfected or transduced with a reporter construct that reads out MESA signaling by inducing expression of a fluorescent protein, and then the MESA pool of reporter-bearing cells could be sorted using fluorescence assisted cell sorting (FACS) based upon whether the reporter construct is induced or not when exposed to zero ligand or some finite quantity of ligand (see FIG. 25).

EXAMPLES

Example 1

MESA Receptors

This Example describes exemplary MESA constructs with various protease cleavage sites (PCSs) and intracellular spacers (ISPs) that are absent (zero amino acids) or six amino acids in length.

Figure 3:
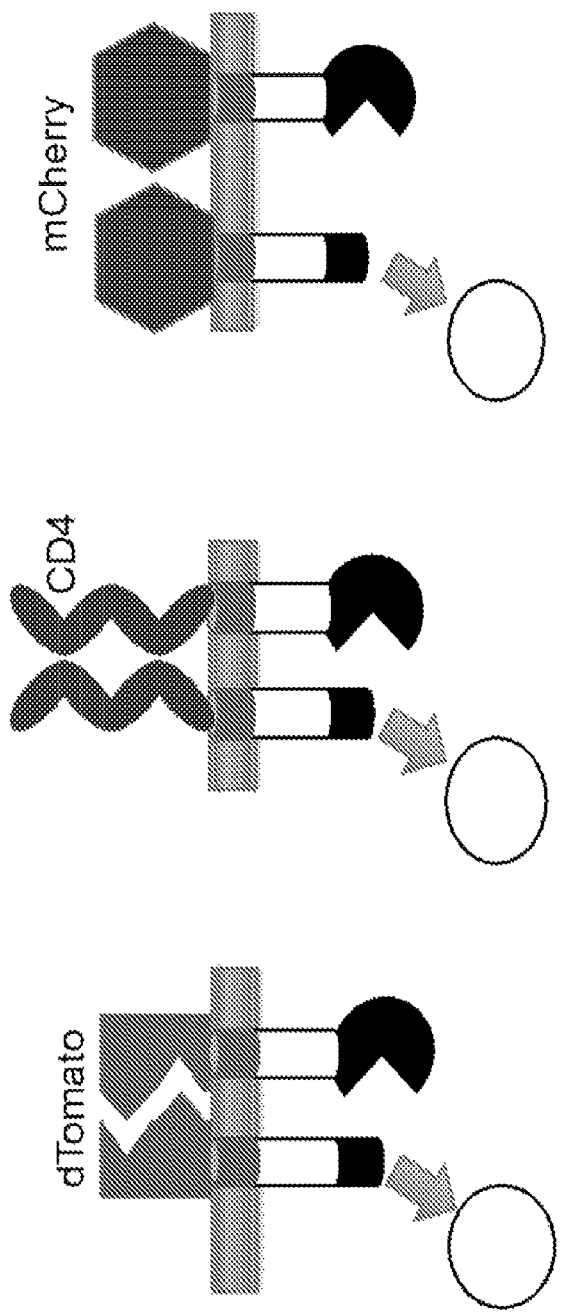
FIG. 3 shows a series of model MESA receptors, including those whose extracellular domains are based upon dTomato, CD4, or mCherry.

It is preferable that the receptors in the MESA platform signal as little as possible in the absence of ligand (e.g., system exhibits low background) and that dimerization/multimerization induces enhanced reporter output (e.g., system exhibits adequate signal-to-noise). In order to investigate how features contained in the intracellular domains of the MESA receptor chains impact these performance characteristics, a series of model MESA receptors were developed that serve as limiting cases because their extracellular domains interact in a predictable, ligand-independent fashion (FIG. 3).

Receptors incorporating mCherry ectodomains do not interact by any known mechanism, so these receptors provide a measure of diffusion-limited behavior (contact occurs only via random diffusion of receptors within the membrane) (1). Receptors incorporating an ectodomain based upon the CD4 ectodomain are expected to form dimers via a covalent disulfide bond, although both monomers and dimers are typically observed on the cell surface (2, 3). Receptors incorporating an ectodomain based upon dTomato are expected to exist only in a dimeric state, since dTomato is an "obligate dimer," and monomeric forms of this protein are unstable (4).

These models were utilized to explore two important features of MESA receptor design space. Because background (ligand-independent) cleavage of the target chain (TC) by the protease chain (PC) likely depends upon how easily the protease (e.g., Tobacco Etch Virus (TEV) protease used in this Example) can access its protease cleavage sequence (PCS) when TC and PC encounter one another via random diffusion, this Example constructed TC and PC that include intracellular spacers (ISP) of different lengths. In addition, kinetics of PCS cleavage are expected to strongly impact both background and signal-to-noise in this system.

Figure 4:
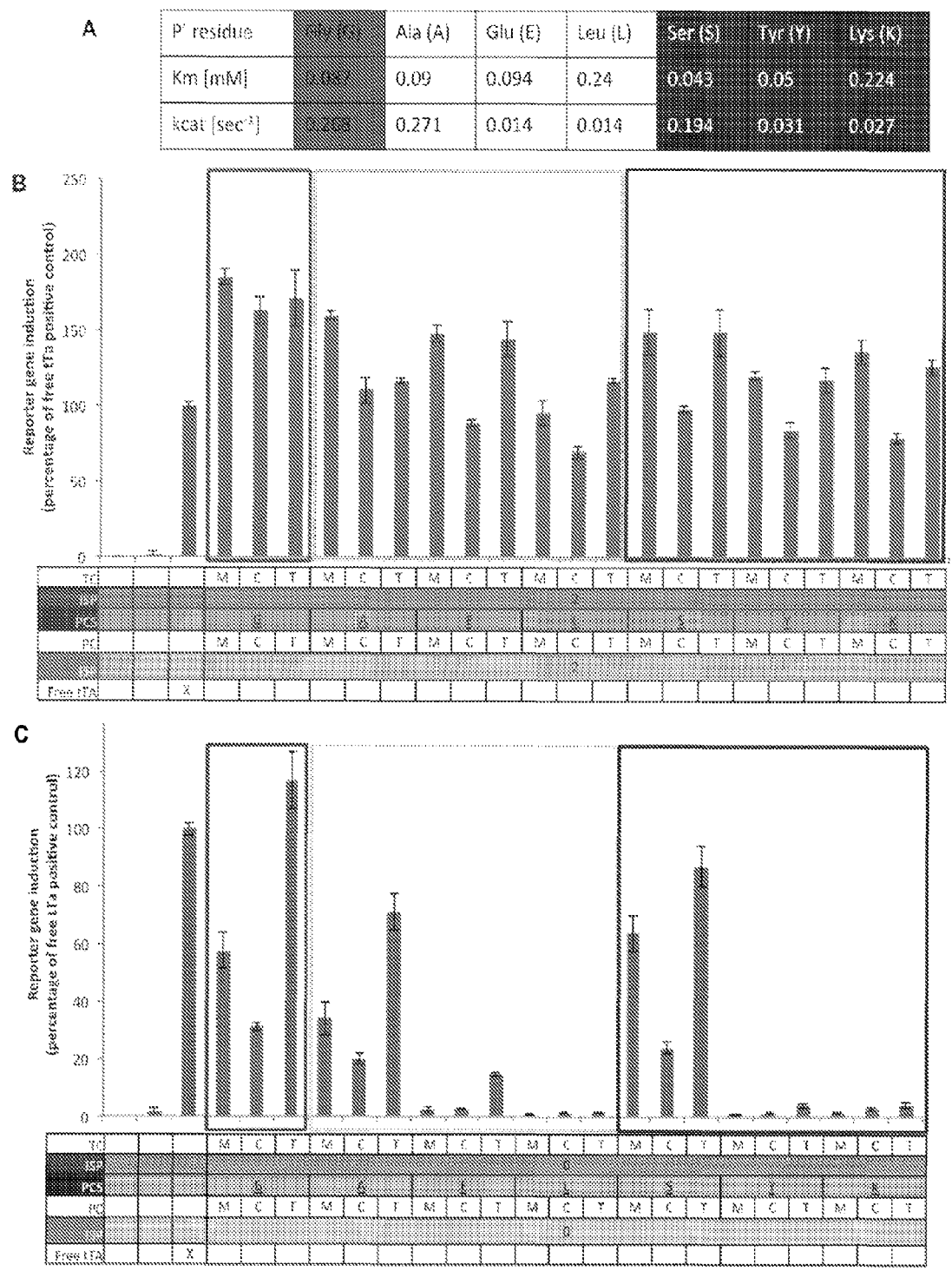
FIG. 4 shows the results from Example 1, including how varying features of intracellular receptor architecture impact relative signaling efficiency of model MESA receptors.

Variants of the canonical TEV PCS sequence have previously been described, such that by varying the final P1' amino acid in the PCS (i.e., X in ENLYFQX, SEQ ID NO:33), it is possible to vary either or both of the Michaelis-Menten parameters associated with a given PCS (5) (FIG. 4A). In FIG. 4, results of an experiment are shown that demonstrate a representative exploration of MESA receptor design space that involves each of the features described above. Notably, when nonstructured ISP of 2 amino acids, plus an additional 4 charged residues adjacent to the membrane (for a total of 6 amino acid ISP) are used on each chain, there is no discernible trend of increased reporter activation for dTomato-based receptors (dimers) vs. mCherry-based receptors (monomers) (FIG. 4B). However, when the ISP is eliminated (i.e., 0 amino acids long; here, the membrane-proximal 4 residues are removed as well), a marked increase in signaling is observed for dTomato vs. mCherry-based receptors, and this is true for some but not all choice of amino acid in the P1' position of PCS.

Note that in this Example, all receptors were expressed at a high level, and altering TC or PC expression level (e.g., by lowering transfected plasmid dose), or the relative TC vs. PC stoichiometry (e.g., by altering transfected plasmid stoichiometry), may further improve performance characteristics, such as signal-to-noise, for any given receptor (TC/PC) pair.

FIG. 4 shows the results from this Example, including how varying features of intracellular receptor architecture impact relative signaling efficiency of model MESA receptors. FIG. 4A shows predicted kinetic constants for cleavage of PCS sequences in which the final or P1' amino acid (i.e., X in ENLYFQX (SEQ ID NO:33)) is selected as indicated (5). FIGS. 4B and 4C show results from experiments where human HEK293FT cells were transfected with a tTA-responsive reporter plasmid and either plasmids encoding both target chain (TC) and protease chain (PC) receptors containing extracellular domains comprised of mCherry (M), dTomato (T) or CD4 ectodomain (C), or with a plasmid encoding free tTA as a control (where indicated). Transfected cells were incubated for 24 hours, and then expression of the tTA-induced reporter gene (GFP) was quantified by flow cytometry. An additional plasmid encoding DsRedExpress2 was included in all samples, such that only successfully transfected cells were analyzed for GFP expression, and GFP expression was normalized as a percentage of the free tTA positive control. In each case, the TC and PC contain an intracellular spacer (ISP) of 6 amino acids (B) or 0 amino acids (C), as indicated by "ISP". Amino acid in P1' position of PCS on TC is indicated by "PCS". Data are presented as mean+/–standard deviation for experimental triplicates. FIGS. 7-18 show schematic views, as well as nucleic and amino acid sequences, of the constructs employed in this Example.

Example 2

MESA Receptors with Inhibited Proteases

This Example describes exemplary MESA constructs with self-inhibited proteases and fluorescently labeled transcription factors.

Figure 5:
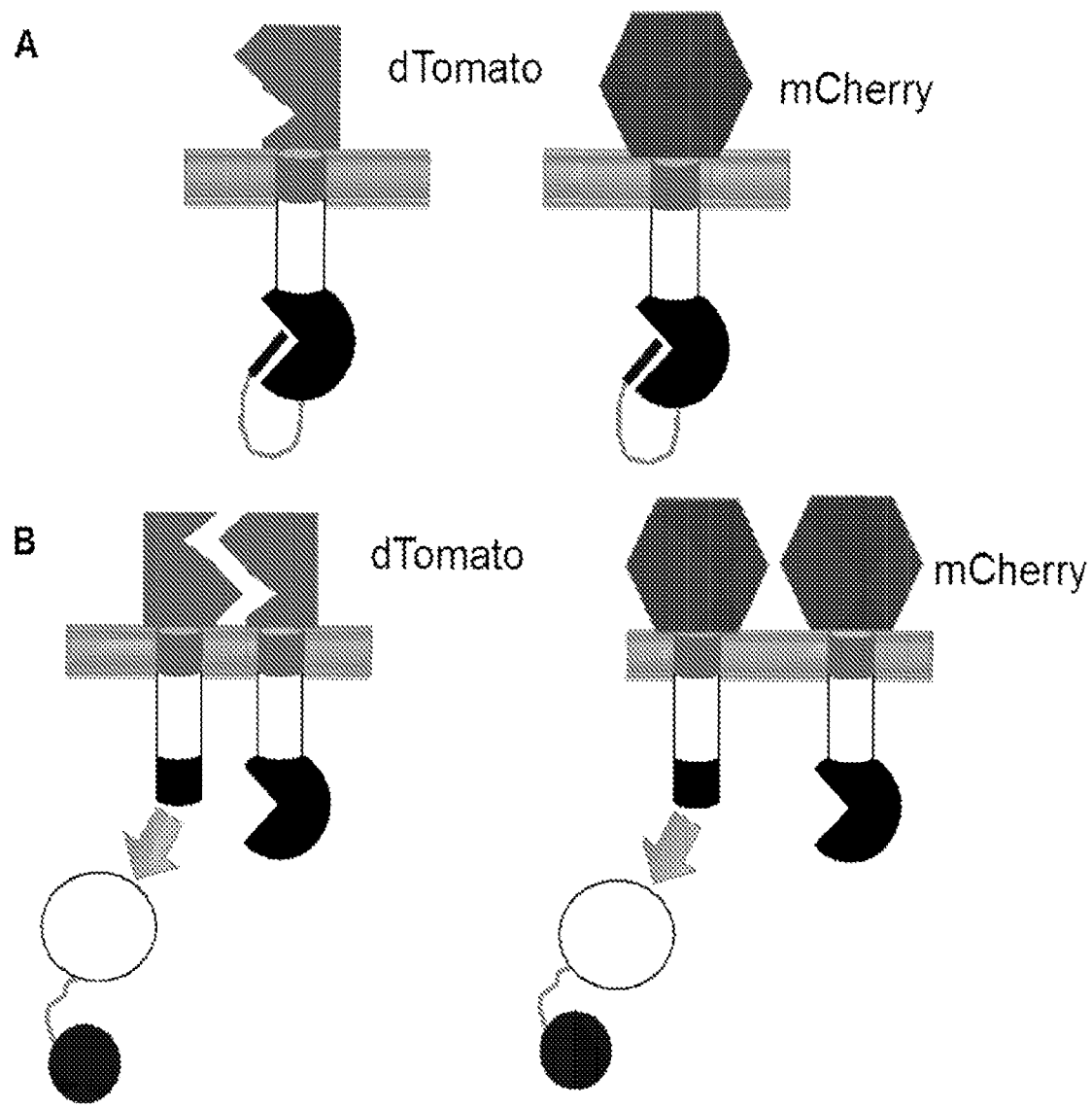
FIG. 5 shows exemplary MESA receptor design variants.

As part of this Example, MESA constructs were altered by replacing the highly active version of TEV that is commonly used in molecular biology (used in Example 1) with an auto-inhibitory variant of the TEV protease (FIG. 5). The highly active TEV variant is mutated to prevent autocleavage, since wild-type TEV is less active after it autocleaves post translationally (6). In the native TEV protease, the cleaved "tail" of TEV remains associated with the catalytic site where it presumably competes with other PCS ligands (7). Therefore, in this Example, an autoinhibitory TEV variant (TEV-AI) was designed that includes the WT TEV sequence up through the cleaved tail, and it was incorporated into PC designs (FIG. 5). In another variation, the tTA domain was genetically fused to BFP (blue fluorescent protein) to enable quantification and visualization of protease chain (PC) expression levels (which might vary with choice of ectodomain), since in this framework, both target chain (TC) and PC contain a red fluorescent protein (mCherry or dTomato) (FIG. 5). The tTA-BFP fusion could also enable one to determine where or when tTA is released from the rest of TC.

In this Example, it was demonstrated that TEV-AI does improve receptor performance vs. highly active TEV, and any differences in receptor expression level were normalized by employing the tTA-BFP fusion. Parallel transfections of TC vs. TC+PC were performed (keeping total plasmid transfection dose and efficiency constant). Overall, this Example illustrates how the modular MESA receptor design scheme can be harnessed to iteratively improve receptor performance characteristics, in this case including simultaneous reduction of background and enhancement of the signal-to-noise ratio.

Figure 6:
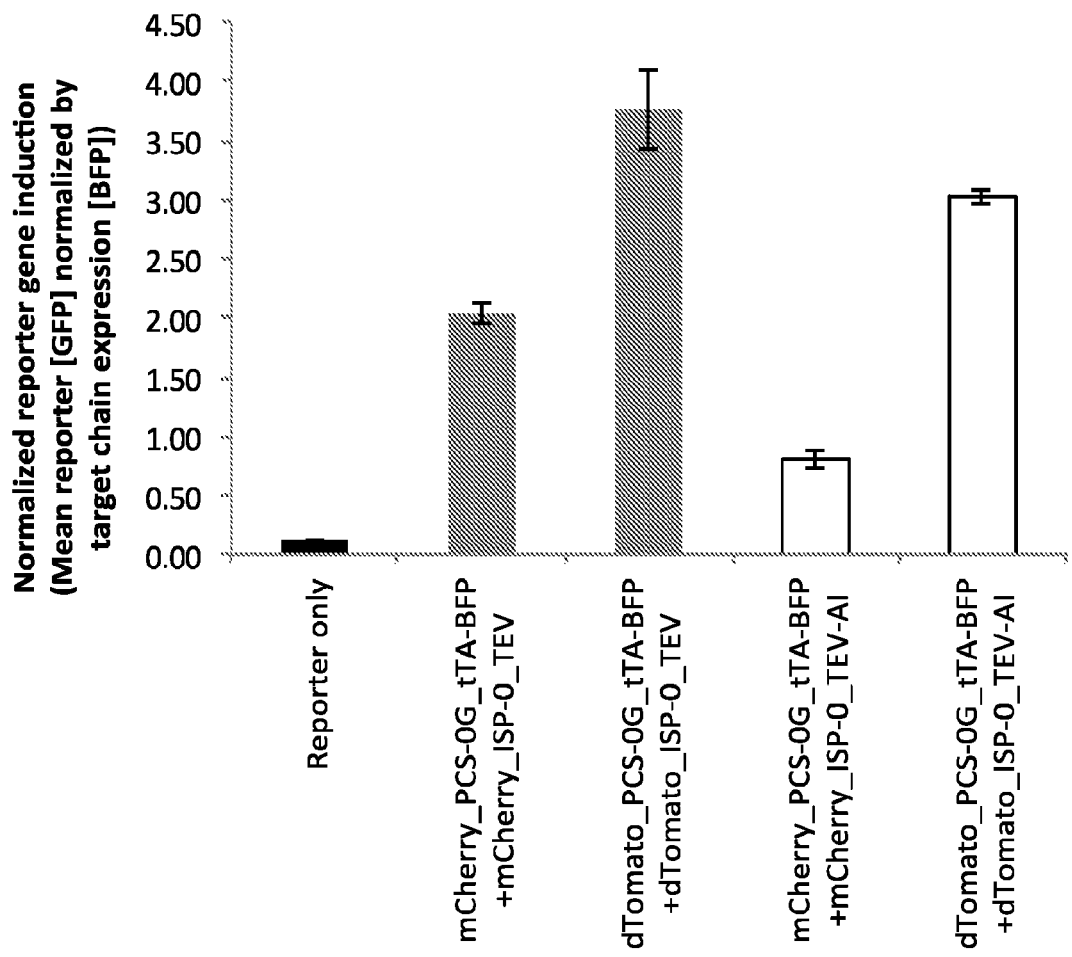
FIG. 6 shows results from Example 2 and exemplary optimization of MESA performance. This Example illustrated one method by which the MESA receptor design may be optimized to improve receptor performance by using auto-inhibitory proteases to reduce background.

The results of this Example are shown in FIG. 6. In this Example, mCherry and dTomato-based receptors were constructed using either standard TEV protease (TEV, grey bars) or autoinhibitory TEV (TEV-AI, white bars). General transfection and fluorescence assay method were similar to that described for FIG. 4. In each case, reporter gene induction (GFP) is normalized to BFP signal measured from a parallel transfection of TC alone (BFP signal is from tTA-BFP in TC), to control for differences in the expression of mCherry- and dTomato-based TC. Reduction of signal from mCherry-based receptors indicates reduction in background. Enhancement of the difference between mCherry- and dTomato-based receptors indicates increased signal-to-noise ratio. MESA constructs used here are shown in FIGS. 19, 20, 21, and 22.

In some embodiments, subjects are treated with a vector or set of vectors: a) genes encoding the biosensors (e.g., including functional domains) and b) genes encoding the genetic circuitry that would cause a cell to express a therapeutic gene in response to either (a) the output of one biosensor or (b) the output of a gene circuit composed of multiple biosensors along with relevant information processing circuitry (as depicted in FIG. 2). In this regard, the therapeutic vectors may, for example, comprise genes for both the biosensors and constructs downstream of the biosensors.

REFERENCES

All of the following references are herein incorporated by reference.
1. Panter G & Jerala R (2011) The ectodomain of the Toll-like receptor 4 prevents constitutive receptor activation. J Biol Chem 286(26):23334-23344.
2. Matthias L J, Yam P T, Jiang X M, Vandegraaff N, Li P, Poumbourios P, Donoghue N, & Hogg P J (2002) Disulfide exchange in domain 2 of CD4 is required for entry of HIV-1. Nat Immunol 3(8):727-732.
3. Wouters M A, Lau K K, & Hogg P J (2004) Cross-strand disulphides in cell entry proteins: poised to act. Bioessays 26(1):73-79.
4. Shaner N C, Campbell R E, Steinbach P A, Giepmans B N, Palmer A E, & Tsien R Y (2004) Improved monomeric red, orange and yellow fluorescent proteins derived from Discosoma sp. red fluorescent protein. Nat Biotechnol 22(12):1567-1572.
5. Kapust R B, Tozser J, Copeland T D, & Waugh D S (2002) The P1' specificity of tobacco etch virus protease. Biochem Biophys Res Commun 294(5):949-955.
6. Kapust R B, Tozser J, Fox J D, Anderson D E, Cherry S, Copeland T D, & Waugh D S (2001) Tobacco etch virus protease: mechanism of autolysis and rational design of stable mutants with wild-type catalytic proficiency. Protein Eng 14(12):993-1000.
7. Nunn C M, Jeeves M, Cliff M J, Urquhart G T, George R R, Chao L H, Tscuchia Y, & Djordjevic S (2005) Crystal structure of tobacco etch virus protease shows the protein C terminus bound within the active site. J Mol Biol 350(1):145-155.
8. Hudson P J & Kortt A A (1999) High avidity scFv multimers; diabodies and triabodies. J Immunol Methods 231(1-2):177-189.
9. Georgiou G, Stathopoulos C, Daugherty P S, Nayak A R, Iverson B L, & Curtiss R, 3rd (1997) Display of heterologous proteins on the surface of microorganisms: from the screening of combinatorial libraries to live recombinant vaccines. Nat Biotechnol 15(1):29-34.
10. Kieke M C, Cho B K, Boder E T, Kranz D M, & Wittrup K D (1997) Isolation of anti-T cell receptor scFv mutants by yeast surface display. Protein Eng 10(11):1303-1310.
11. Lee T H & Maheshri N (2012) A regulatory role for repeated decoy transcription factor binding sites in target gene expression. Mol Syst Biol 8:576.

All publications and patents mentioned in the present application are herein incorporated by reference. Various modifications and variations of the described methods and compositions of the invention may be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A composition comprising:
   i) first and second exogenous sensors wherein said first exogenous sensor comprises:
      a) a first ligand binding domain,
      b) a transmembrane domain,
      c) a protease cleavage site, and
      d) a functional domain;
      and wherein said second exogenous sensor comprises:
      e) a second ligand binding domain,
      f) a transmembrane domain, and
      g) a protease domain; and
   ii) a cell, wherein said first and second exogenous sensors are located in the cell membrane such that the first and second ligand binding domains are located outside said cell; and wherein said protease cleavage site and said functional domain are located inside said cell; and
   wherein said first and second ligand binding domains bind the same ligand outside said cell, and
   wherein said first and second exogenous sensors are configured such that said protease domain will cleave said protease cleavage site when said first and second ligand binding domains bind said same ligand outside said cell.

2. The composition of claim 1, further comprising third and fourth exogenous sensors.

3. The composition of claim 2, wherein
   i) said third exogenous sensor comprises:
      a) a third ligand binding domain,
      b) a transmembrane domain,
      c) a protease cleavage site, and
      d) a functional domain;
      and wherein said fourth exogenous sensor comprises:
      e) a fourth ligand binding domain,
      f) a transmembrane domain, and
      g) a protease domain; and
   ii) a cell, wherein said third and fourth exogenous sensors are located in the cell membrane such that the third and fourth ligand binding domains are located outside said cell; and wherein said protease cleavage site and said functional domain are located inside said cell; and
   wherein said third and fourth ligand binding domains bind the same ligand outside said cell which ligand is a different ligand than the ligand bound by the first and second ligand binding domains, and
   wherein said third and fourth exogenous sensors are configured such that said protease domain of the fourth exogenous sensor will cleave said protease cleavage site of the third exogenous sensor when said third and fourth ligand binding domains bind said same ligand outside said cell.

4. The composition of claim 1, wherein said first exogenous sensor or said second exogenous sensor further comprises an extracellular spacer.

5. The composition of claim 3, wherein said third exogenous sensor or said fourth exogenous sensor further comprises an extracellular spacer.

6. The composition of claim 1, wherein said first exogenous extracellular or said second exogenous extracellular sensor further comprises an intracellular spacer that is one, two, three, four, five, or six amino acids in length.

7. The composition of claim 3, wherein said third exogenous extracellular or said fourth exogenous extracellular sensor further comprises an intracellular spacer that is one, two, three, four, five, or six amino acids in length.

8. The composition of claim 1, wherein said functional domain is a transcription factor.

9. The composition of claim 8, further comprising a genetic construct, wherein said genetic construct is configured to express a gene in response to said transcription factor and said genetic construct is located in said cell.

10. The composition of claim 9, wherein said gene is a reporter gene or a therapeutic gene.

11. A composition comprising:
    i) first and second exogenous sensors wherein said first exogenous sensor comprises:
       a) a first ligand binding domain, said ligand binding domain comprising an antibody that binds a ligand or a fragment of an antibody that binds a ligand;
       b) a transmembrane domain,
       c) a protease cleavage site, and
       d) a functional domain;
       and wherein said second exogenous sensor comprises:
       e) a second ligand binding domain,
       f) a transmembrane domain, and
       g) a protease domain; and
    ii) a cell, wherein said first and second exogenous sensors are located in the cell membrane such that the first and second ligand binding domains are located outside said cell; and wherein said protease cleavage site and said functional domain are located inside said cell; and
    wherein said first and second ligand binding domains bind the same ligand outside said cell, and
    wherein said first and second exogenous sensors are configured such that said protease domain will cleave said protease cleavage site when said first and second ligand binding domains bind said ligand outside said cell.

12. The composition of claim 11, wherein said first ligand binding domain or said second ligand binding domain comprises a single chain variable fragment of an antibody (scFv).

13. The composition of claim 11, wherein said first exogenous sensor or said second exogenous sensor further comprises an extracellular spacer.

14. The composition of claim 11, wherein said first exogenous extracellular or said second exogenous extracellular sensor further comprises an intracellular spacer that is one, two, three, four, five, or six amino acids in length.

15. The composition of claim 11, wherein said functional domain is a transcription factor.

16. The composition of claim 15, further comprising a genetic construct, wherein said genetic construct is configured to express a gene in response to said transcription factor and said genetic construct is located in said cell.

17. A composition comprising:
  i) first and second exogenous sensors wherein said first exogenous sensor comprises:
    a) a first ligand binding domain, said ligand binding domain comprising a ligand binding domain of a cell surface receptor;
    b) a transmembrane domain,
    c) a protease cleavage site, and
    d) a functional domain;
    and wherein said second exogenous sensor comprises:
    e) a second ligand binding domain,
    f) a transmembrane domain, and
    g) a protease domain; and
  ii) a cell, wherein said first and second exogenous sensors are located in the cell membrane such that the first and second ligand binding domains are located outside said cell; and wherein said protease cleavage site and said functional domain are located inside said cell; and
  wherein said first and second ligand binding domains bind the same ligand outside said cell, and
  wherein said first and second exogenous sensors are configured such that said protease domain will cleave said protease cleavage site when said first and second ligand binding domains bind said ligand outside said cell.

18. The composition of claim 17, wherein said cell surface receptor is selected from a group consisting of cytokine receptors, chemokine receptors, innate immune receptors, olfactory receptors, steroid hormone receptors, growth factor receptors, mutant receptors that occur in cancer, and neurotransmitter receptors.

19. The composition of claim 17, wherein said functional domain is a transcription factor.

20. The composition of claim 19, further comprising a genetic construct, wherein said genetic construct is configured to express a gene in response to said transcription factor and said genetic construct is located in said cell.

* * * * *